(12) United States Patent
Xu

(10) Patent No.: US 10,093,674 B2
(45) Date of Patent: Oct. 9, 2018

(54) SUPRAMOLECULAR NANOFIBERS AND HYDROGELS BASED ON NUCLEIC ACIDS FUNCTIONALIZED WITH NUCLEOBASES

(71) Applicant: Brandeis University, Waltham, MA (US)

(72) Inventor: Bing Xu, Newton, MA (US)

(73) Assignee: Brandeis University, Waltham, MA (US)

( * ) Notice: Subject to any disclaimer, the term of this patent is extended or adjusted under 35 U.S.C. 154(b) by 248 days.

(21) Appl. No.: 14/093,974

(22) Filed: Dec. 2, 2013

(65) Prior Publication Data

US 2014/0148410 A1    May 29, 2014

Related U.S. Application Data

(63) Continuation-in-part of application No. PCT/US2012/039822, filed on May 29, 2012, which is a continuation-in-part of application No. PCT/US2012/039821, filed on May 29, 2012.

(60) Provisional application No. 61/491,547, filed on May 31, 2011, provisional application No. 61/491,544, filed on May 31, 2011.

(51) Int. Cl.
| | | |
|---|---|---|
| *C07H 15/203* | (2006.01) | |
| *C07D 473/34* | (2006.01) | |
| *C07D 239/54* | (2006.01) | |
| *C07D 473/18* | (2006.01) | |
| *C07F 9/6512* | (2006.01) | |

(Continued)

(52) U.S. Cl.
CPC ......... *C07D 473/34* (2013.01); *C07D 239/54* (2013.01); *C07D 473/18* (2013.01); *C07F 9/65121* (2013.01); *C07F 9/65616* (2013.01); *C07H 13/04* (2013.01)

(58) Field of Classification Search
CPC .. C07D 239/54; C07D 473/18; C07D 473/34; C07F 9/65121; C07F 9/65616; C07H 13/04
See application file for complete search history.

(56) References Cited

U.S. PATENT DOCUMENTS

| | | |
|---|---|---|
| 5,278,284 A | 1/1994 | Lusk et al. |
| 2002/0081726 A1 | 6/2002 | Russell et al. |

(Continued)

FOREIGN PATENT DOCUMENTS

| | | | |
|---|---|---|---|
| WO | WO-2005/047231 | 5/2005 | |
| WO | WO 2006040646 A1 | * | 4/2006 |

OTHER PUBLICATIONS

McCarthy et al, Bioorganic & Medicinal Chemistry Letters, vol. 16:3809-3812 (2006).*

(Continued)

*Primary Examiner* — Randall L Beane
(74) *Attorney, Agent, or Firm* — LeClairRyan PLLC

(57) ABSTRACT

Disclosed are nucleopeptide compounds that include a nucleobase, and an amino acid. Certain compounds further comprise a glycoside. The compounds may self-assemble to form supramolecular hydrogels. Also, the compounds may be used as a platform to examine specific biological functions (e.g., binding to DNA and RNA) of a dynamic supramolecular system that is able to interact with both proteins and nucleic acids. Other uses include: methods of growing cells and methods of delivering a substance to a cell.

12 Claims, 48 Drawing Sheets

(51) Int. Cl.
*C07F 9/6561* (2006.01)
*C07H 13/04* (2006.01)

(56) References Cited

U.S. PATENT DOCUMENTS

| | | | |
|---|---|---|---|
| 2007/0224273 A1* | 9/2007 | Xu | A61K 9/0014 424/488 |
| 2008/0057005 A1 | 3/2008 | Lehn et al. | |
| 2008/0193968 A1 | 8/2008 | Xu et al. | |

OTHER PUBLICATIONS

Zhang et al., Versatile Small-Molecule Motifs for Self-Assembly in Water and the Formation of Biofunctional Supramolecular Hydrogels, Langmuir, vol. 27(2):529-537 (Jul. 7, 2010).*

Ren et al., Naphthalene, Phenanthrene, and Pyrene as DNA Base Analogues: Synthesis, Structure, and Fluorescence in DNA, J. Am. Chem. Soc., vol. 118(33):7671-7678 (Aug. 21, 1996).*

Liang et al. Supramolecular Hydrogel of a D-Amino Acid Dipeptide for Controlled Drug Release in Vivo, Langmuir (Mar. 16, 2009), vol. 25(15):8419-8422 (Year: 2009).*

Jones et al., "Self-assembling electroactive hydrogels for flexible display technology," J. Phys. Condens. Matter, 22:1-7 (2010).

Li et al., "Molecular Nanofibers of Olsalazine Form Supramolecular Hydrogels for Reductive Release on an Anti-inflammatory Agent," J. Am. Chem. Soc., 132:17707-17709 (2010).

Li et al., "Multifunctional, Biocompatible Supramolecular Hydrogelators Consist Only of Nucleobase, Amino Acid, and Glycoside," J. Am. Chem. Soc., 133:17513-17518 (2011).

Yang et al., "Supramolecular hydrogels based on biofunctional nanofibers of self-assembled small molecules," J. Mater. Chem., 17:2385-2393 (2007).

International Search Report dated Jan. 3, 2013, from PCT/US2012/039821.

International Search Report dated Jan. 30, 2013, from PCT/US2012/039822.

* cited by examiner (a)

| Sample | 1A | 1G | 1T | 1C | 3A | 3G | 3T | 3C |
|---|---|---|---|---|---|---|---|---|
| wt % | 2.0 | 2.0 | 2.0 | 2.0 | 2.0 | 2.0 | 2.0 | 2.0 |
| pH | 5.0 | 5.0 | 5.0 | 5.0 | 7.4 | 7.4 | 7.4 | 7.4 |
| Optical images | | | | | | | | |
| Width of nanofibers (nm) | 16 | 15 | 9 | 10 | 20 | 14 | 9 | 5[a] |
| Critical strain (%) | 1.0 | 0.8 | 1.2 | 0.6 | 0.4 | 2.0 | 8.0 | - |
| G' (pa) | 8090 | 12613 | 6346 | 26 | 2082 | 682 | 2.9 | - |
| IC$_{50}$ (μM) | >500 | >500 | >500 | >500 | >500 | >500 | >500 | >500 |

(a)

(b)

(i) DIC, NHS; (ii) L-Phe; (iii) D-glucosamine; (iv) TFA.    Boc = tert-butyloxycarbonyl (a)

(b)

(a)

(b)

(a)

(b)

(a)

(b)

0 hr 20 hr (i) DIC, NHS; (ii) L-Phe; (iii) D-glucosamine; (iv) 90% TFA; (v) L-Arg(pbf); (vi) L-Gly; (vii) L-Asp(OtBu)

SUPRAMOLECULAR NANOFIBERS AND HYDROGELS BASED ON NUCLEIC ACIDS FUNCTIONALIZED WITH NUCLEOBASES

RELATED APPLICATIONS

This application is a continuation-in-part of International Patent Application serial number PCT/US12/039,821, filed May 29, 2012, which claims the benefit of priority to U.S. Provisional Patent Application Ser. No. 61/491,544, filed May 31, 2011. This application is also a continuation-in-part of International Patent Application serial number PCT/US12/039,822, filed May 29, 2012, which claims the benefit of priority to U.S. Provisional Patent Application Ser. No. 61/491,547, filed May 31, 2011.

GOVERNMENT SUPPORT

This invention was made with government support under DMR 0820492 awarded by the National Institutes of Health and the National Science Foundation. The government has certain rights in the invention.

BACKGROUND OF THE INVENTION

Nucleopeptides are a class of molecules that contain both nucleobases and amino acids, which have considerable biological and biomedical importance. Naturally occurring nucleopeptides, such as willardiine-containing nucleopeptides and peptidyl nucleosides, are antibiotics. A number of unnatural nucleobase-containing peptides, such as peptide nucleic acids (PNA), have applications in biology and biomedicine (e.g., as analogues of DNA). Such biological significance renders nucleopeptides useful molecules for studying biology.

Hydrogels, which consist of crosslinked matrices and water, have emerged as an important class of biomaterials due to their morphological similarity to extracellular matrices (ECM) in tissues and organs. Although both natural polymers (e.g., collagen, gelatin, hyaluronic acid, and alginate) and synthetic polymers (e.g., poly(D-L-lactide-co-glycolide), poly(N-isopropyl acrylic amide), and poly(ethylene oxide)) can serve as hydrogels in biomedical applications (e.g., tissue engineering and drug delivery), the currently known members of each class have considerable drawbacks or limitations. For example, the separation and purification of natural polymers are non-trivial, and synthetic polymers are largely passive even if they are functionalized.

Supramolecular hydrogels, resulting from molecular self-assembly of nucleopeptides in water, have exhibited considerable promise for applications in biomedicine due to their inherent biocompatibility and biodegradability.

Nanofibers, comprised of self-assembled peptides, that form supramolecular hydrogels have shown considerable promise. These self-assembled peptides have served as scaffolds to guide the differentiation of neuron progenitor cells, media for cell culture, and carriers for drug release. Like modified peptides, derivatives of glycosides can also self-assemble into nanofibers to give supramolecular gels or hydrogels, which has led to the development of semi-wet peptide/protein arrays as biosensors and intelligent soft materials. Recently, nanofibers of deoxynucleic acid (DNA) were found to form supramolecular hydrogels.

SUMMARY OF THE INVENTION

A hydrogelator of Formula I(a) or Formula I(b)

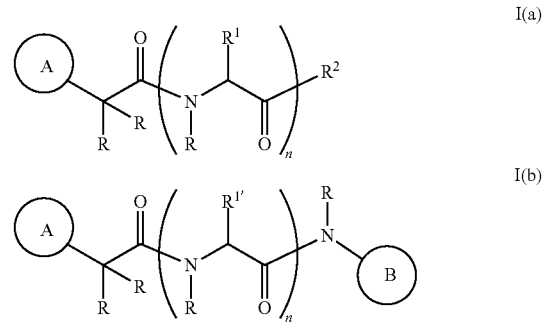

wherein, independently for each occurrence,

is cytosinyl, guaninyl, adeninyl, thyminyl, uracilyl, or an oligonucleic acid;
R is H or alkyl;
$R^1$ is H, alkyl, alkylthioalkyl, aralkyl, heteroaralkyl, hydroxyaralkyl, phosphorylated aralkyl, $HO_2C$-alkyl, or guanidinylalkyl;
$R^2$ is H, alkyl, —OR, or —$NR_2$;
n is 1, 2, 3, 4, 5, 6, 7, 8, 9, 10, 11, 12, 13, 14, 15, 16, 17, 18, 19, or 20;

is fructosyl, galactosyl, glucosyl, mannosyl, or an oligosaccharide; and
$R^{1'}$ is H, alkyl, alkylthioalkyl, aralkyl, heteroaralkyl, hydroxyaralkyl, $HO_2C$-alkyl, or guanidinylalkyl.

BRIEF DESCRIPTION OF THE FIGURES

FIG. 4 depicts a summary of the preparation conditions used, and properties of the nucleopeptide hydrogelators and corresponding supramolecular nanofibers and hydrogels. ᵃThe thin nanofibers (3C) have low quantity and coexist with nanoparticles, thus failing to produce a hydrogel.

DETAILED DESCRIPTION OF THE INVENTION

Definitions

Figure 1:
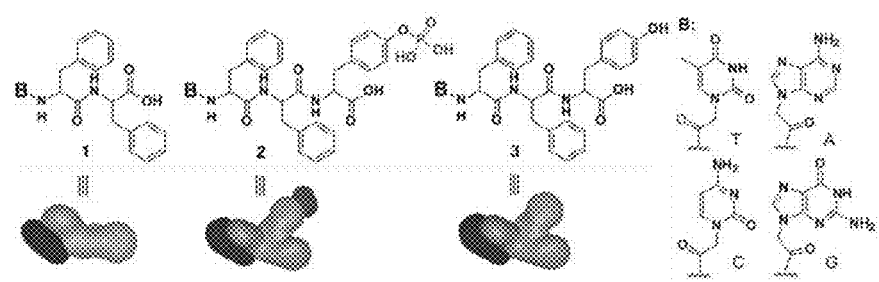
FIG. 1 depicts (a) the molecular structures and simulated 3D shapes of exemplary hydrogelators and corresponding precursors based on nucleopeptides; and (b) a schematic showing self-assembly.
Figure 1:
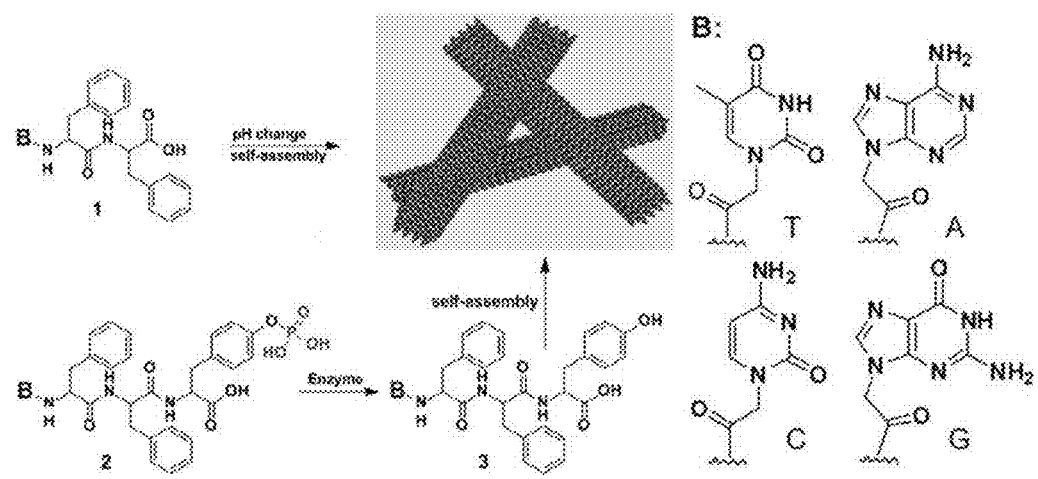

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

In order for the present invention to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of" "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

For purposes of this invention, the chemical elements are identified in accordance with the Periodic Table of the Elements, CAS version, Handbook of Chemistry and Physics, 67th Ed., 1986-87, inside cover.

Oligopeptides Functionalized with Nucleobases
Overview

In certain embodiments, the invention relates to a nucleopeptide compound, comprising, consisting essentially of, or consisting of a nucleobase; and an oligopeptide.

In certain embodiments, the invention relates to the use of a nucleopeptide as a biomaterial. In certain embodiments, the biomaterial may be used as a platform to examine specific biological functions (e.g., binding to DNA and RNA) of a dynamic supramolecular system that is able to interact with both proteins and nucleic acids.

In certain embodiments, the invention relates to a hydrogel formed by an enzymatic reaction upon a nucleopeptide of the invention. In certain embodiments, the invention relates to a hydrogel formed from a nucleopeptide of the invention upon a change in pH.

In certain embodiments, the invention relates to a soft, biocompatible material, comprising, consisting essentially of, or consisting of a nucleopeptide.

Hydrogelator Design, Synthesis, and Discussion

As shown in FIG. 1a, the connection of a nucleobase (adenine, guanine, thymine, or cytosine) to a dipeptide segment (Phe-Phe), which is prone to self-assembly, affords a series of nucleopeptides (1) ("hydrogelators") that self-assemble in water to form nanofibers and produce hydrogels at the concentration of 2.0 wt % and pH around 5. The conjugation of a tyrosine phosphate to 1 yields another group of nucleopeptides, precursors 2, which undergo catalytic dephosphorylation to generate hydrogelators 3 that result in supramolecular nanofibers and hydrogels at low concentration (2.0 wt %) and physiological pH.

Figure 2:
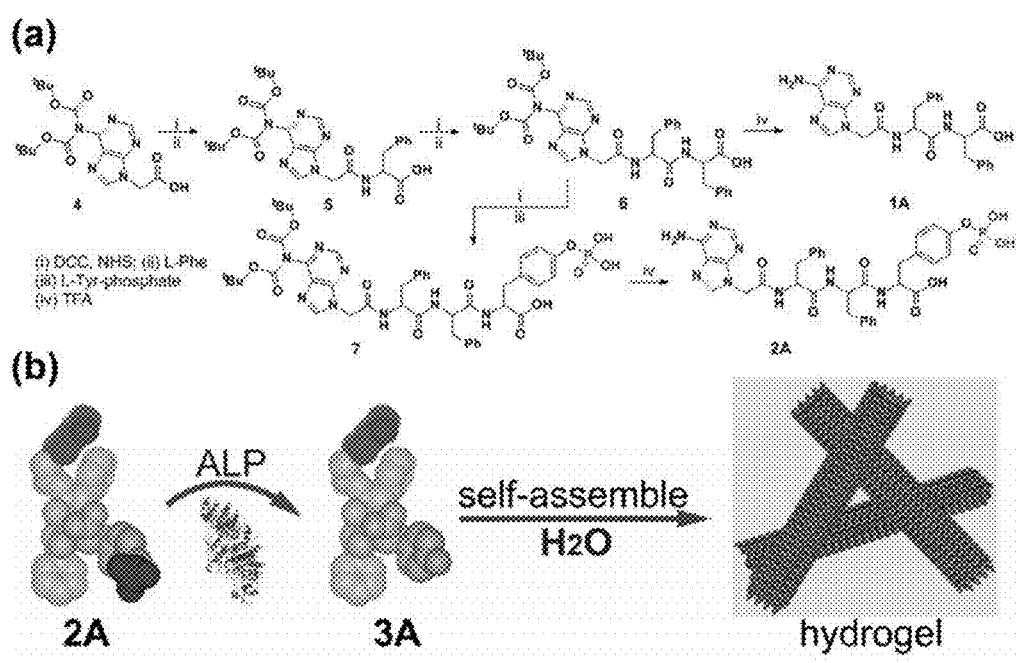
FIG. 2 depicts (a) an exemplary synthetic route to hydrogelator 1A and precursor 2A based on adenine; and (b) an illustration of the dephosphorylation process catalyzed by alkaline phosphatase (ALP) that converts 2A to 3A, resulting in nanofibers and a hydrogel.

FIG. 2a shows a synthetic route exemplified by the process for making the hydrogelators based on adenine. Following the procedures reported by Nieddu for making nucleobase acetic acids, we first synthesized bis(tert-butyloxycarbonyl) (bis-Boc) protected adenine, ($N^6$-bis-Boc-adenine-9-yl)-acetic acid (4). After being activated by N-hydroxysuccinimide (NHS), 4 reacts with L-Phe to afford 5, which undergoes the same NHS activation and phenylalanine coupling to give the key intermediate 6. Subsequent removal of the Boc-protecting groups with trifluoroacetic acid (TFA) yields the nucleopeptides (1A) in 47% total yield. 1A self-assembles to form nanofibers with a diameter of 16 nm (FIG. 5) and results in a hydrogel at a concentration of 2.0 wt % and pH of 5.0. Encouraged by this data, we used the NHS-activated intermediate 6 to react with L-Tyr-phosphate to obtain 7, which forms precursor 2A after the deprotection of the Boc groups. FIG. 2b illustrates the dephosphorylation process of precursor 2A catalyzed by an enzyme, which leads to a translucent hydrogel of nucleopeptide 3A (FIG. 4) at the physiological pH. A $^{31}$P NMR study confirms that precursor 2A completely transforms into hydrogelator 3A 12 h after the addition of alkaline phosphatase (ALP) (FIG. 6), and the TEM images (FIG. 5) of the negative stained hydrogel of 3A reveals nanofibers with a width of 20 nm, confirming that nanofibers of 3A act as a matrix to sustain the hydrogel (with a storage modulus around 2082 Pa at 2.0 wt %).

The formation of the nanofibers from 1A and 3A indicates that the direct attachment of a purine or pyrimidine base to a small peptide is a valid approach to designing hydrogelator nucleopeptides. To examine the generality of this approach, we used synthetic procedures similar to those in FIG. 2a to produce nucleopeptides consisting of other nucleobases (G, T, or C), and examined their abilities to form nanofibers and hydrogels. As revealed by TEM (FIG. 5), hydrogelators 1G, 1T, and 1C self-assemble to form nanofibers with a width of 15, 9, and 10 nm, respectively, and the nanofibers entangle to trap water and result in the hydrogels (FIG. 4) at a concentration of 2.0 wt % and pH 5.0.

Like 2A, precursors 2G and 2T, at 2.0 wt % and pH 7.4, upon the addition of alkaline phosphatase (ALP, 10 U), turn into hydrogelators 3G and 3T, respectively. This enzymatic conversion leads to the formation of nanofibers of 3G and 3T, and results in the corresponding hydrogels shown in FIG. 4. TEM reveals that the diameters of the nanofibers of 3G (14 nm) and 3T (9 nm) are similar to those of the nanofibers of 1G and 1T, respectively. At a concentration of 2.0 wt % and pH 7.4, 3C self-assembles to afford both nanoparticles (11 nm) and short, thin nanofibers (4 nm in diameter and about 200 nm long), but fails to form well-defined nanofiber networks that produce a hydrogel.

We measured the rheological properties of the hydrogels to gain further insight into their characteristics. As shown in FIG. 4, the hydrogel of 1G exhibits the highest storage modulus (12613 Pa), the hydrogels of 1A and 1T possess relatively high storage moduli of 8090 Pa and 6346 Pa, respectively, and the hydrogel of 1C has the lowest storage modulus (26 Pa). The storage moduli of the hydrogels of 3G and 3T are 682 Pa and 2.9 Pa, respectively, indicating that the hydrogel of 3T possesses much weaker mechanical strength than those of the hydrogels 3A and 3G (FIG. 4). The relatively high storage moduli of hydrogels of 1A, 1G, 3A, and 3G may stem from the fact that purine bases favor the formation of Hoogsteen base pairing, in addition to the strong π-π interaction found in purine nucleobases that contain two fused five- and six-member heterocyclic rings. Moreover, the lower storage moduli of the hydrogels of 3 as compared to those of the hydrogels of 1 suggest that the presence of tyrosine may reduce the efficiency of the non-covalent interactions required for the stabilization of self-assembled nanostructures, resulting in the relatively weak viscoelastic properties of those hydrogels.

We used circular dichroism (CD) spectroscopy to study the superstructures in the gel phase of the nanofibers of self-assembled nucleopeptides. The CD spectra of the hydrogels of 1 show a positive peak near 195 nm and a negative peak around 210 nm (FIG. 10), suggesting these nucleopeptides arrange into β-sheet-like configurations. The CD spectra of the hydrogels of 3A, 3G, and 3T display a positive peak near 195 nm and a negative peak around 210 nm, also suggesting that these nucleopeptides adopt a β-sheet-like configuration. The CD spectrum of a solution of 3C exhibits a positive peak near 203 nm and a negative peak around 215 nm, which is red-shifted with respect to the absorbances found in a typical β-sheet. The red-shifted β-sheet signal is likely indicative of a twisted structure as opposed to the standard planar β-sheet; an increase in β-sheet twisting causes disorder and may result in short nanofibers and nanoparticles, which, in turn, leads to weak mechanical strength. Overall, the signals indicating a β-sheet configuration (i.e., transitions at 195 nm-225 nm) of 1 are stronger than those of 3. This corresponds with the observed storage moduli trends—the storage moduli of hydrogels based on 1 are larger than those of hydrogels based on 3.

Figure 5:
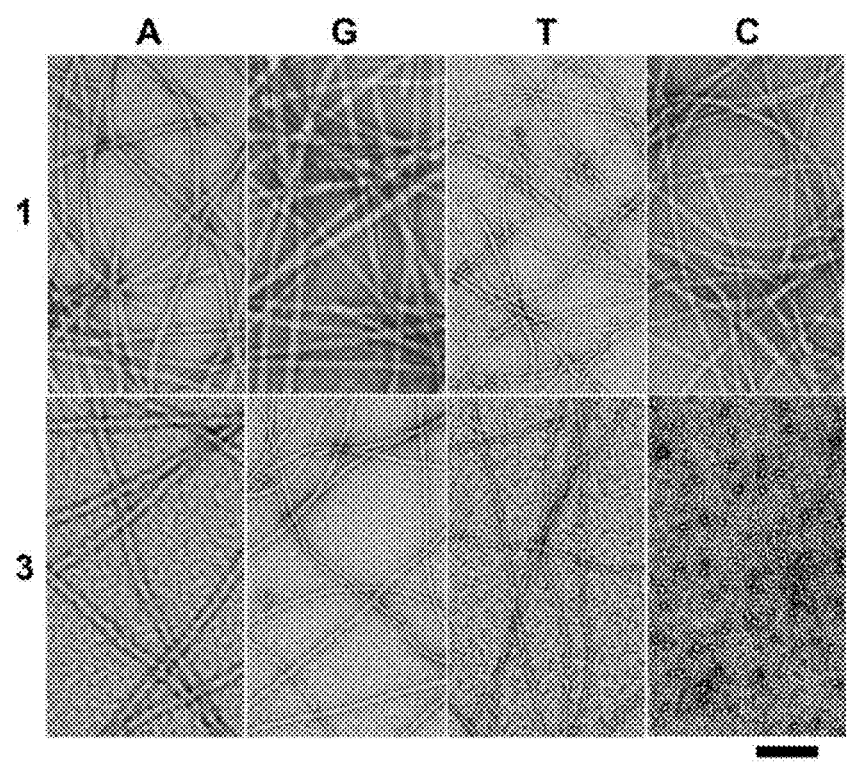
FIG. 5 depicts transmission electron micrographs of the hydrogels formed from 1A, 1G, 1T, 1C, 3A, 3G, 3T and the solution of 3C (scale bar=100 nm).
Figure 6:
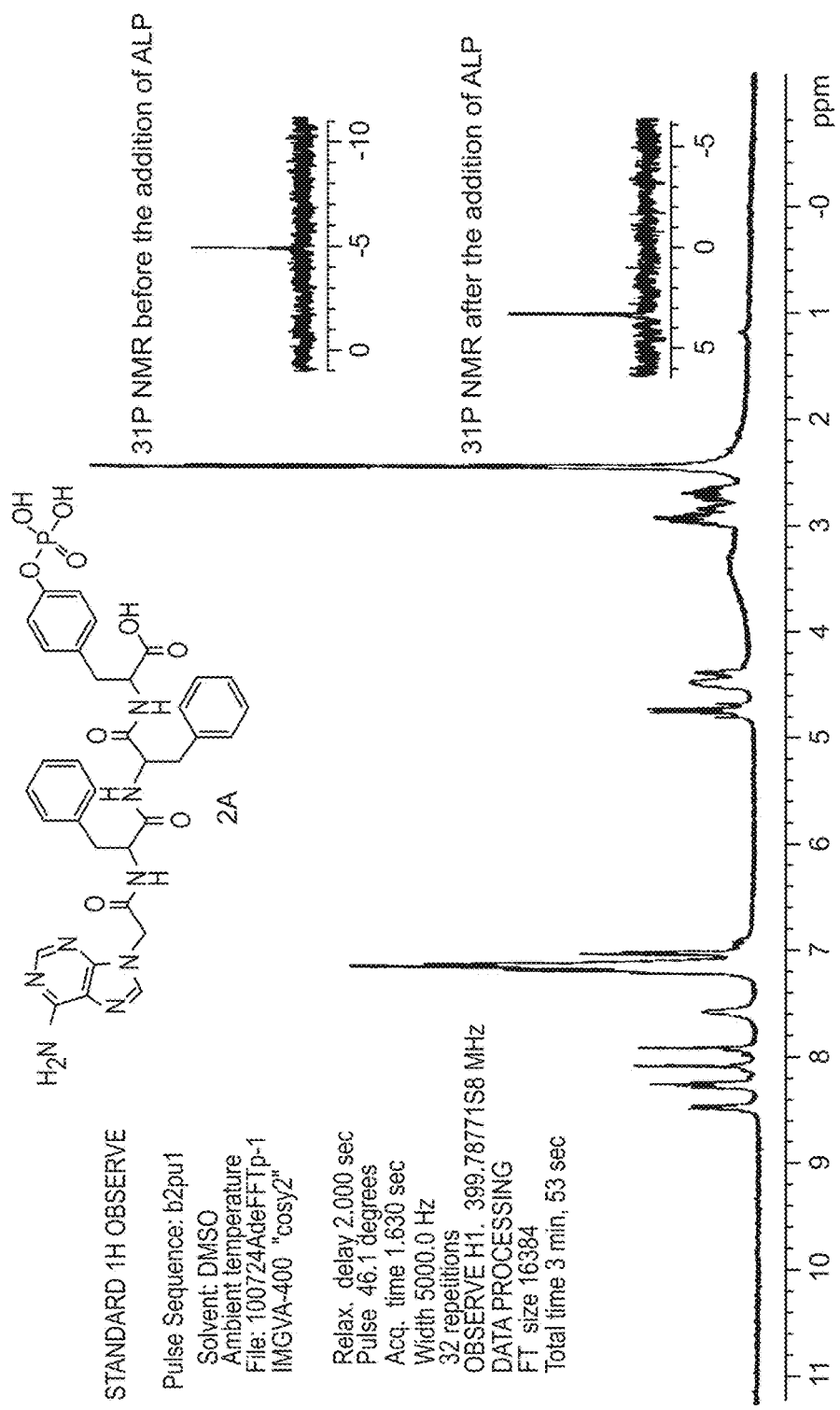
FIG. 6 depicts the $^1$H NMR spectrum of nucleopeptide hydrogelator 2A, and $^{31}$P NMR spectra before and after the addition of alkaline phosphatase (ALP) to 2A.
Figure 7:
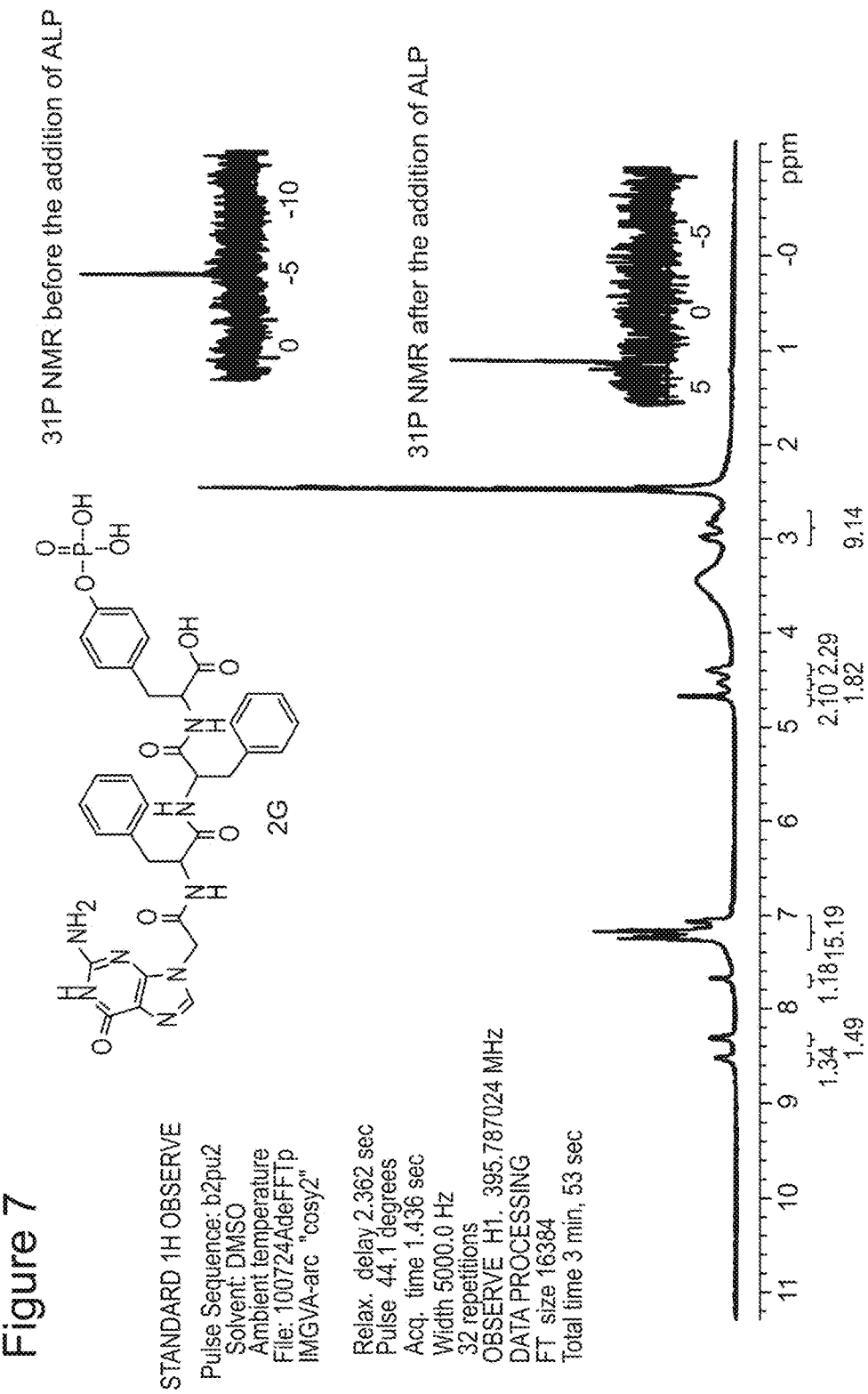
FIG. 7 depicts the $^1$H NMR spectrum of nucleopeptide hydrogelator 2G, and $^{31}$P NMR spectra before and after the addition of alkaline phosphatase (ALP) to 2G.
Figure 8:
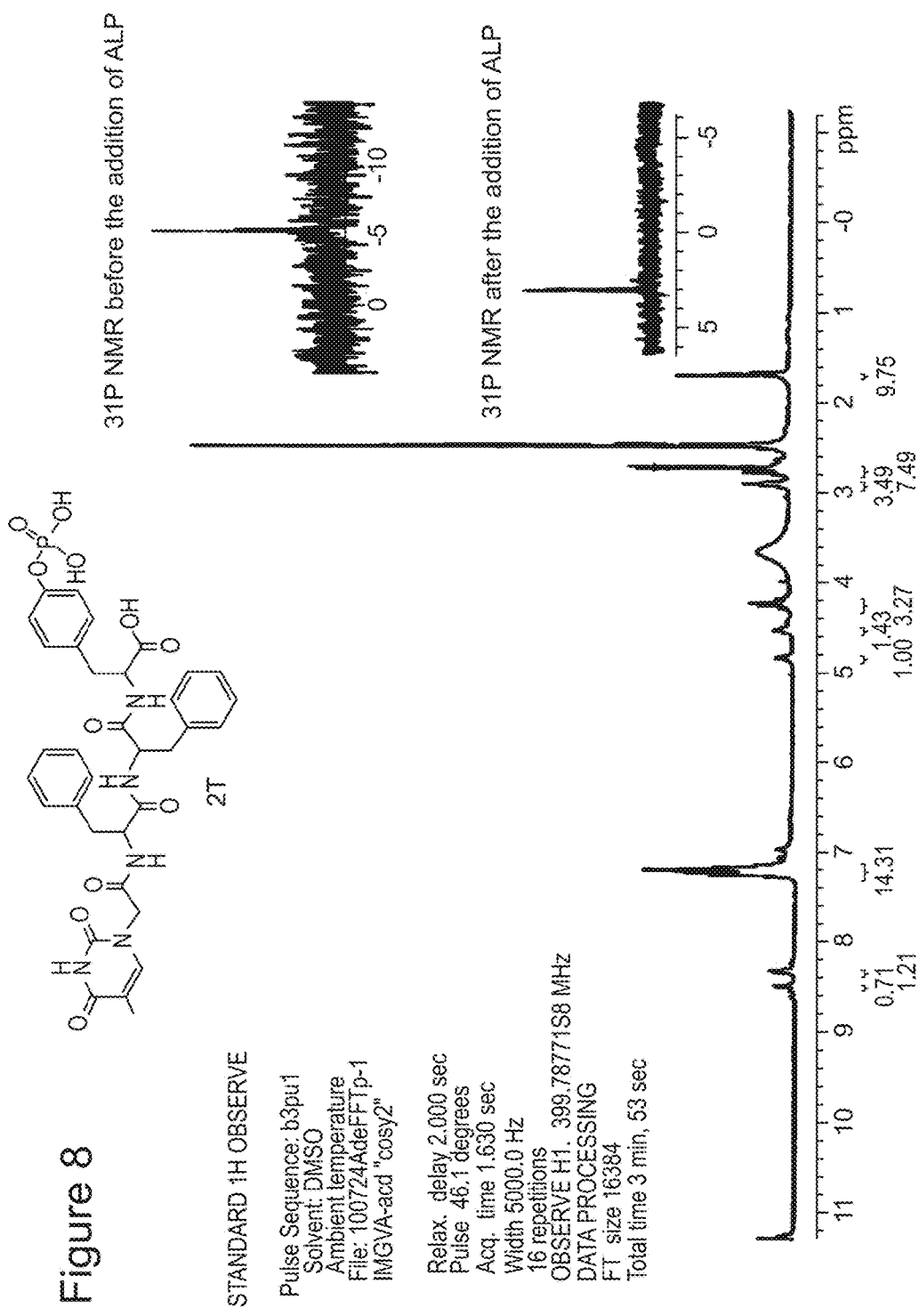
FIG. 8 depicts the $^1$H NMR spectrum of nucleopeptide hydrogelator 2T, and $^{31}$P NMR spectra before and after the addition of alkaline phosphatase (ALP) to 2T.
Figure 9:
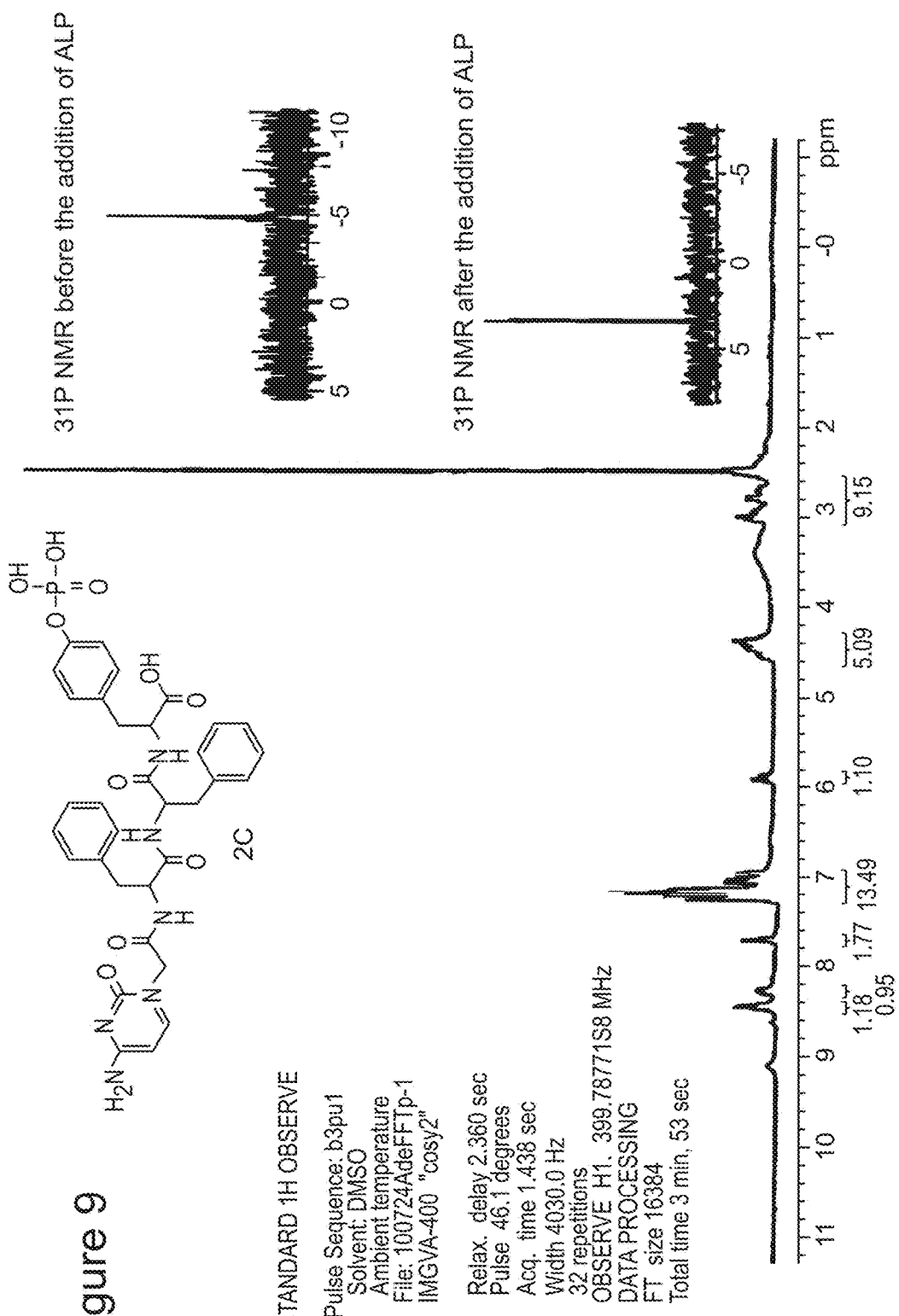
FIG. 9 depicts the $^1$H NMR spectrum of nucleopeptide hydrogelator 2C, and $^{31}$P NMR spectra before and after the addition of alkaline phosphatase (ALP) to 2C.
Figure 13:
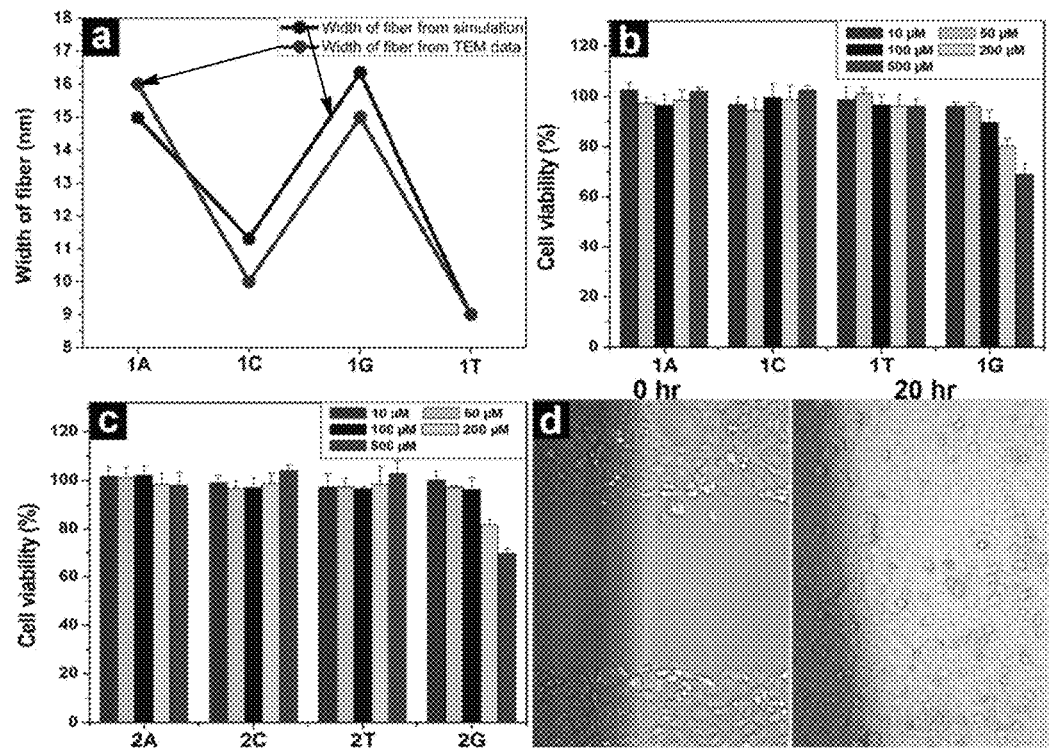
FIG. 13 depicts (a) a comparison of the widths of fibers of hydrogels 1A, 1C, 1G and 1T, based on transmission electron micrographs and molecular mechanical calculations; (b) 72 h cell viability test at concentrations of, from left to right, 10 μM, 50 μM, 100 μM, 200 μM, and 500 μM of 1A, 1C, 1T and 1G; (c) 72 h cell viability test at concentrations of, from left to right, 10 μM, 50 μM, 100 μM, 200 μM, and 500 μM of 2A, 2C, 2T and 2G; and (d) optical images of HeLa cells on the surface 0 h and 20 h after the creation of scratch-wound in the presence of hydrogel 3T (by adding 27.7 mM of 3T to the media).

We also used molecular mechanical (MM) calculations to simulate the width of the nanofibers of 1. As shown in FIG. 13a, the simulated widths of the nanofibers are 15 nm, 16 nm, 9 nm and 11 nm for nucleopeptides 1A, 1G, 1T and 1C, respectively. The calculated values correlate well with the observed values (FIG. 5). According to simulation, the thicker width of nanofibers in the hydrogels of 1A and 1G likely result from the formation of Hoogsteen base pairing by adenine or guanine nucleobases. In addition, the MM calculations support the theory that the molecules self-assemble into a β-sheet-like structure.

To verify the biocompatibility of the hydrogelators, we added hydrogelator 1 or precursor 2 into the culture of HeLa cells and measured the proliferation of the cells. According to the MTT assay shown in FIG. 13, after being incubated with the 500 μM of hydrogelator (1A, 1T, or 1C) or the precursor (2A, 2T, or 2C) for 72 hours, the cell viability remained at 100%. Although the cell viability decreases slightly when the cells are incubated with 500 μM of 1G or 2G for 72 hours, the $IC_{50}$ is still >500 μM. These results support the notion that nucleopeptides 1, 2, and 3 are biocompatible.

We also used a simple wound-healing assay to examine the capability of the nanofibers and hydrogels of 3 to serve as a material for maintaining cell-matrix interaction. As shown in FIG. 13d, the presence of the hydrogel of 3T in cell culture has little inhibitory effect on the migration of cells, further supporting the biocompatibility of 3.

Exemplary Hydrogelators of the Invention

In certain embodiments, the invention relates to a hydrogelator of Formula I(a)

I(a)

wherein, independently for each occurrence, (A)

is cytosinyl, guaninyl, adeninyl, thyminyl, uracilyl, or an oligonucleic acid;

R is H or alkyl;

$R^1$ is H, alkyl, alkylthioalkyl, aralkyl, heteroaralkyl, hydroxyaralkyl, phosphorylated aralkyl, $HO_2C$-alkyl, or guanidinylalkyl;

$R^2$ is H, alkyl, —OR, or —$NR_2$; and n is 1, 2, 3, 4, 5, 6, 7, 8, 9, 10, 11, 12, 13, 14, 15, 16, 17, 18, 19, or 20.

In certain embodiments, the invention relates to any one of the aforementioned hydrogelators, wherein (A)

is cytosinyl. In certain embodiments, the invention relates to any one of the aforementioned hydrogelators, wherein (A)

is guaninyl. In certain embodiments, the invention relates to any one of the aforementioned hydrogelators, wherein (A)

is adeninyl.

In certain embodiments, the invention relates to any one of the aforementioned hydrogelators, wherein (A)

is thyminyl. In certain embodiments, the invention relates to any one of the aforementioned hydrogelators, wherein (A)

is uracilyl. In certain embodiments, the invention relates to any one of the aforementioned hydrogelators, wherein (A)

is an oligonucleic acid.

In certain embodiments, the invention relates to any one of the aforementioned hydrogelators, wherein R is H.

In certain embodiments, the invention relates to any one of the aforementioned hydrogelators, wherein $R^1$ is H.

In certain embodiments, the invention relates to any one of the aforementioned hydrogelators, wherein $R^1$ is alkyl. In certain embodiments, the invention relates to any one of the aforementioned hydrogelators, wherein $R^1$ is methyl. In certain embodiments, the invention relates to any one of the aforementioned hydrogelators, wherein $R^1$ is ethyl. In certain embodiments, the invention relates to any one of the aforementioned hydrogelators, wherein $R^1$ is propyl. In certain embodiments, the invention relates to any one of the aforementioned hydrogelators, wherein $R^1$ is isopropyl. In certain embodiments, the invention relates to any one of the aforementioned hydrogelators, wherein $R^1$ is butyl. In certain embodiments, the invention relates to any one of the aforementioned hydrogelators, wherein $R^1$ is isobutyl. In certain embodiments, the invention relates to any one of the aforementioned hydrogelators, wherein $R^1$ is sec-butyl.

In certain embodiments, the invention relates to any one of the aforementioned hydrogelators, wherein $R^1$ is alkylthioalkyl. In certain embodiments, the invention relates to any one of the aforementioned hydrogelators, wherein $R^1$ is $CH_3$—S—$CH_2CH_2$—.

In certain embodiments, the invention relates to any one of the aforementioned hydrogelators, wherein R¹ is aralkyl. In certain embodiments, the invention relates to any one of the aforementioned hydrogelators, wherein R¹ is benzyl.

In certain embodiments, the invention relates to any one of the aforementioned hydrogelators, wherein R¹ is heteroaralkyl. In certain embodiments, the invention relates to any one of the aforementioned hydrogelators, wherein R¹ is indolyl-CH₂—. In certain embodiments, the invention relates to any one of the aforementioned hydrogelators, wherein R¹ is

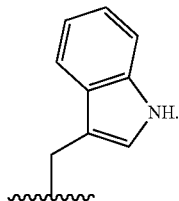 [SMILES: *Cc1c[nH]c2ccccc12]

In certain embodiments, the invention relates to any one of the aforementioned hydrogelators, wherein R¹ is hydroxyaralkyl. In certain embodiments, the invention relates to any one of the aforementioned hydrogelators, wherein R¹ is hydroxybenzyl. In certain embodiments, the invention relates to any one of the aforementioned hydrogelators, wherein R¹ is 4-hydroxybenzyl.

In certain embodiments, the invention relates to any one of the aforementioned hydrogelators, wherein R¹ is phosphorylated aralkyl. In certain embodiments, the invention relates to any one of the aforementioned hydrogelators, wherein R¹ is H₂PO₄-benzyl. In certain embodiments, the invention relates to any one of the aforementioned hydrogelators, wherein R¹ is 4-H₂PO₄-benzyl.

In certain embodiments, the invention relates to any one of the aforementioned hydrogelators, wherein at least one instance of R¹ is aralkyl, hydroxyaralkyl, or phosphorylated aralkyl.

In certain embodiments, the invention relates to any one of the aforementioned hydrogelators, wherein R² is —OR. In certain embodiments, the invention relates to any one of the aforementioned hydrogelators, wherein R² is —OH.

In certain embodiments, the invention relates to any one of the aforementioned hydrogelators, wherein n is 1. In certain embodiments, the invention relates to any one of the aforementioned hydrogelators, wherein n is 2. In certain embodiments, the invention relates to any one of the aforementioned hydrogelators, wherein n is 3.

In certain embodiments, the invention relates to a compound selected from the group consisting of:

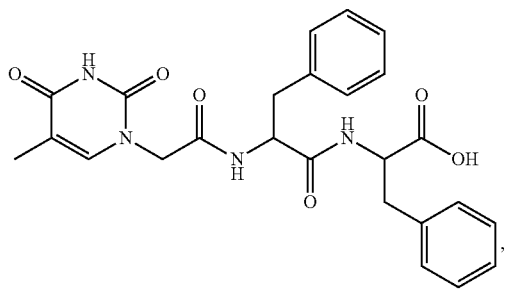

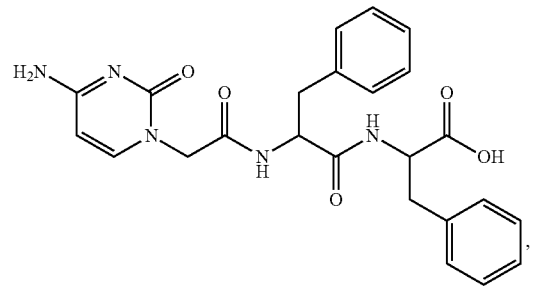

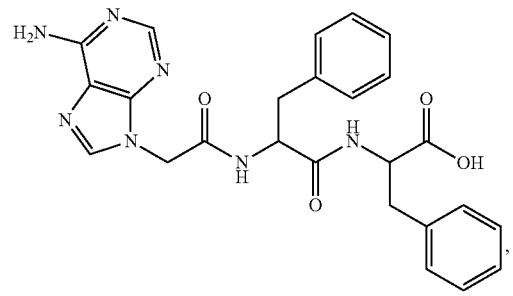

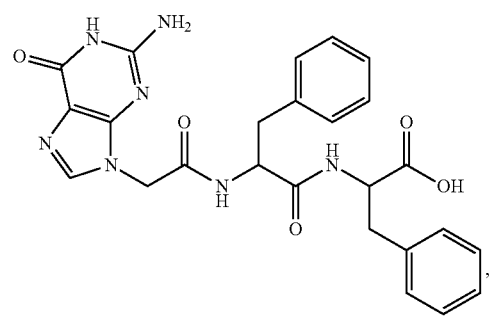

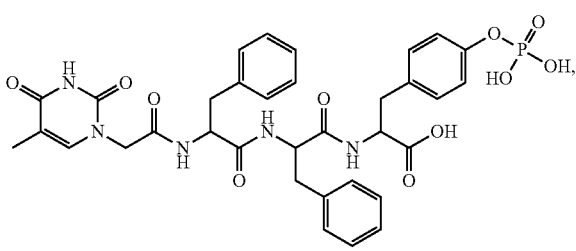

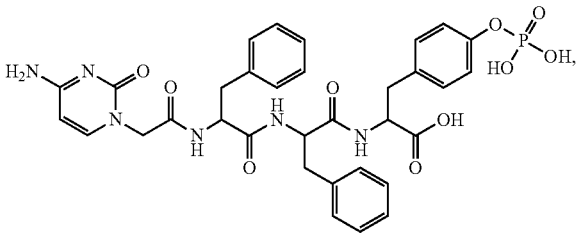

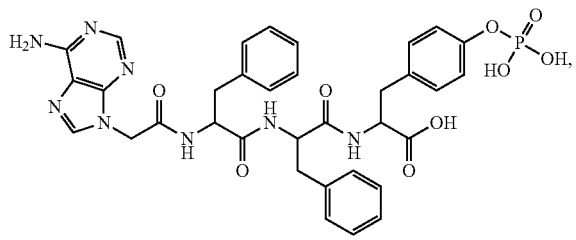

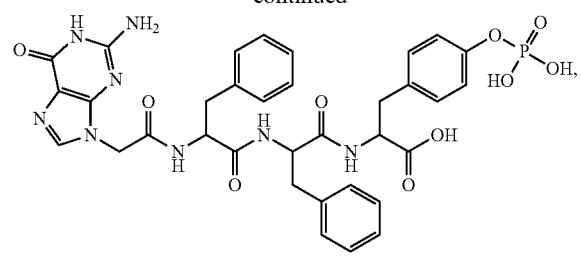
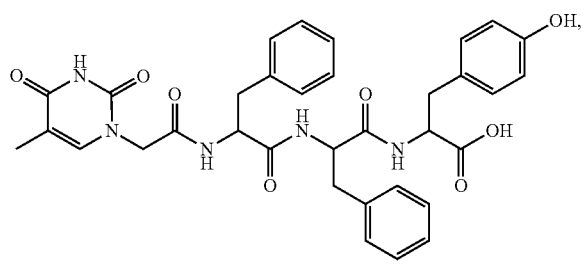
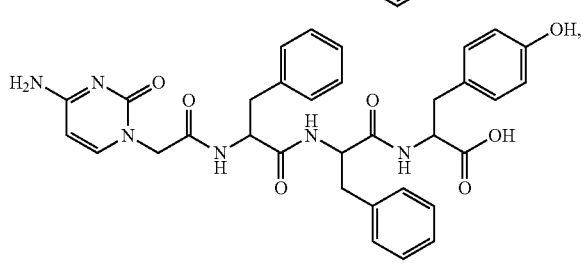
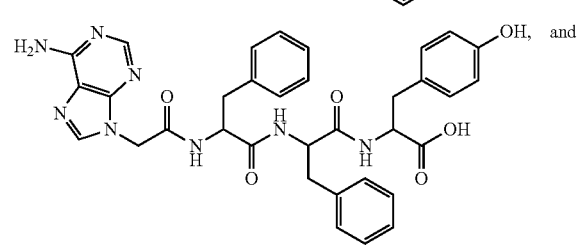
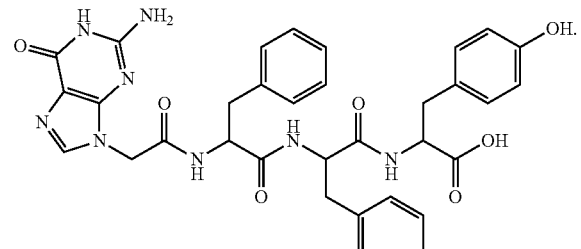
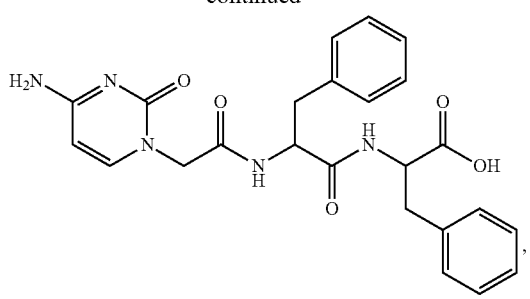
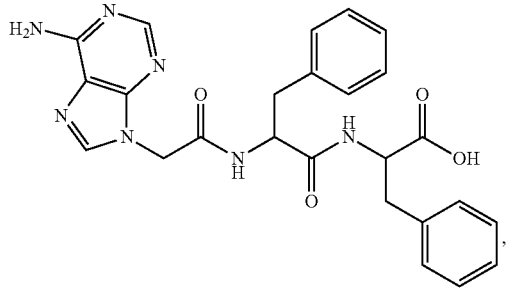
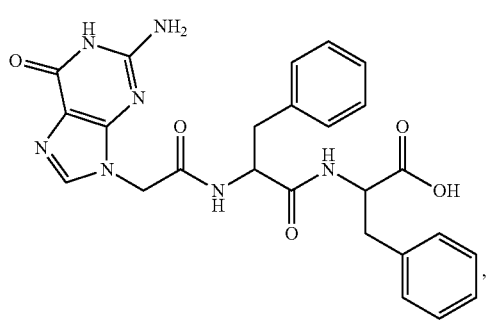
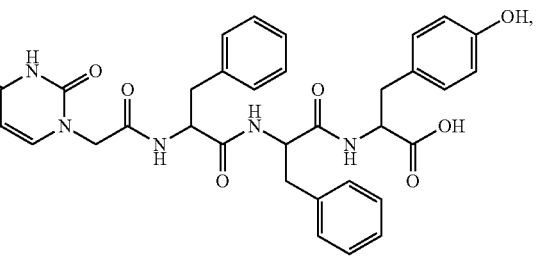
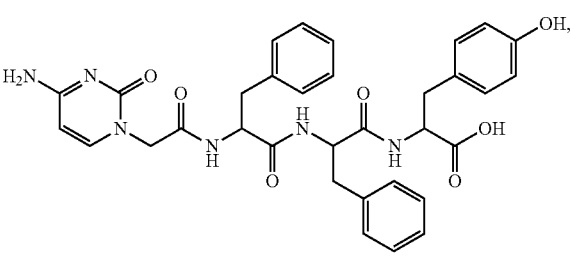
In certain embodiments, the invention relates to a compound selected from the group consisting of:
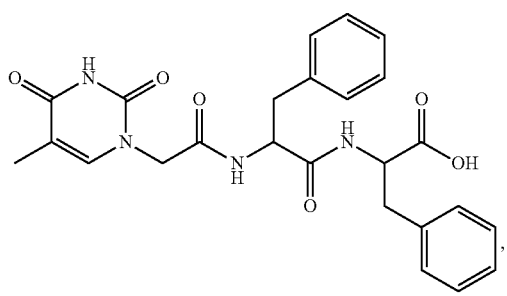
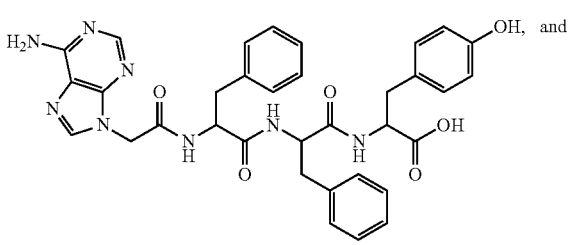

-continued

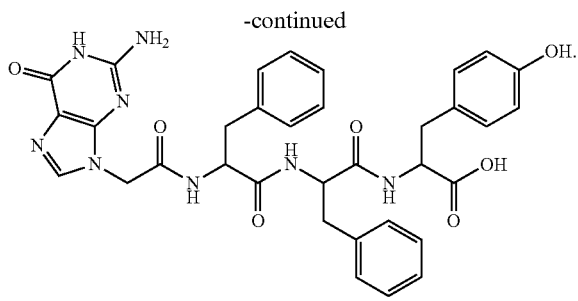

Exemplary Supramolecular Structures of the Invention

In certain embodiments, the invention relates to a supramolecular structure comprising a plurality of any one of the aforementioned hydrogelators.

In certain embodiments, the invention relates to any one of the aforementioned supramolecular structures, wherein the supramolecular structure is in the form of nanofibers. In certain embodiments, the average diameter of the nanofibers is about 3 nm, about 4 nm, about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, or about 25 nm. In certain embodiments, the nanofibers are crosslinked. In certain diameters, the nanofibers are substantially straight. In certain embodiments, the nanofibers are bent. In certain embodiments, the nanofibers form bundles of nanofibers. In certain embodiments, the nanofibers are about 100 nm, about 120 nm, about 140 nm, about 160 nm, about 180 nm, about 200 nm, about 220 nm, about 240 nm, about 260 nm, about 280 nm, or about 300 nm in length. In certain embodiments, the nanofibers are greater than about 100 nm, about 120 nm, about 140 nm, about 160 nm, about 180 nm, about 200 nm, about 220 nm, about 240 nm, about 260 nm, about 280 nm, or about 300 nm in length.

Exemplary Hydrogels of the Invention

In certain embodiments, the invention relates to a hydrogel, comprising, consisting essentially of, or consisting of a plurality of any one of the aforementioned hydrogelators; and water.

In certain embodiments, the invention relates to a hydrogel, comprising, consisting essentially of, or consisting of a plurality of any one of the aforementioned supramolecular structures; and water.

In certain embodiments, the invention relates to any one of the aforementioned hydrogels, wherein the hydrogel is formed from a solution of the hydrogelators in water. In certain embodiments, the hydrogelator is present in an amount from about 0.5% to about 4% by weight. In certain embodiment, the hydrogelator is present in an amount of about 0.5%, about 1.0%, about 1.5%, about 2.0%, about 2.5%, about 3.0%, about 3.5%, or about 4.0% by weight.

In certain embodiments, the invention relates to any one of the aforementioned hydrogels, wherein the hydrogel is formed from a solution of the hydrogelators in water. In certain embodiments, the temperature of the solution is about 20° C., about 25° C., or about 30° C.

In certain embodiments, the invention relates to any one of the aforementioned hydrogels, wherein the hydrogel is formed by decreasing the pH of the solution of hydrogelators in water. In certain embodiments, the pH at which the supramolecular structure is formed is about 8.0, about 7.5, about 7.0, about 6.5, about 6.0, about 5.5, about 5.0, about 4.5, or about 4.0.

In certain embodiments, the invention relates to any one of the aforementioned hydrogels, wherein the hydrogel is formed by the addition of an enzyme to the solution of hydrogelators in water. In certain embodiments, the enzyme is a phosphatase. In certain embodiments, the enzyme is alkaline phosphatase.

In certain embodiments, the invention relates to any one of the aforementioned hydrogels, wherein the hydrogel has a critical strain value of from about 0.2% to about 10.0%. In certain embodiments, the invention relates to any one of the aforementioned hydrogels, wherein the hydrogel has a critical strain value of about 0.2%, about 0.3%, about 0.4%, about 0.5%, about 0.6%, about 0.7%, about 0.8%, about 0.9%, about 1.0%, about 1.2%, about 1.4%, about 1.6%, about 1.8%, about 2.0%, about 2.2%, about 2.4%, about 2.6%, about 2.8%, about 3.0%, about 3.2%, about 3.4%, about 3.6%, about 3.8%, about 4.0%, about 4.2%, about 4.4%, about 4.6%, about 4.8%, about 5.0%, about 5.2%, about 5.4%, about 5.6%, about 5.8%, about 6.0%, about 6.2%, about 6.4%, about 6.6%, about 6.8%, about 7.0%, about 7.2%, about 7.4%, about 7.6%, about 7.8%, about 8.0%, about 8.2%, about 8.4%, about 8.6%, about 8.8%, about 9.0%, about 9.2%, about 9.4%, about 9.6%, about 9.8%, or about 10%.

In certain embodiments, the invention relates to any one of the aforementioned hydrogels, wherein the hydrogel has a storage modulus of from about 2.0 Pa to about 14.0 KPa. In certain embodiments, the invention relates to any one of the aforementioned hydrogels, wherein the hydrogel has a storage modulus of about 2.0 Pa, about 2.1 Pa, about 2.2 Pa, about 2.3 Pa, about 2.4 Pa, about 2.5 Pa, about 2.6 Pa, about 2.7 Pa, about 2.8 Pa, about 2.9 Pa, about 3.0 Pa, about 3.1 Pa, about 3.2 Pa, about 3.3 Pa, about 3.4 Pa, about 3.5 Pa, about 3.6 Pa, about 3.7 Pa, about 3.8 Pa, about 3.9 Pa, about 4.0 Pa, about 5.0 Pa, about 10 Pa, about 15 Pa, about 20 Pa, about 25 Pa, about 30 Pa, about 35 Pa, about 40 Pa, about 45 Pa, about 50 Pa, about 100 Pa, about 150 Pa, about 200 Pa, about 250 Pa, about 300 Pa, about 350 Pa, about 400 Pa, about 450 Pa, about 500 Pa, about 550 Pa, about 600 Pa, about 650 Pa, about 700 Pa, about 750 Pa, about 800 Pa, about 850 Pa, about 900 Pa, about 950 Pa, about 1.0 KPa, about 1.5 KPa, about 2.0 KPa, about 2.5 KPa, about 3.0 KPa, about 3.5 KPa, about 4.0 KPa, about 4.5 KPa, about 5.0 KPa, about 5.5 KPa, about 6.0 KPa, about 6.5 KPa, about 7.0 KPa, about 7.5 KPa, about 8.0 KPa, about 8.5 KPa, about 9.0 KPa, about 9.5 KPa, about 10.0 KPa, about 10.5 KPa, about 11.0 KPa, about 11.5 KPa, about 12.0 KPa, about 12.5 KPa, about 13.0 KPa, about 13.5 KPa, or about 14.0 KPa.

In certain embodiments, the invention relates to any one of the aforementioned hydrogels, wherein the hydrogel is substantially biocompatible. In certain embodiments, the invention relates to any one of the aforementioned hydrogels, wherein the hydrogel is substantially biostable.

Exemplary Methods of the Invention

In certain embodiments, the invention relates to a method of growing cells, comprising contacting a plurality of cells with any one of the aforementioned supramolecular structures or any one of the aforementioned hydrogels. In certain embodiments, the cells are engineered tissue cells.

In certain embodiments, the invention relates to a method of delivering a substance to a cell, comprising contacting the substance with any one of the aforementioned supramolecular structures or any one of the aforementioned hydrogels, thereby forming a substance-hydrogel delivery vehicle; and contacting the substance-hydrogel delivery vehicle and a cell.

In certain embodiments, the invention relates to any one of the aforementioned methods, wherein the substance is a drug. In certain embodiments, the invention relates to any one of the aforementioned methods, wherein the substance is a protein. In certain embodiments, the invention relates to any one of the aforementioned methods, wherein the substance is a gene. In certain embodiments, the invention relates to any one of the aforementioned methods, wherein the substance is siRNA. In certain embodiments, the invention relates to any one of the aforementioned methods, wherein the substance is microRNA. In certain embodiments, the invention relates to any one of the aforementioned methods, wherein the substance is a second cell.

In certain embodiments, the invention relates to a method of binding a nucleic acid, comprising contacting a nucleic acid with any one of the aforementioned supramolecular structures or any one of the aforementioned hydrogels.

In certain embodiments, the invention relates to any one of the aforementioned methods, wherein the nucleic acid binding is selective nucleic acid binding.

In certain embodiments, the invention relates a method of separating a protein from a substance, comprising contacting a mixture with any one of the aforementioned supramolecular structures or any one of the aforementioned hydrogels, wherein the mixture comprises a protein.

In certain embodiments, the invention relates to any one of the aforementioned methods, wherein the mixture comprises at least two proteins.

In certain embodiments, the invention relates to a method of treating or preventing a viral infection, comprising administering to a mammal in need thereof a therapeutically effective amount of any one of the aforementioned hydrogelators.

In certain embodiments, the invention relates to a method of treating or preventing cancer, comprising administering to a mammal in need thereof a therapeutically effective amount of any one of the aforementioned hydrogelators.

In certain embodiments, the invention relates to a method of preventing adhesion of an organism or a cell to a surface, comprising contacting the surface with any one of the aforementioned supramolecular structures or any one of the aforementioned hydrogels.

Nucleic Acids Functionalized with Nucleobases and a Glycoside

Overview

In certain embodiments, the invention relates to a hydrogelator, wherein the hydrogelator comprises, consists essentially of, or consists of a nucleobase, an amino acid, and a glycoside. In certain embodiments, the invention relates to a multifunctional, biocompatible supramolecular nanofiber or hydrogel, comprising, consisting essentially of, or consisting of an aforementioned hydrogelator.

In certain embodiments, the invention relates to a hydrogelator, comprising a nucleobase (e.g., thymine), an amino acid (e.g., phenylalanine), and a glycoside (e.g., D-glucosamine), wherein they are covalently tethered. In certain embodiments, the hydrogelator forms molecular nanofibers that result in a supramolecular hydrogel at pH of about 7.0, and concentration of about 3.0 wt %. In certain embodiments, the invention relates to a nanofiber, comprising a plurality of said hydrogelators. In certain embodiments, the invention relates to a supramolecular hydrogel, comprising a plurality of said nanofibers.

In certain embodiments, the invention relates to a hydrogelator, wherein the hydrogelator comprises thymine, cytosine, adenine, or guanine.

In certain embodiments, the invention relates to a hydrogelator, wherein the hydrogelator comprises alanine, isoleucine, leucine, methionine, phenylalanine, tryptophan, tyrosine, or valine. In certain embodiments, the hydrogelator comprises phenylalanine. In certain embodiments, the hydrogelator comprises diphenylalanine.

In certain embodiments, the invention relates to a hydrogelator, wherein the hydrogelator comprises a glycoside. In certain embodiments, the inclusion of glycoside in the hydrogelator significantly enhances its resistance to proteases. In certain embodiments, the glycoside is or is derived from a glucosamine or a galactosamine.

In certain embodiments, the invention relates to a hydrogelator, wherein the hydrogelator does not inhibit the growth of mammalian cells.

In certain embodiments, the invention relates to a nanofiber or a hydrogel comprising any one of the aforementioned hydrogelators.

Hydrogelator Design, Synthesis, and Discussion

Figure 16:
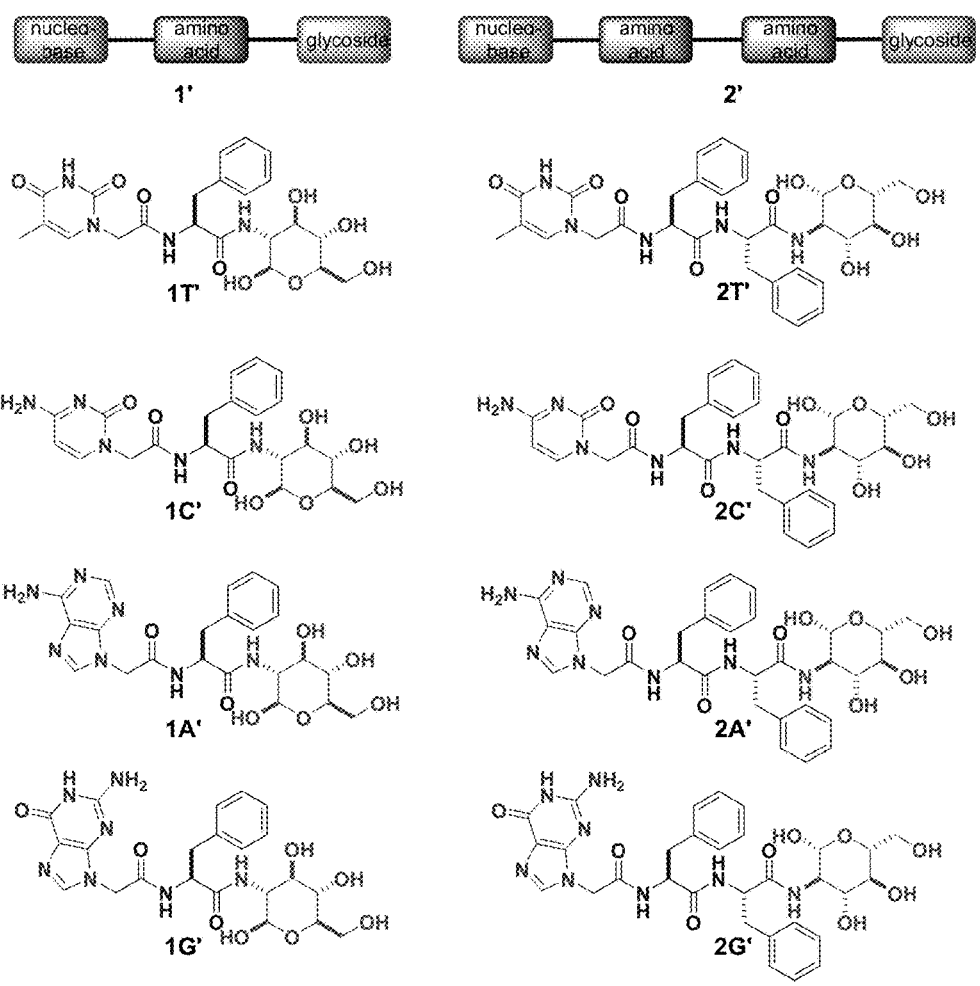
FIG. 16 depicts (a) structures of exemplary hydrogelators (except 1C') comprising nucleobase, amino acid, and glycoside; and (b) a cartoon representing the resulting supramolecular structure.
Figure 16:
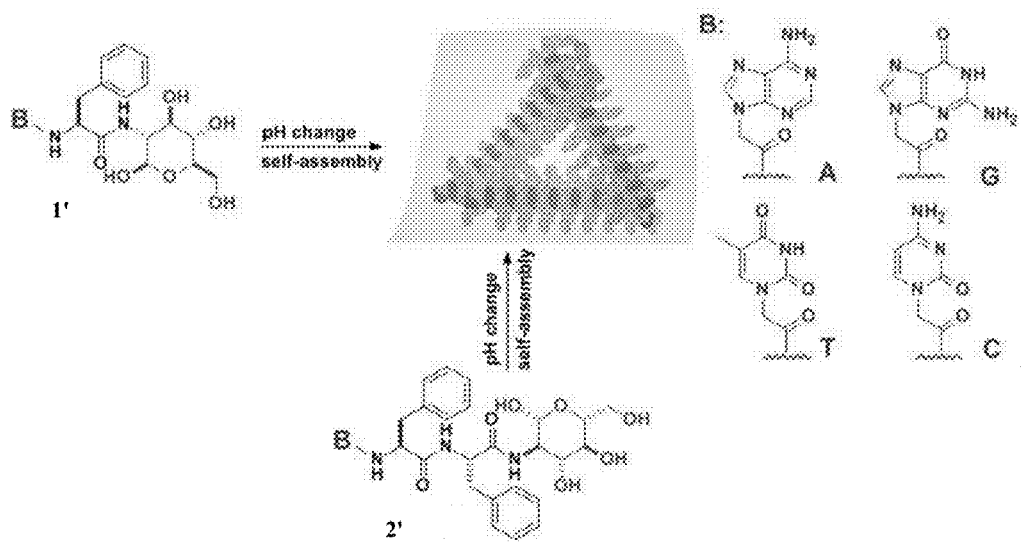
Figure 17:
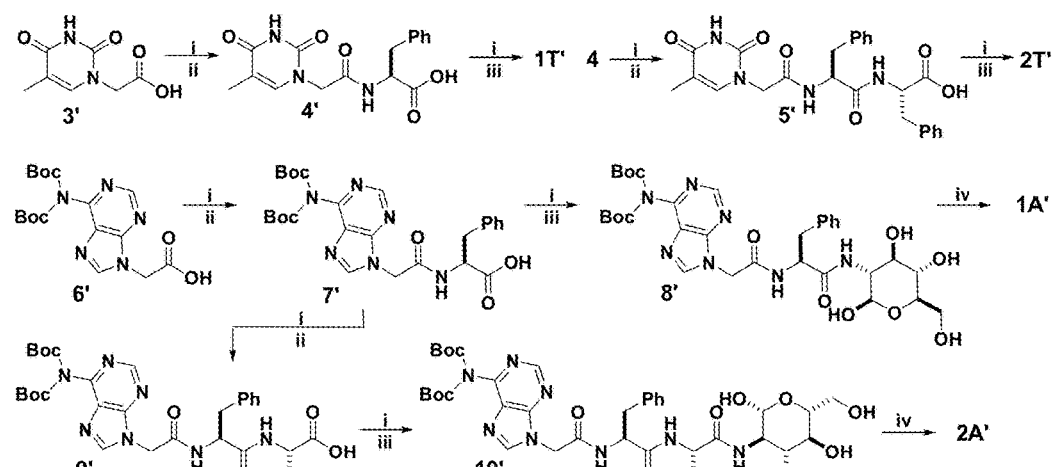
FIG. 17 depicts an exemplary synthetic route for the preparation of hydrogelators 1A' and 2A'.
Figure 18A:
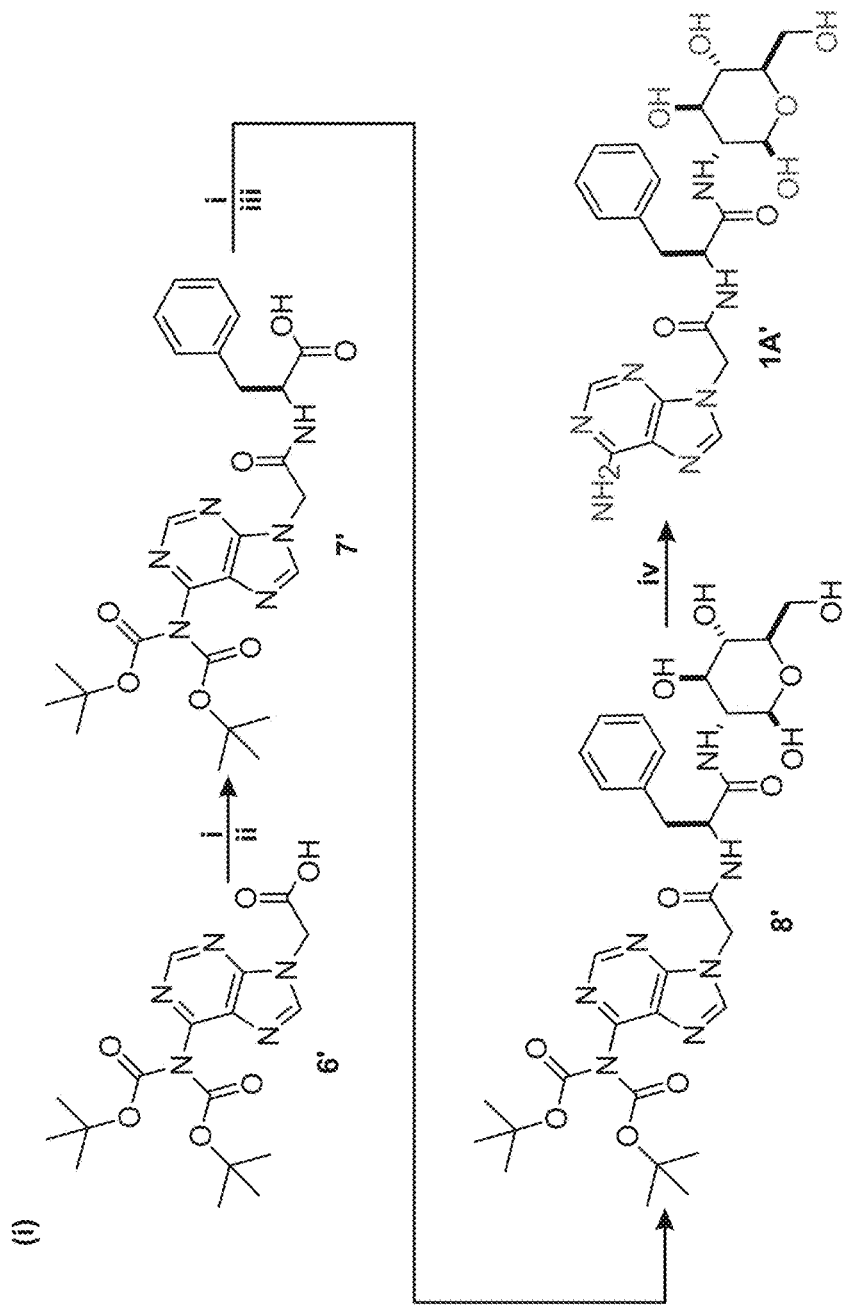
FIG. 18 depicts the molecular structures and exemplary synthetic routes for the preparation of hydrogelators 1A', 2A', 2C', 1G', 2G', and compound 1C'.
Figure 18B:
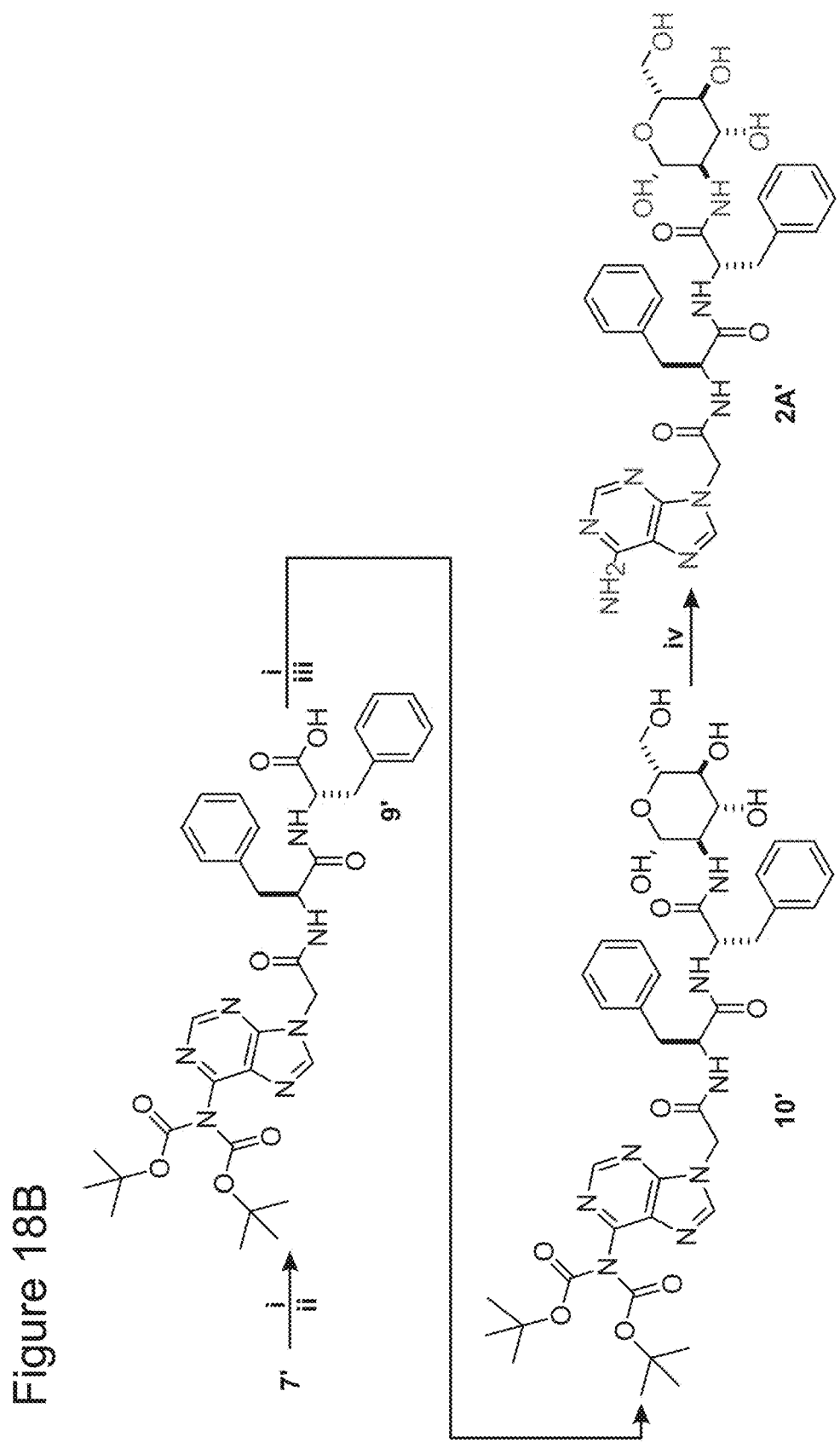
Figure 18C:
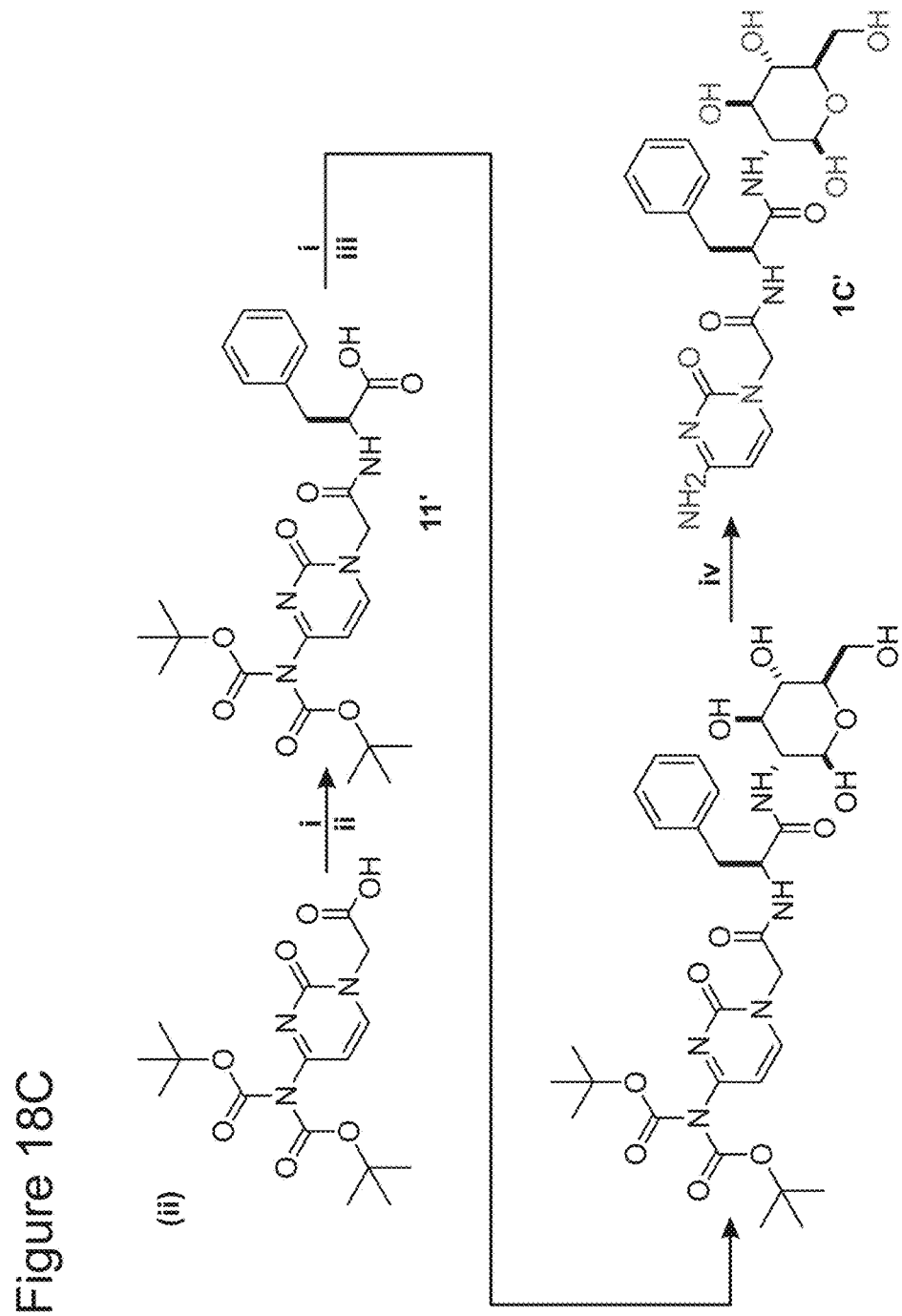
Figure 18D:
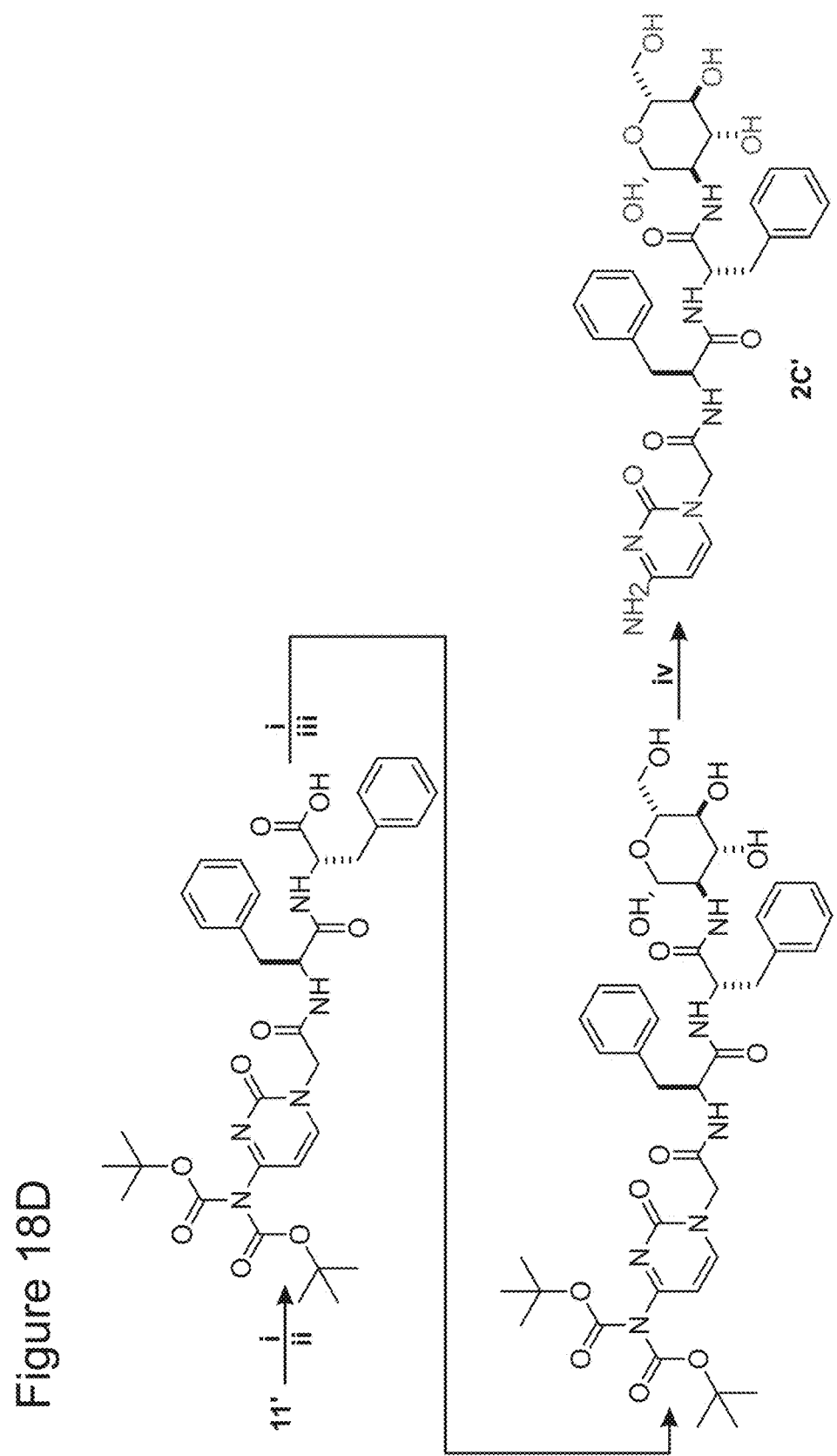
Figure 18E:
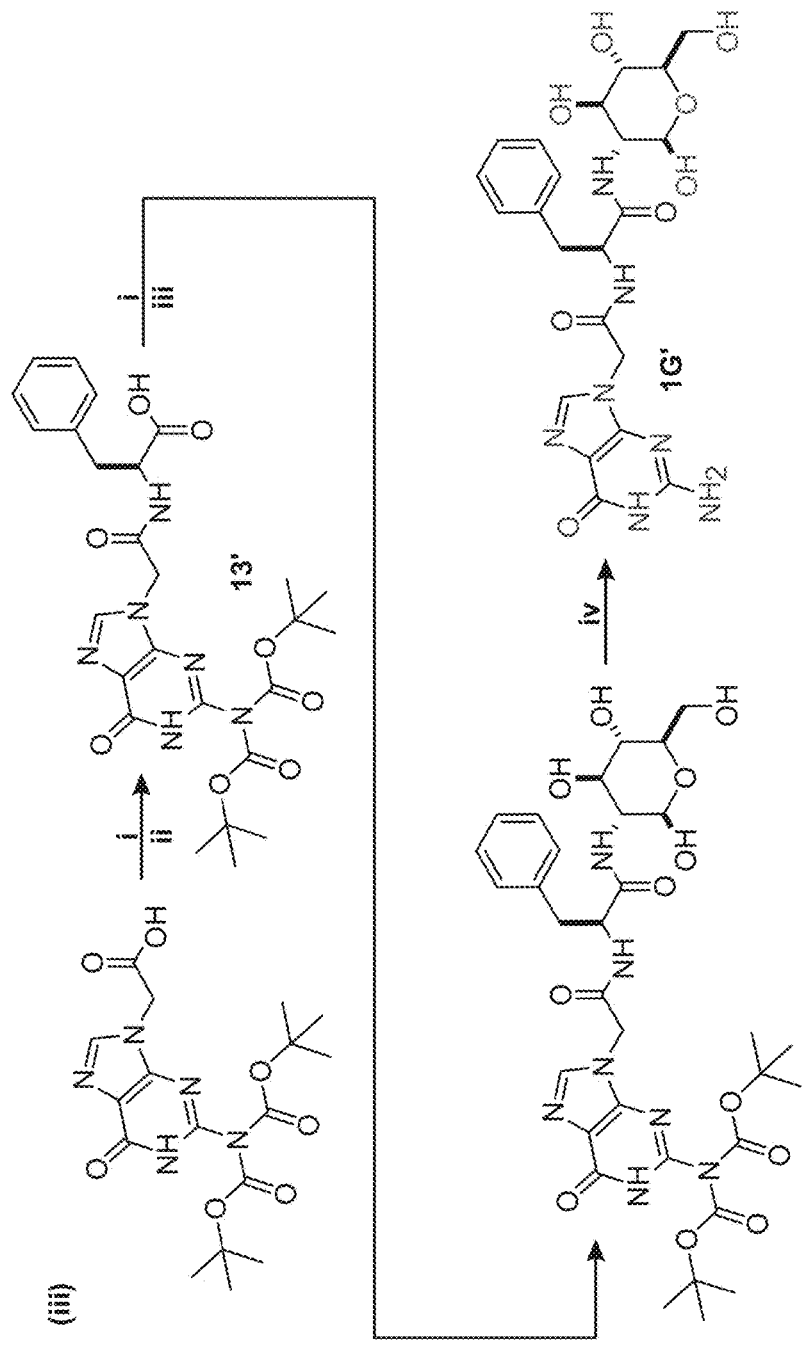
Figure 18F:
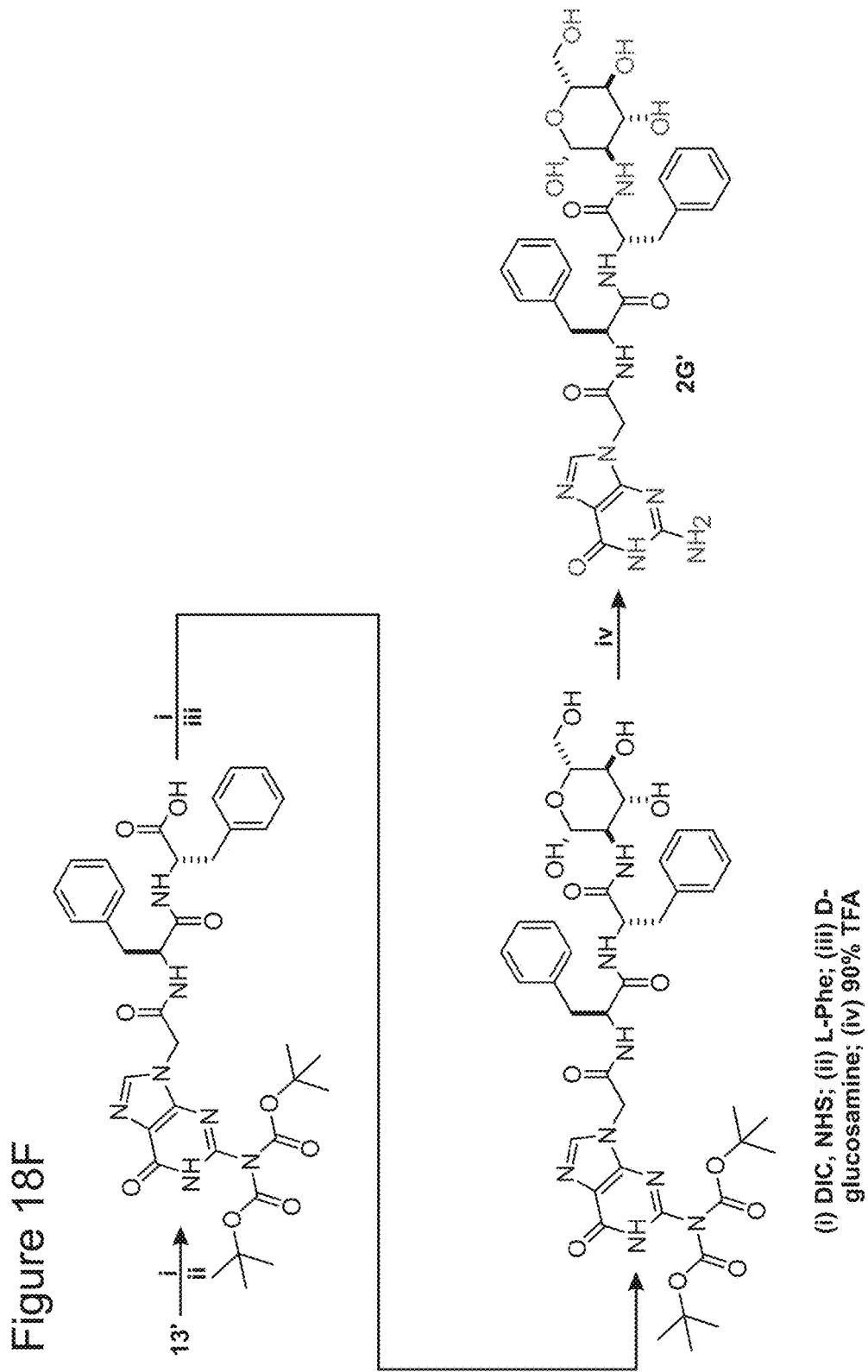
Figure 19:
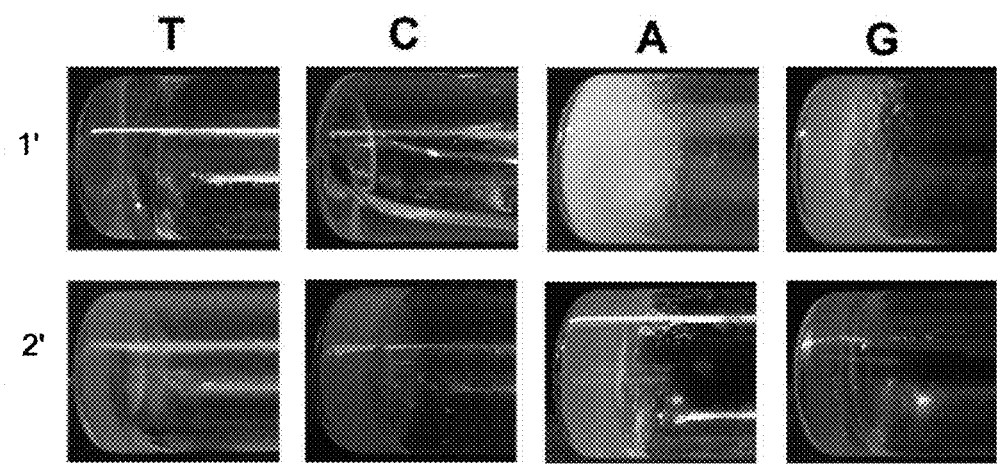
FIG. 19 depicts photographs of the hydrogels of 1T' (3.0 wt %, pH=7.0), 2T' (3.0 wt %, pH=8.5), 2C' (3.0 wt %, pH=7.5), 1A' (3.0 wt %, pH=5.0), 2A' (3.0 wt %, pH=5.0), 1G' (3.0 wt %, pH=4.0) and 2G' (3.0 wt %, pH=4.0); and the solution of 1C' (3.0 wt %, pH=7.0).

FIG. 16 shows the molecular design of two exemplary types of hydrogelators (1' and 2'). Hydrogelator 1' consists of a nucleobase (e.g., thymine, cytosine, adenine, or guanine), a phenylalanine, and a D-glucosamine; hydrogelator 2' consists of a nucleobase, a bis(phenylalanine), and a D-glucosamine. In certain embodiments, the nucleobase and the D-glucosamine connect to the amino acid(s) at the N-terminus and C-terminus, respectively. FIG. 17 outlines an exemplary synthetic route for making these hydrogelators. For example, thymine acetic acid (3') is activated by N-hydroxysuccinimide (NHS) before reacting with L-Phe to afford 4'. After undergoing the same NHS activation, 4' couples with D-glucosamine to give the hydrogelator 1T'. The addition of the second phenylalanine to 4' affords 5', which couples with D-glucosamine to yield the hydrogelator 2T'.

The synthesis of other hydrogelators (i.e., 2C', 1A', 2A', 1G' and 2G') and compound 1C' starts from protected nucleobases (e.g., ($N^4$-bis-Boc-cytosine-1-yl)-acetic acid, ($N^6$-bis-Boc-adenine-9-yl)-acetic acid, and ($N^2$-bis-Boc-guanine-9-yl)-acetic acid). First, bis(tert-butyloxycarbonyl) (bis-Boc) protected adenine, ($N^6$-bis-Boc-adenine-9-yl)-acetic acid (6'), was synthesized. After being activated by NHS, 6' reacts with L-Phe to afford 7', which undergoes the same NHS activation and D-glucosamine coupling to give the product 8'. Subsequent removal of the Boc-protecting groups by the addition of trifluoroacetic acid (TFA) gives the hydrogelator 1A' in 42% total yield. The addition of the second phenylalanine to the compound 7' gives 9', which reacts with D-glucosamine to afford intermediate 10'. After the Boc groups being removed, 10' turns into hydrogelator 2A'. This five-step synthesis affords 2A' in 37% total yield. Based on the same strategy, we obtain 1C', 2C', 1G', and 2G' in 45%, 39%, 41%, and 43% total yields, respectively.

In certain embodiments, protonation and deprotonation of an amine group may be used to dissolve any one of the aforementioned hydrogelators at low pH. In certain embodiments, hydrogelation may be triggered by increasing the pH. In certain embodiments, the hydrogelators dissolve in water at about 3.0 wt % and pH of about 10.0. In certain embodiments, the hydrogelators dissolve in water at about 3.0 wt % and pH of about 10.0 with gentle heating. In fact, changing the pH values of the solutions of 1T' and 2T' from 10.0 to 7.0 and 8.5, respectively, results in transparent hydrogels. The mixture containing 1C', however, remains as a solution at the same conditions. The increase of the pH value of the solution of 1C' up to pH 10.0 only results in a small amount of white precipitate. While 1A' forms an opaque hydrogel at pH 5.0, 1G' produces a semitransparent hydrogel at pH 4.0. Hydrogelators 2T', 2C', 2A' and 2G' all are able to self-assemble in water to form semitransparent hydrogels at a concentration of about 3.0 wt % and a pH of about 8.5, 7.5, 5.0 and 4.0, respectively. The different optical appearances of the hydrogels and the final pH for hydrogelation suggest subtle differences in solubility for these hydrogelators.

Figure 20:
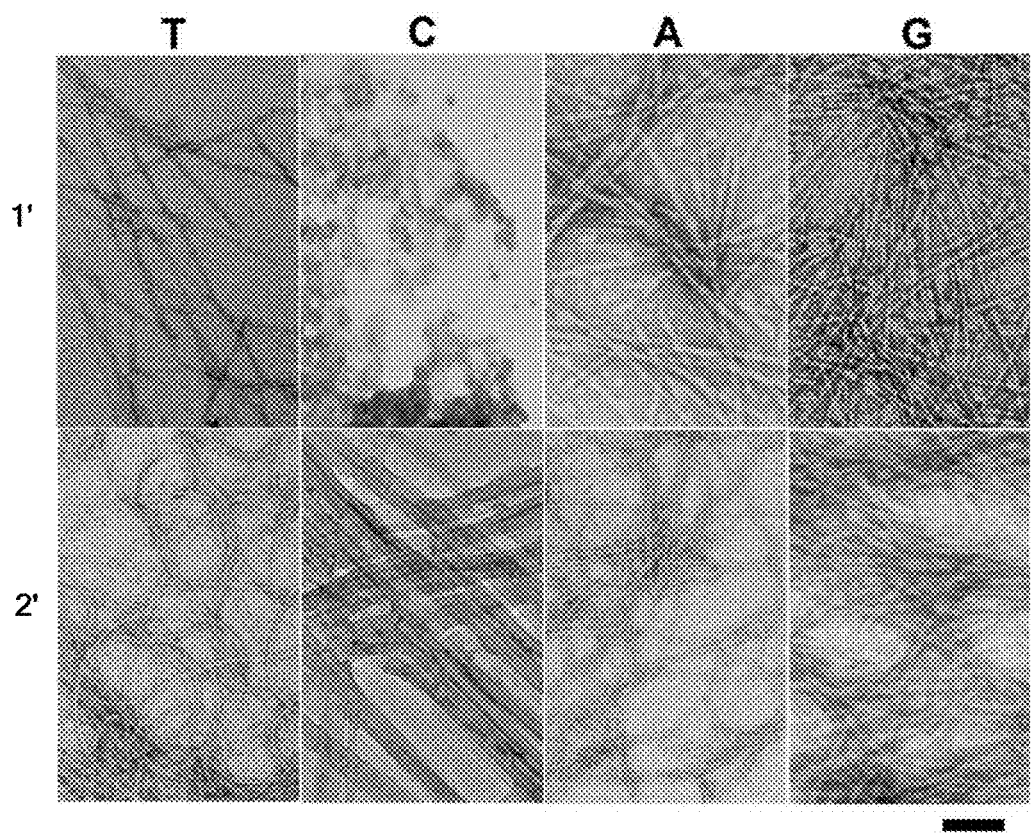
FIG. 20 depicts transmission electron micrographs of negative stained hydrogels of 1T', 2T', 2C', 1A', 2A', 1G' and 2G'; and solution of 1C'. Scale bar=100 nm; the concentration and pH value for each of them are same as in FIG. 19.
Figure 21:
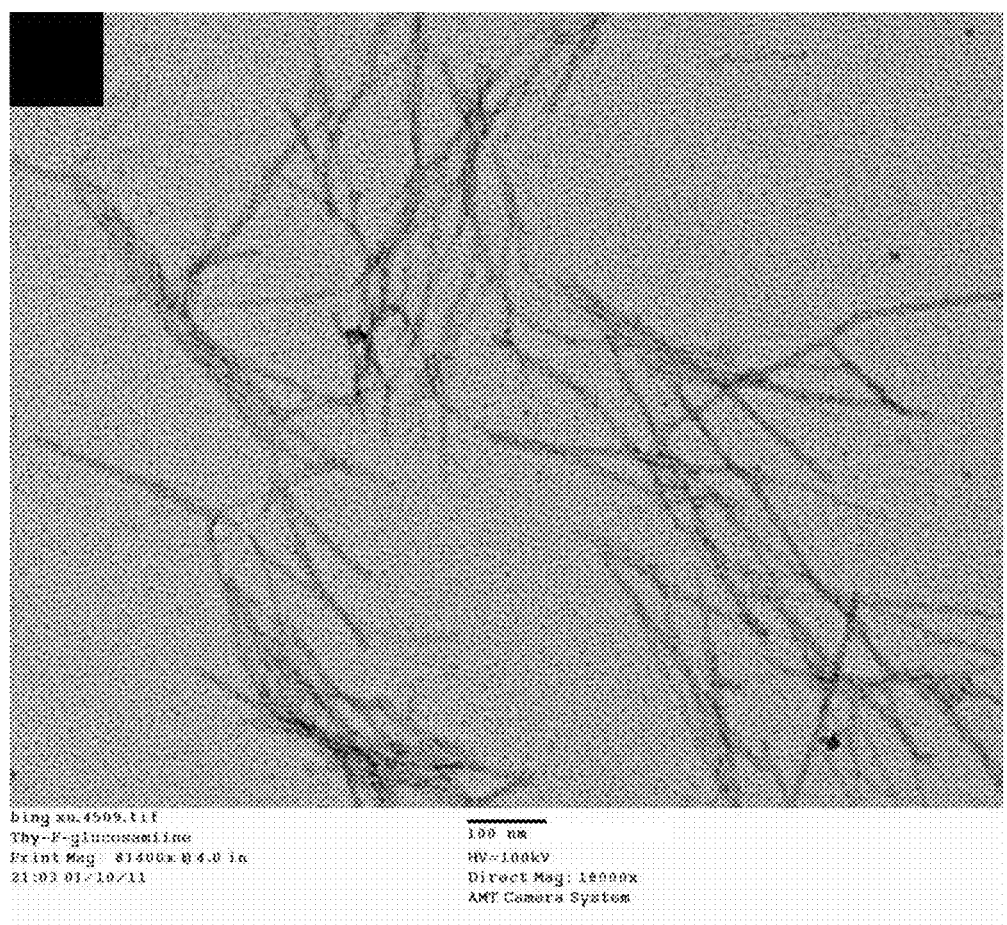
FIG. 21 depicts transmission electron micrographs of hydrogels of (a) 1T' and (b) 2T'.
Figure 21:
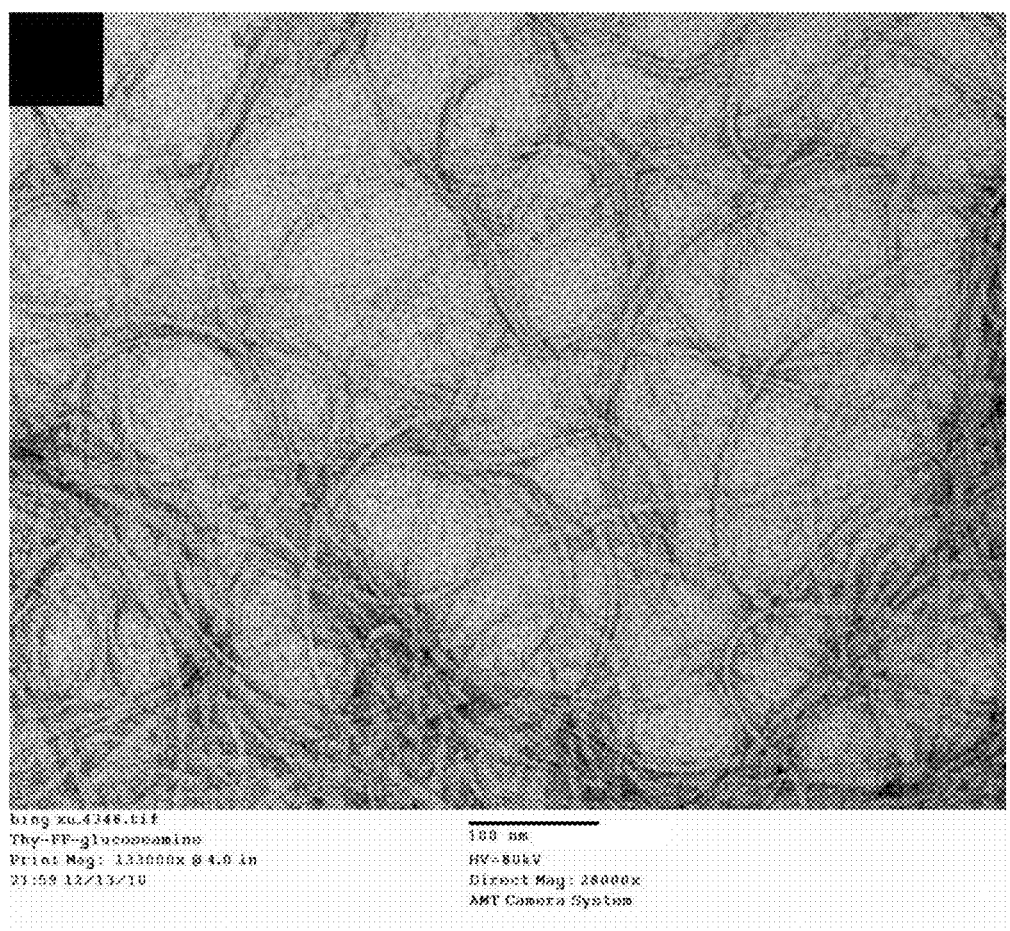
Figure 22:
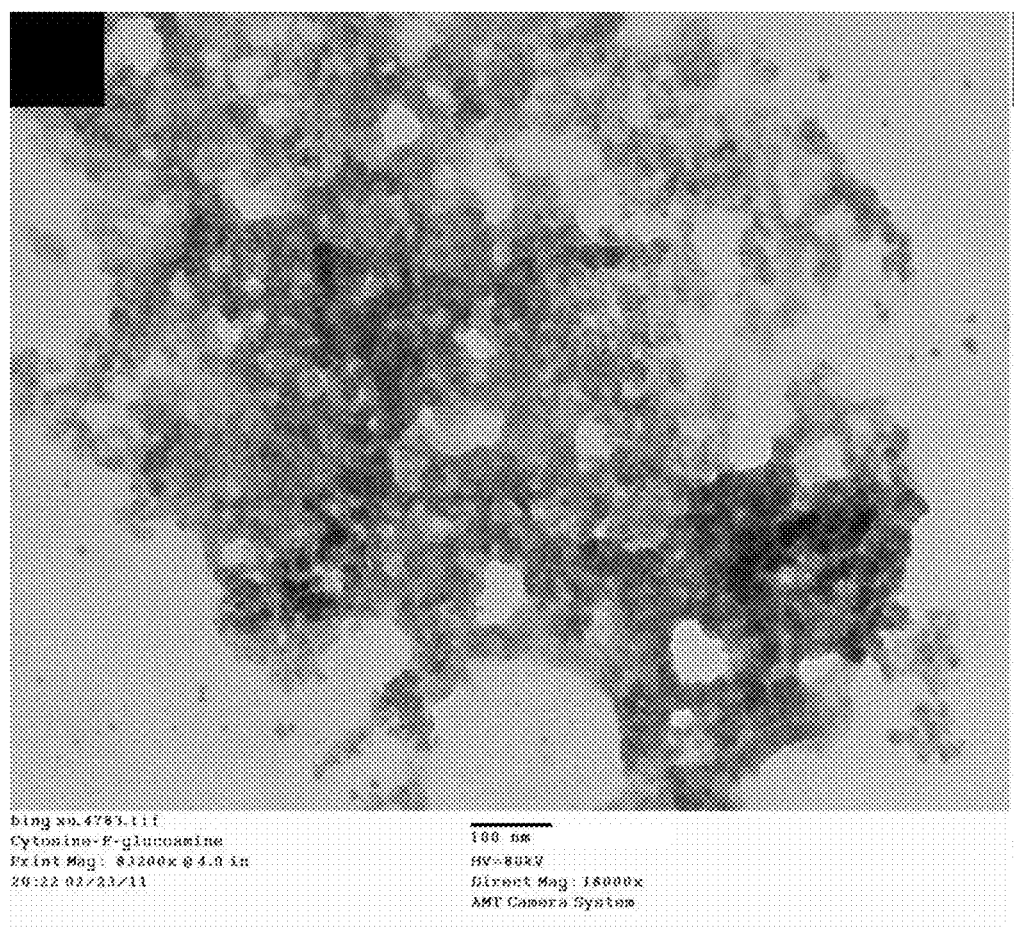
FIG. 22 depicts transmission electron micrographs of (a) the solution of 1C' and (b) the hydrogel of 2C'.
Figure 22:
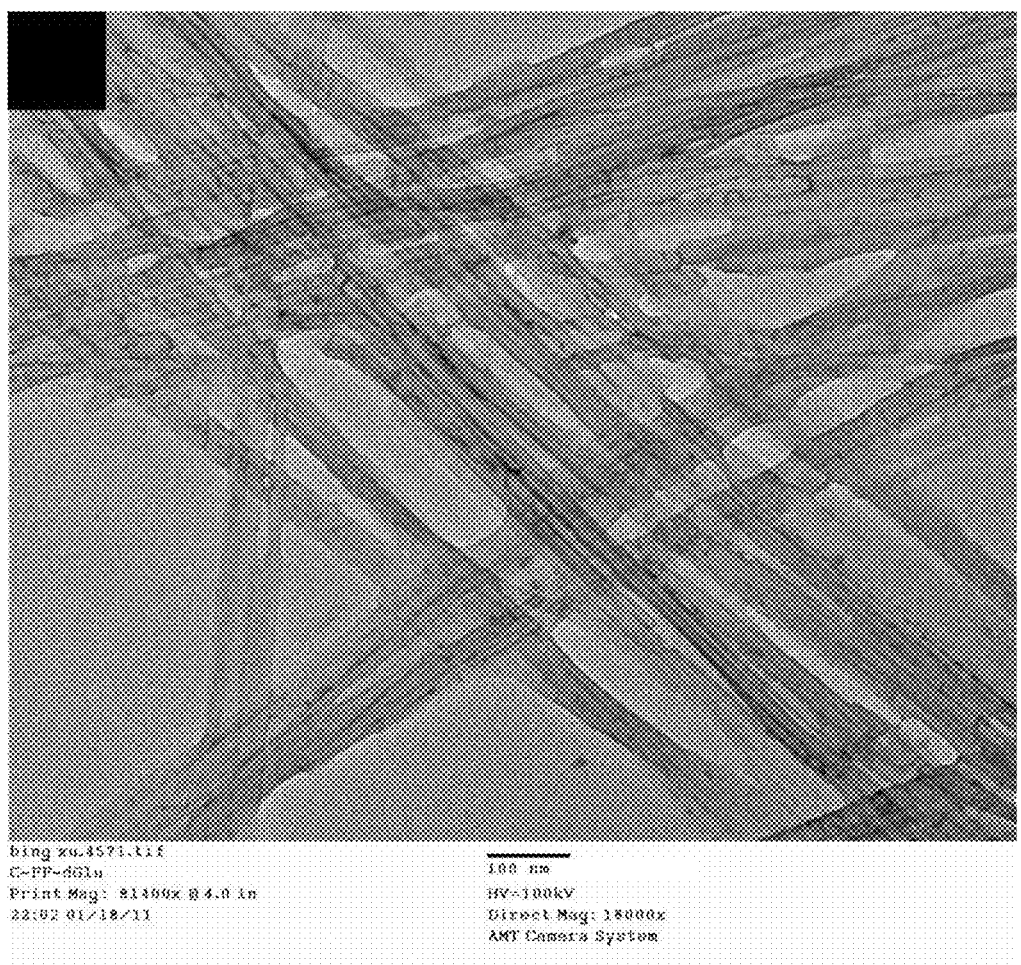
Figure 23:
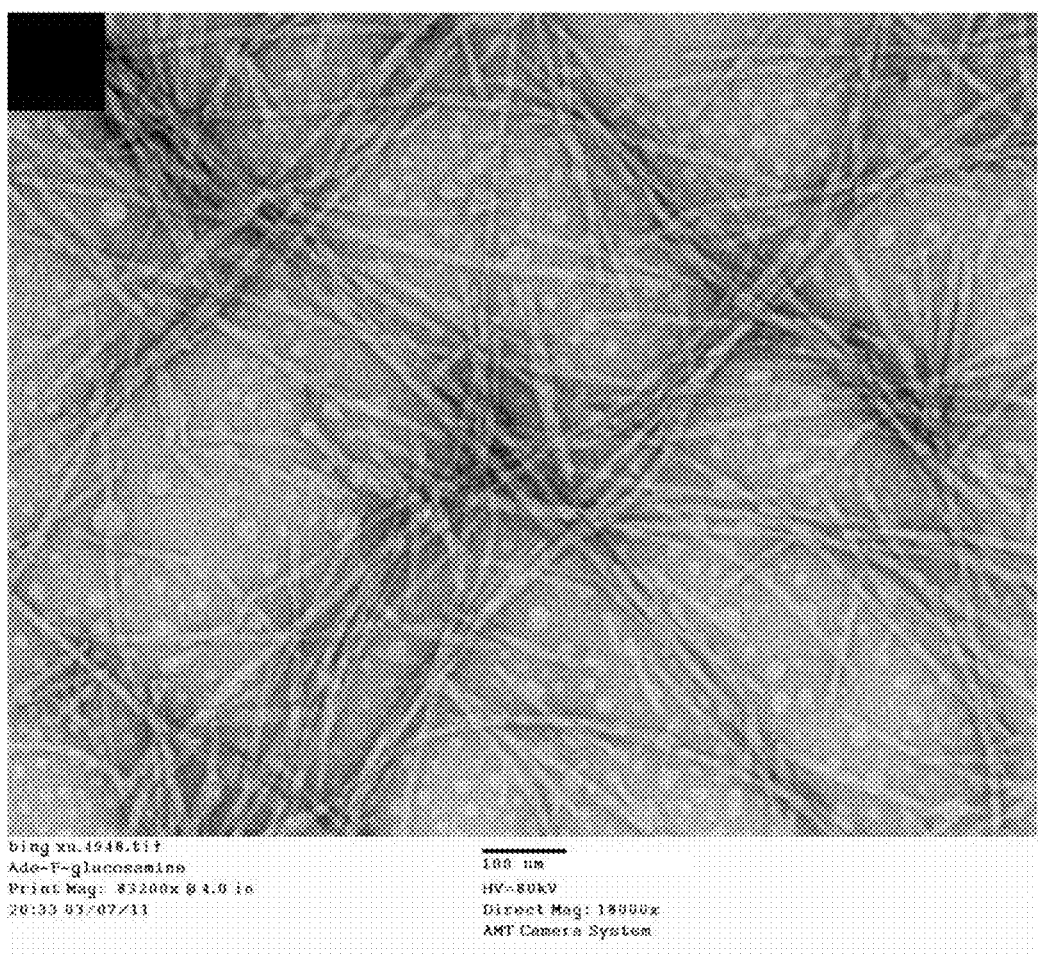
FIG. 23 depicts transmission electron micrographs of hydrogels of (a) 1A' and (b) 2A'.
Figure 23:
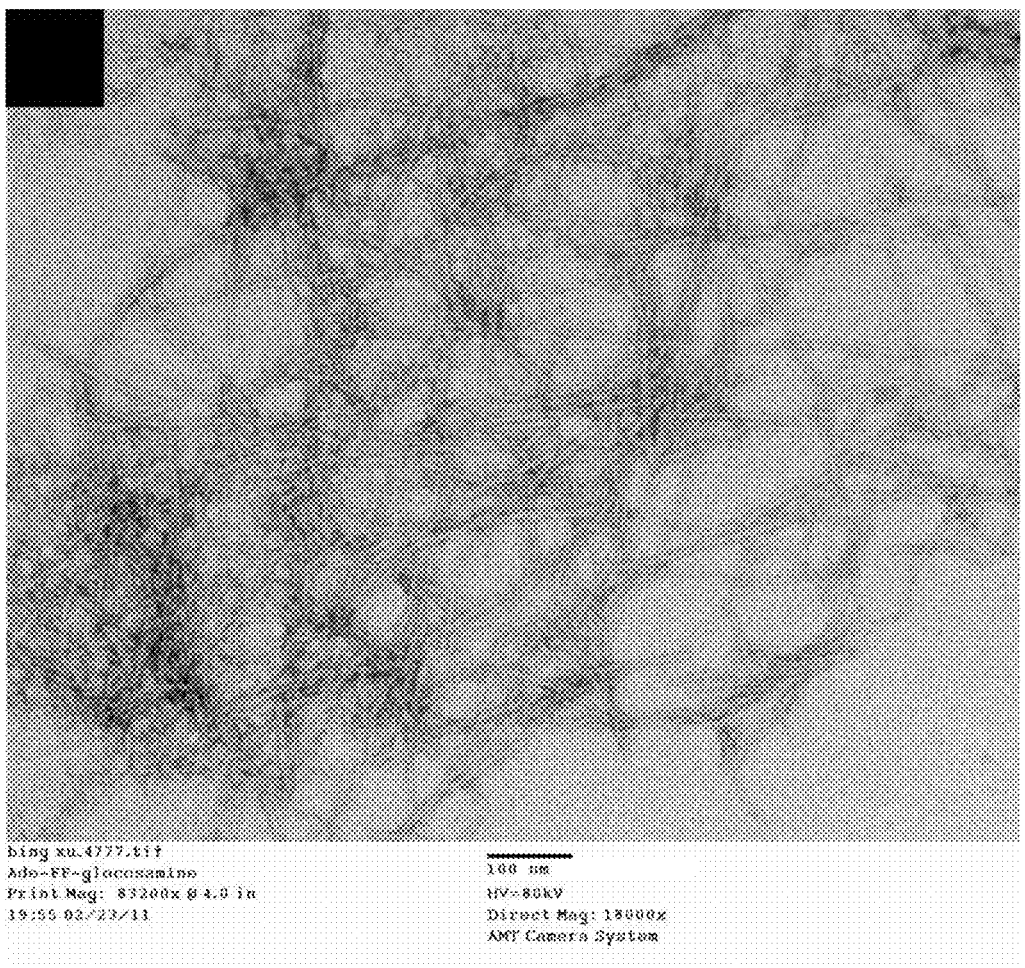
Figure 24:
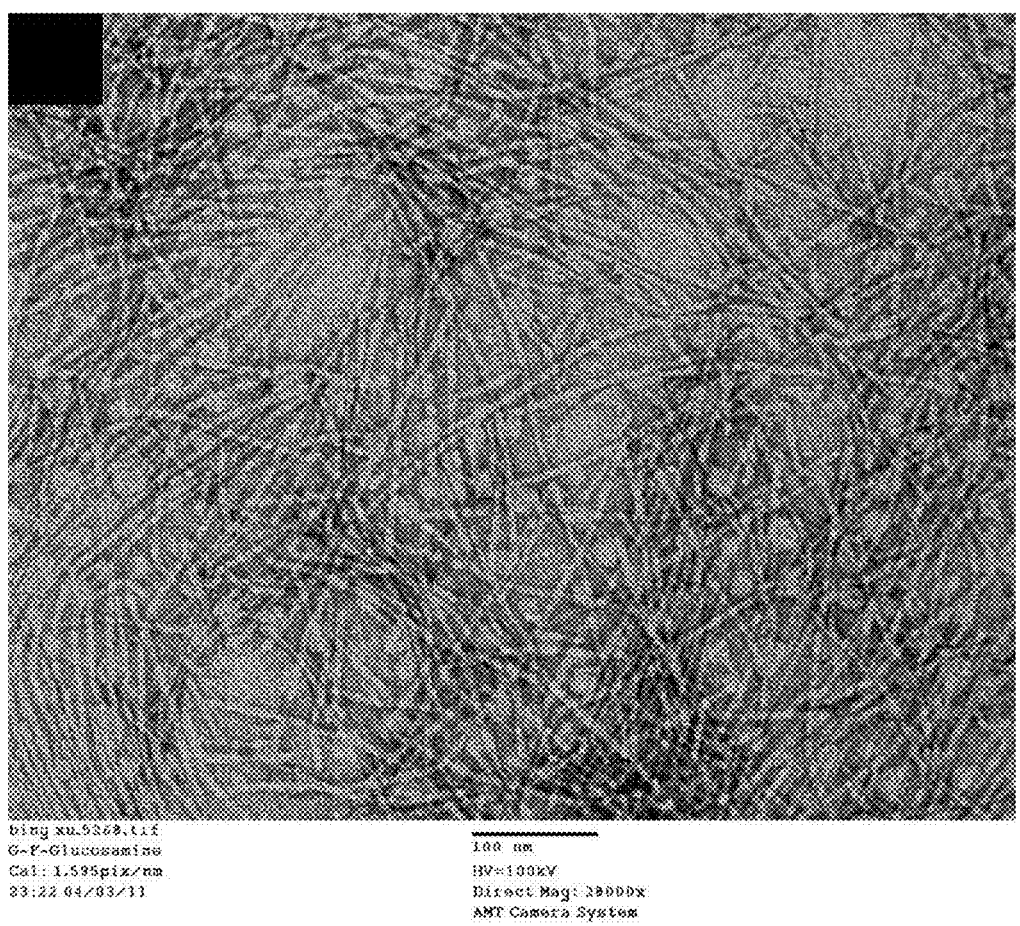
FIG. 24 depicts transmission electron micrographs of hydrogels of (a) 1G' and (b) 2G'.
Figure 24:
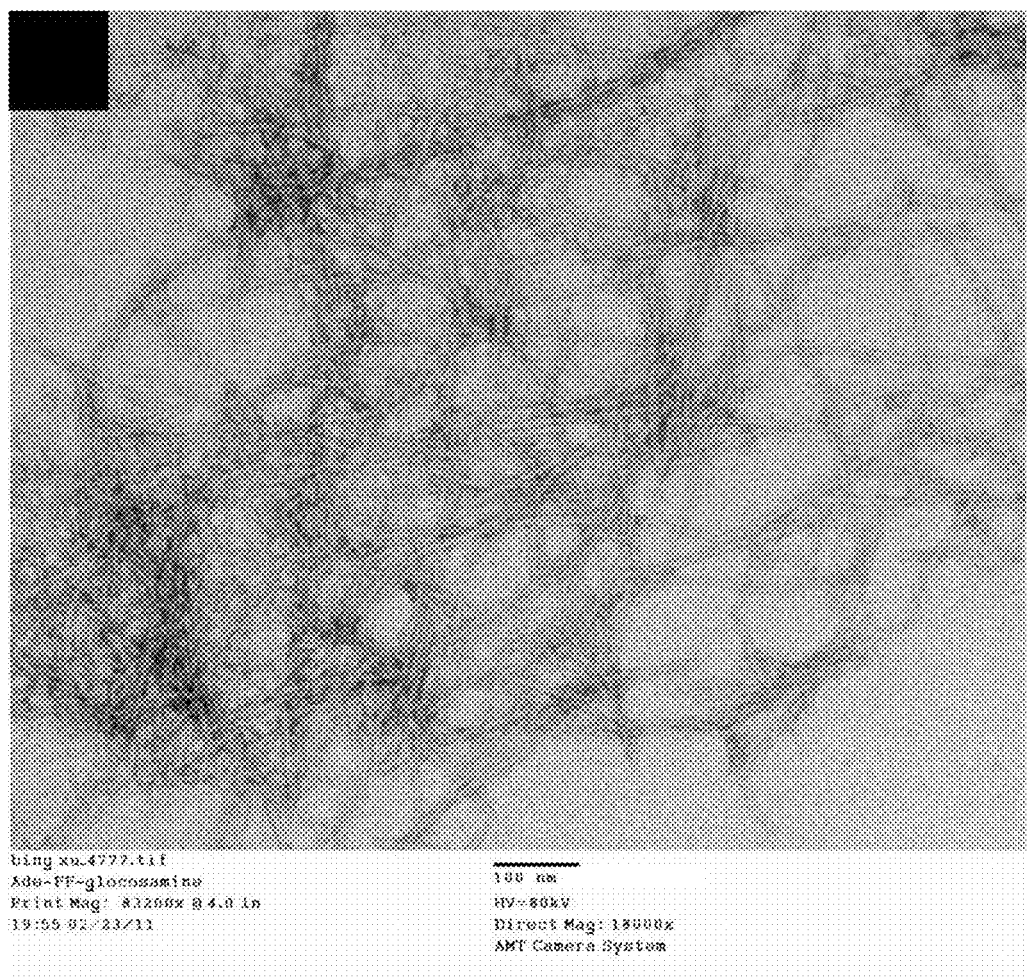

Transmission electron microscopy (TEM) was used to examine the microstructures of the matrices of the hydrogels formed by these hydrogelators. As revealed by TEM in FIG. 20, each hydrogelator exhibits distinctive morphology of the nanostructures in the corresponding hydrogels. For example, while the nanofibers of 1T' are thin and straight and with the diameter of about 12 nm, the nanofibers of 2T' (about 15 nm in diameter) appear to bend easily and to crosslink relatively heavily. The solution of 1C' only results in featureless aggregates, likely due to non-specific absorption of the 1C' on the carbon film of TEM grid. The hydrogel of 2C' consists of nanobelts (about 25 nm wide) that physically crosslink into networks. The nanofibers of 2C' also form bundles that likely contribute to the high storage modulus (FIG. 26B). While both short nanofibers (14 nm in width and 200 nm in length) and nanoparticles (average diameter of 18 nm) present as the solid phase in the hydrogel of 1A', the hydrogel of 2A' exhibits only nanofibers, which tend to crosslink physically to afford the network. The hydrogel of 1G' appears to comprise thin nanofibers (9 nm in width) and aggregated nanoparticles whose diameters are about 27 nm. Hydrogelator 2G' self-assembles in water to form long thin nanofibers with a width of about 13 nm, and the nanofibers in 2G' entangle with each other to form a dense nanofiber network, which also contributes to its relatively high storage modulus (FIG. 26B).

Because hydrogels are viscoelastic they resist external destruction. Rheometry was used to study the viscoelastic properties of the instant hydrogels and to evaluate their critical strains and storage moduli (G'). Based on the results from the strain sweep (FIG. 25), the hydrogel of 1T' shows the highest tolerance to external shear force with critical strain value at 0.5% (FIG. 26A). The critical strain values of the hydrogels of 1A', 1G', 2T', 2C', 2A', and 2G' are at 0.23, 0.28, 0.31, 0.27, 0.39, and 0.18%, respectively, suggesting that the networks in these hydrogels lose their integrity relatively easily upon application of external force. The frequency sweep shows that the dynamic storage moduli (G') of the hydrogels (1T', 2T', 2C', 1A', 2A', 1G' and 2G') dominate their dynamic loss moduli (G") (FIG. 25), indicating that all samples behave as viscoelastic materials. Among these hydrogels, the hydrogel of 2C' exhibits the highest storage modulus (220 KPa). The hydrogels of 1G', 2G', 1T', 2T', and 1A' possess relatively high storage moduli of 139, 101, 34, 32, and 6 KPa, respectively. The hydrogel of 2A' exhibits the lowest storage modulus (0.37 KPa), likely due to the short constituent nanofibers and nanoparticles, which disfavour the formation of crosslinked network.

Figure 25:
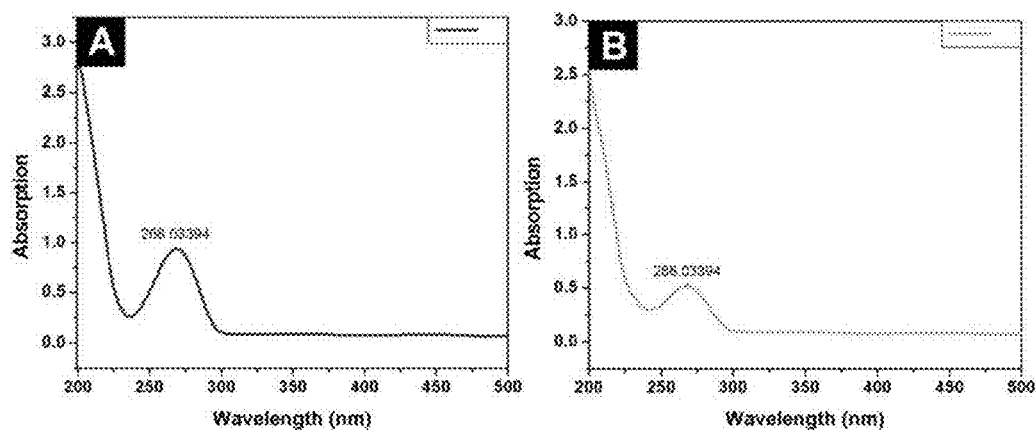
FIG. 25 depicts the UV-vis absorption spectrum of: (A) 1T' in aqueous solution (c=6.0×10$^{-4}$ M); and (B) 2T' in aqueous solution (c=3.0×10$^{-4}$ M); the data indicate there is no chromophoric absorption around 296 nm in the solutions.
Figure 26:
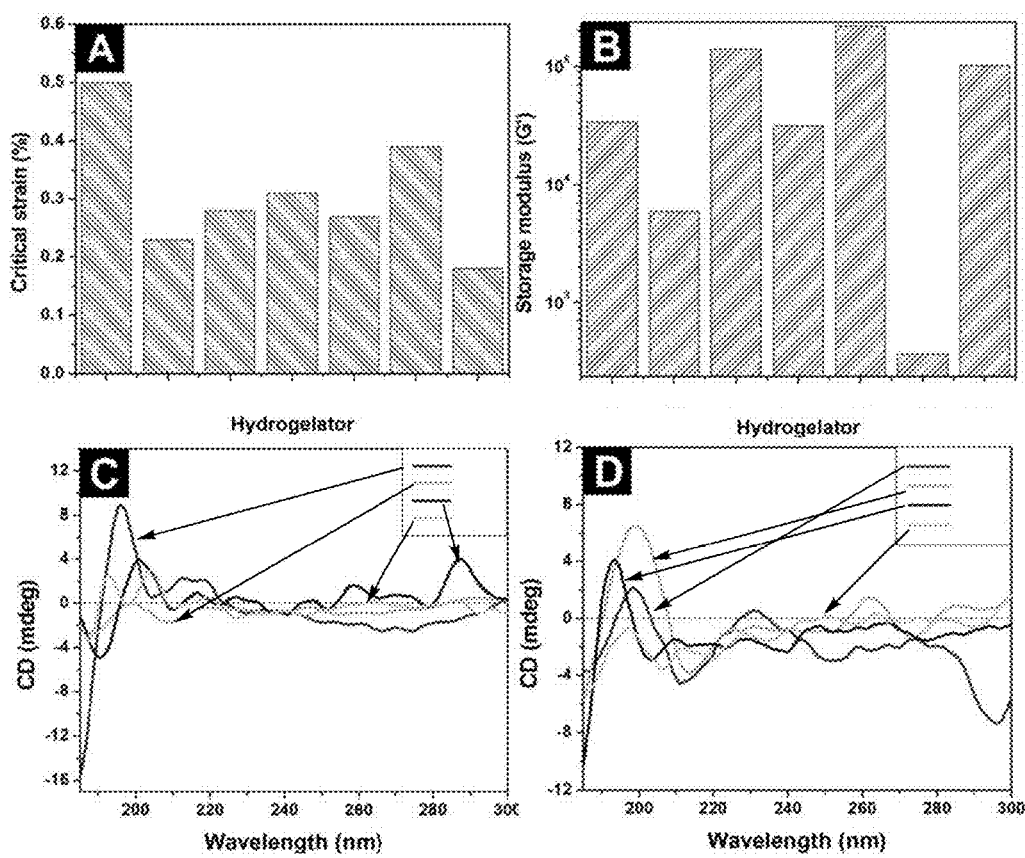
FIG. 26 depicts (A) the critical strain of hydrogels (from left to right: 1T', 1A', 1G', 2T', 2C', 2A', 2G'), and (B) dynamic storage moduli (G') of hydrogels (from left to right: 1T', 1A', 1G', 2T', 2C', 2A', and 2G'; (C) CD spectra (from top to bottom in key: 1T' gel, 1C' solution, 1A' gel, 1G' gel); (D) CD spectra (from top to bottom in key: 2T' gel, 2C' gel, 2A' gel, and 2G' gel). The concentration and pH value for each of them are same as for FIG. 19.
Figure 27:
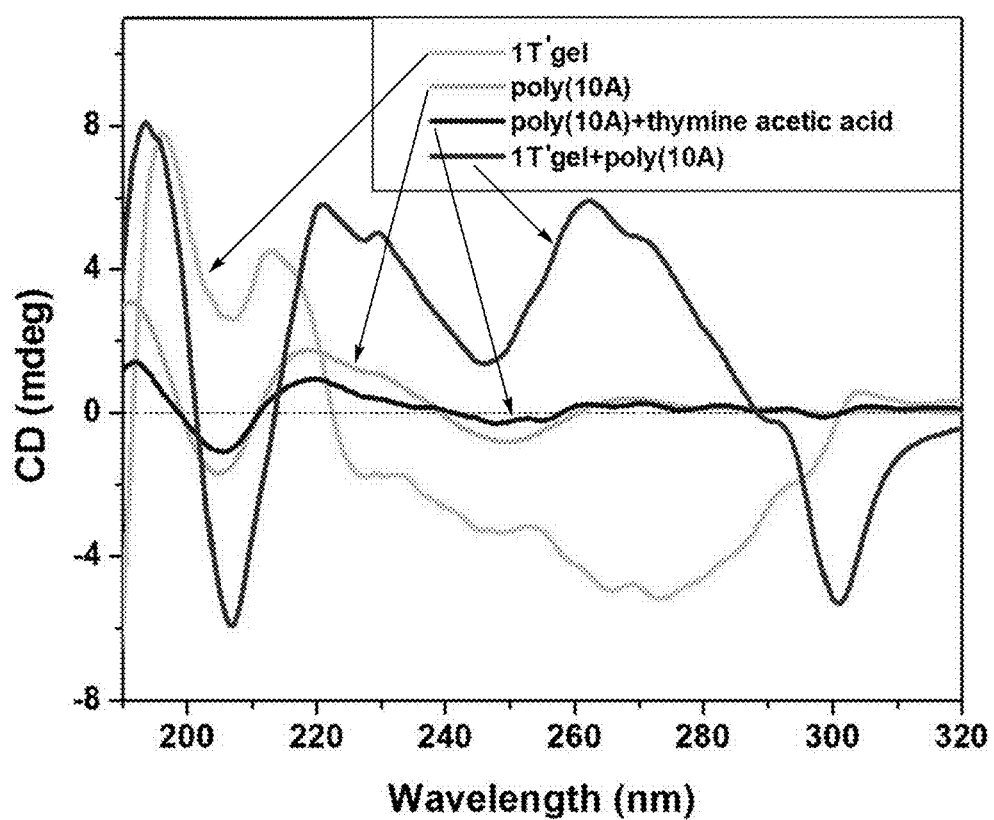
FIG. 27 depicts the circular dichroism (CD) spectra of the hydrogel of 1T', the solution of poly(10A), the mixture solution of thymine acetic acid with poly(10A) in 1:1 molecular ratio, and the hydrogel of 1T' mixed with poly(10A) in 1:1 molecular ratio.

Circular dichroism (CD) spectroscopy provides helpful information about self-assembled superstructures in the gel phase or liquid crystal phases. Thus, we used circular dichroism (CD) to study the secondary structures of nanofibers self-assembled from different compounds in the gel phase. As shown in FIG. 26, hydrogels of 1T', 2T', 2C', 2A', 2G' all exhibit a positive peak near 195 nm and a negative peak around 210 nm, suggesting that the backbones of the hydrogelators adopt β-sheet-like configurations in the self-assembled structures. The CD spectrum of the hydrogel of 2T' shows a negative broad band around 296 nm, which likely originates from the formation of a mesophase of 2T' because it locates far from the chromophoric absorption region (ca. 268 nm) of compound 2T' (FIG. 25). The CD spectra of hydrogels of 1A' and 1G' display a maximum around 201 nm and a minimum near 210 nm, slightly red-shifted from the maxima and minima found in typical β-sheets, indicating that the supramolecular structures share the common feature of a β-sheet structure, but in a less ordered conformation or in a mixture of β-sheet and random coil structures. The solution of 1C' exhibits the weakest CD absorptions, agreeing with the poor tendency for compound 1C' to self-assemble in water to form ordered structures.

Figure 29A:
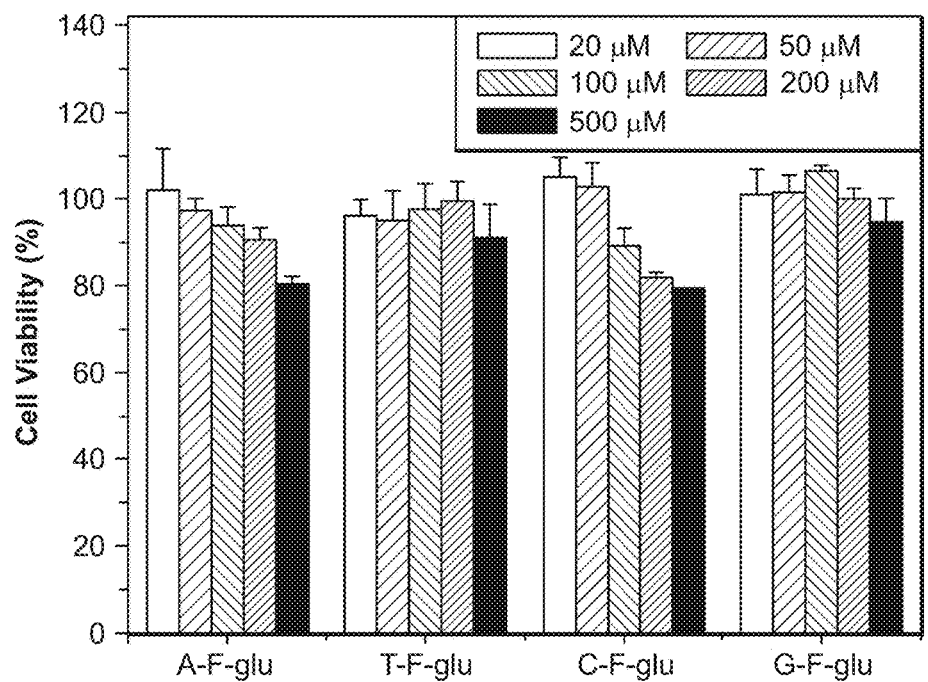
FIG. 29 depicts 72 hr cell viability test of (A) hydrogelator 1', and (B) hydrogelator 2'; optical images of the scratch-wound assay to assess the effects of 2T' in the media on wound closure; optical images of HeLa cells on the surface at 0 h (C); and at 20 h (D) after the creation of wound in the presence of 2T' (by adding 500 μM of 2T' in the media); and (E) the time-dependent course of digestions of hydrogelators of 2T', 2C', 2A' and 2G' by proteinase K.
Figure 29B:
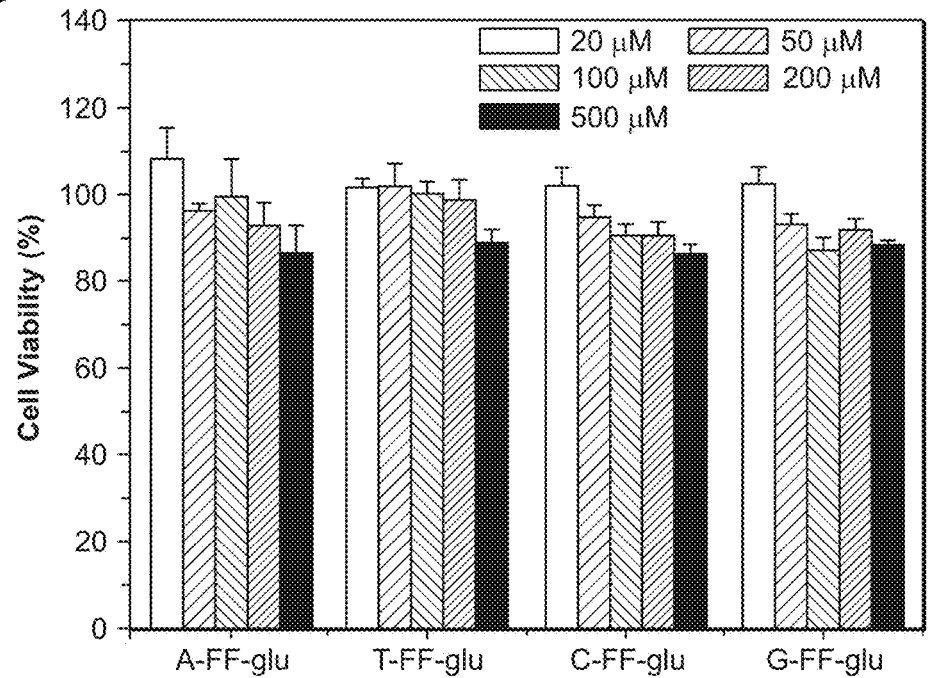
Figure 29C:
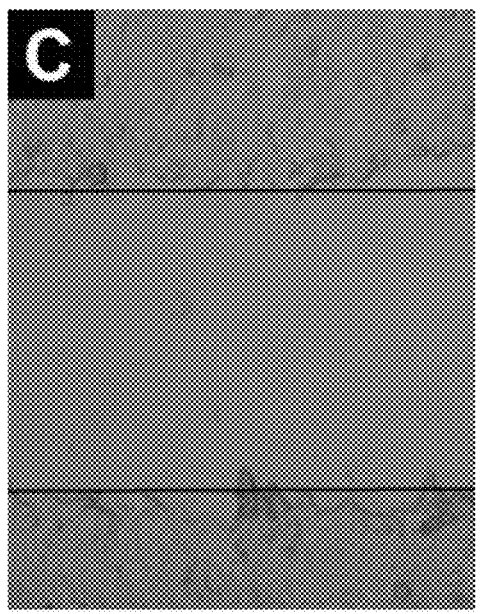
Figure 29D:
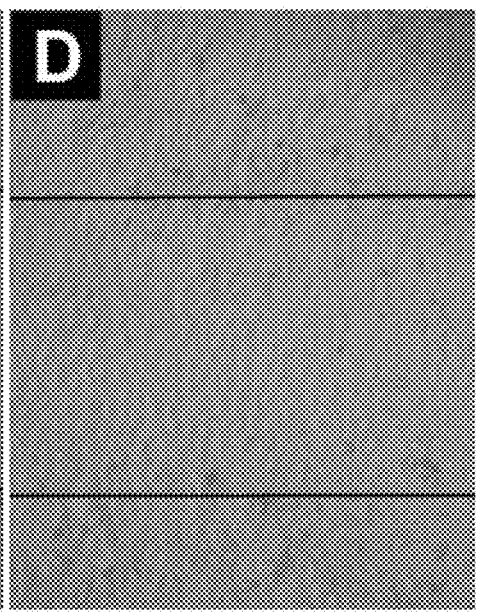

To verify the biocompatibility of the hydrogelators, hydrogelators 1' and 2' were added into a culture of mammalian cells, and the proliferation of the cells was measured. MTT assay results, shown in FIG. 29A and FIG. 29B, revealed cell viability remained at 90% after incubation with 500 μM hydrogelator (1T', 1G', 2T', 2C', 2A', 2G') for 72 hours. Although the cell viability decreased slightly when the cells were incubated with 500 μM of 1C' or 1A' for 72 hours, the value of $IC_{50}$ is still >500 μM. These results suggest that hydrogelators 1' and 2' are biocompatible. In order to further examine the biocompatibility of the hydrogelators, we also conducted a simple wound-healing assay with hydrogelator 1T'. As shown in FIG. 29D, the presence of the hydrogelator of 1T' in cell culture has little inhibitory effect on the migration of cells.

Figure 29E:
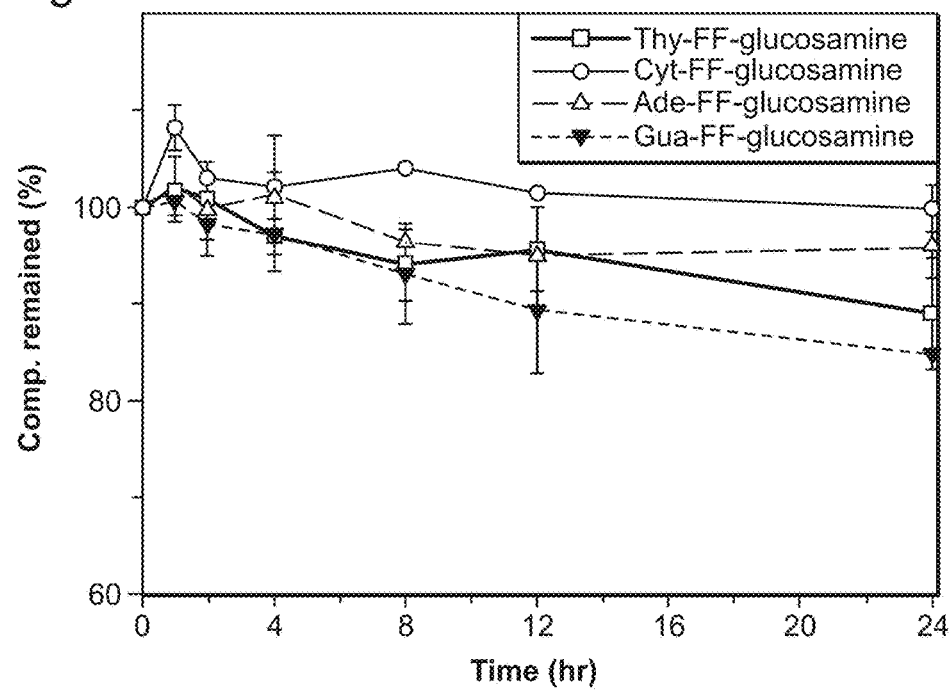
Figure 30:
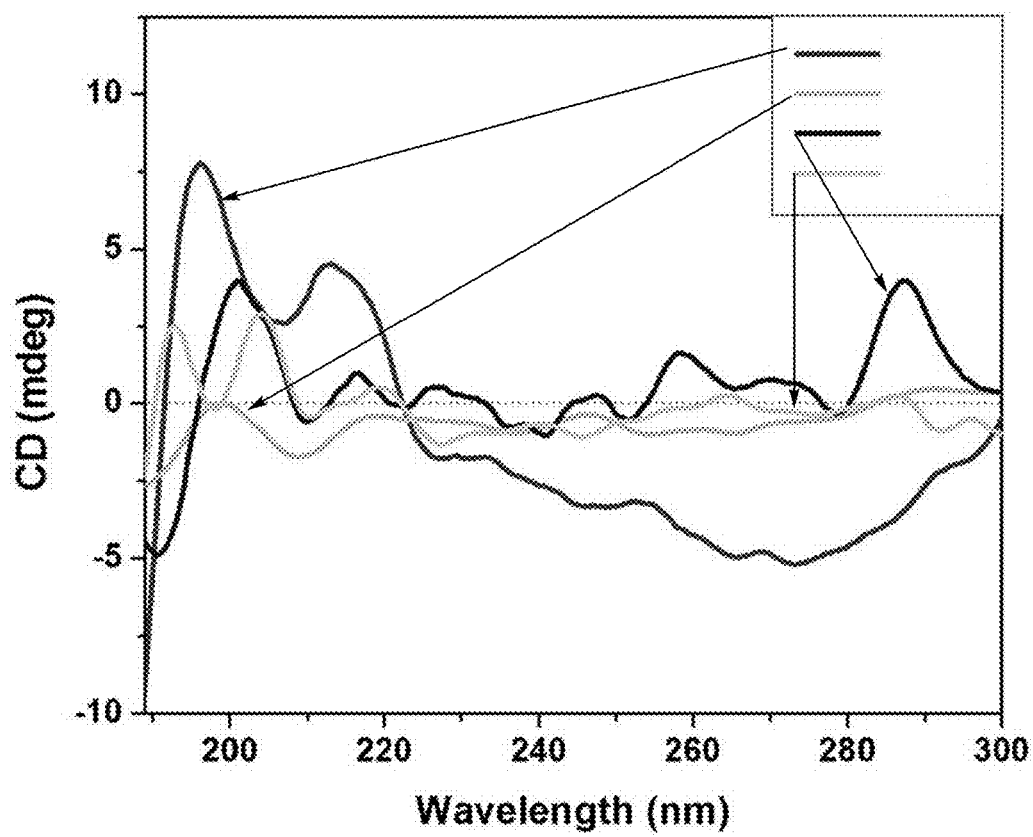
FIG. 30 depicts the CD spectra of the hydrogels of (from top to bottom in key: 1T' gel, 1C' solution, 1A' gel, and 1G' gel.

Besides biocompatibility, biostability is also an essential prerequisite for a biomaterial. Thus, we examined the stability of hydrogelators 2' by incubating them with proteinase K, a powerful protease that hydrolyzes a broad spectrum of peptides. As shown in FIG. 29E, hydrogelators 2' exhibit excellent resistance to enzymatic digestion, indicated by more than 85% of 2T' and 2G' and 95% of 2C' and 2A' remaining intact after 24 hours of incubation. Due to their high resistance to proteases, the hydrogels formed by hydrogelators 2' promise to serve as new biomaterials for applications that require long-term biostability.

Exemplary Glycoside-Containing Hydrogelators of the Invention

In certain embodiments, the invention relates to a hydrogelator of Formula I(b)

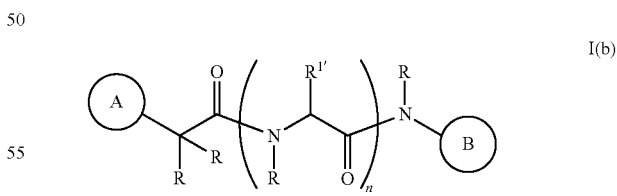

wherein, independently for each occurrence,

is cytosinyl, guaninyl, adeninyl, thyminyl, uracilyl, or an oligonucleic acid;

is fructosyl, galactosyl, glucosyl, mannosyl, or an oligosaccharide;

R is H or alkyl;

$R^{1'}$ is H, alkyl, alkylthioalkyl, aralkyl, heteroaralkyl, hydroxyaralkyl, $HO_2C$-alkyl, or guanidinylalkyl; and n is 1, 2, 3, 4, 5, 6, 7, 8, 9, 10, 11, 12, 13, 14, 15, 16, 17, 18, 19, or 20.

In certain embodiments, the invention relates to any one of the aforementioned hydrogelators, wherein

is cytosinyl. In certain embodiments, the invention relates to any one of the aforementioned hydrogelators, wherein

is guaninyl In certain embodiments, the invention relates to any one of the aforementioned hydrogelators, wherein

is adeninyl. In certain embodiments, the invention relates to any one of the aforementioned hydrogelators, wherein

is thyminyl. In certain embodiments, the invention relates to any one of the aforementioned hydrogelators, wherein

is uracilyl. In certain embodiments, the invention relates to any one of the aforementioned hydrogelators, wherein

is an oligonucleic acid.

In certain embodiments, the invention relates to any one of the aforementioned hydrogelators, wherein

is glucosyl. In certain embodiments, the invention relates to any one of the aforementioned hydrogelators, wherein

is an oligosaccharide. In certain embodiments, the invention relates to any one of the aforementioned hydrogelators, wherein

is chondrosinyl.

In certain embodiments, the invention relates to any one of the aforementioned hydrogelators, wherein R is H.

In certain embodiments, the invention relates to any one of the aforementioned hydrogelators, wherein $R^{1'}$ is H.

In certain embodiments, the invention relates to any one of the aforementioned hydrogelators, wherein $R^{1'}$ is alkyl. In certain embodiments, the invention relates to any one of the aforementioned hydrogelators, wherein $R^{1'}$ is methyl. In certain embodiments, the invention relates to any one of the aforementioned hydrogelators, wherein $R^{1'}$ is ethyl. In certain embodiments, the invention relates to any one of the aforementioned hydrogelators, wherein $R^{1'}$ is propyl. In certain embodiments, the invention relates to any one of the aforementioned hydrogelators, wherein $R^{1'}$ is isopropyl. In certain embodiments, the invention relates to any one of the aforementioned hydrogelators, wherein $R^{1'}$ is butyl. In certain embodiments, the invention relates to any one of the aforementioned hydrogelators, wherein $R^{1'}$ is isobutyl. In certain embodiments, the invention relates to any one of the aforementioned hydrogelators, wherein $R^{1'}$ is sec-butyl.

In certain embodiments, the invention relates to any one of the aforementioned hydrogelators, wherein $R^{1'}$ is alkylthioalkyl. In certain embodiments, the invention relates to any one of the aforementioned hydrogelators, wherein $R^{1'}$ is $CH_3$—S—$CH_2CH_2$—.

In certain embodiments, the invention relates to any one of the aforementioned hydrogelators, wherein $R^{1'}$ is aralkyl. In certain embodiments, the invention relates to any one of the aforementioned hydrogelators, wherein $R^{1'}$ is benzyl.

In certain embodiments, the invention relates to any one of the aforementioned hydrogelators, wherein $R^{1'}$ is heteroaralkyl. In certain embodiments, the invention relates to any one of the aforementioned hydrogelators, wherein $R^{1'}$ is indolyl-$CH_2$—. In certain embodiments, the invention relates to any one of the aforementioned hydrogelators, wherein $R^{1'}$ is

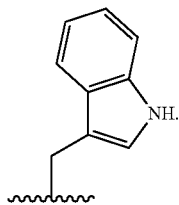 [SMILES: *Cc1c[nH]c2ccccc12]

In certain embodiments, the invention relates to any one of the aforementioned hydrogelators, wherein $R^{1'}$ is hydroxyaralkyl. In certain embodiments, the invention relates to any one of the aforementioned hydrogelators, wherein $R^{1'}$ is hydroxybenzyl. In certain embodiments, the invention relates to any one of the aforementioned hydrogelators, wherein $R^{1'}$ is 4-hydroxybenzyl.

In certain embodiments, the invention relates to any one of the aforementioned hydrogelators, wherein $R^{1'}$ is $HO_2C$-alkyl. In certain embodiments, the invention relates to any one of the aforementioned hydrogelators, wherein $R^{1'}$ is $HO_2C-CH_2-$.

In certain embodiments, the invention relates to any one of the aforementioned hydrogelators, wherein $R^{1'}$ is guanidinylalkyl. In certain embodiments, the invention relates to any one of the aforementioned hydrogelators, wherein $R^{1'}$ is guanidinyl-$CH_2CH_2CH_2-$.

In certain embodiments, the invention relates to any one of the aforementioned hydrogelators, wherein n is 1. In certain embodiments, the invention relates to any one of the aforementioned hydrogelators, wherein n is 2. In certain embodiments, the invention relates to any one of the aforementioned hydrogelators, wherein n is 3. In certain embodiments, the invention relates to any one of the aforementioned hydrogelators, wherein n is 4. In certain embodiments, the invention relates to any one of the aforementioned hydrogelators, wherein n is 5.

In certain embodiments, the invention relates to a compound selected from the group consisting of:

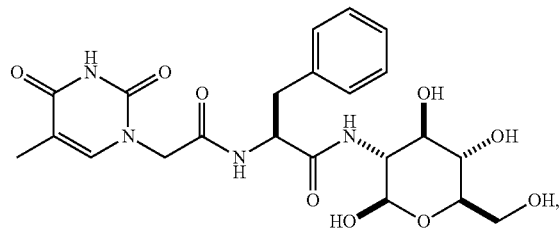

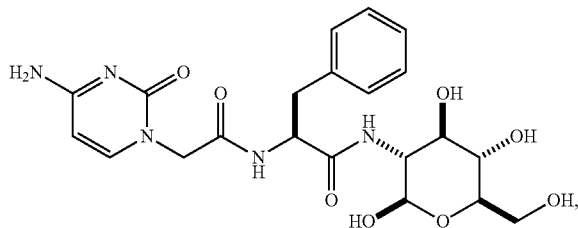

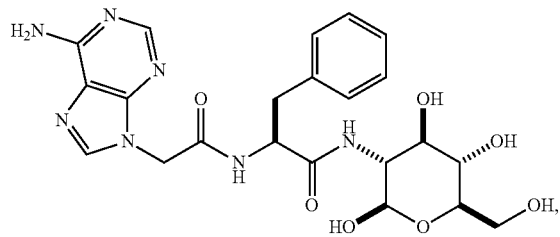

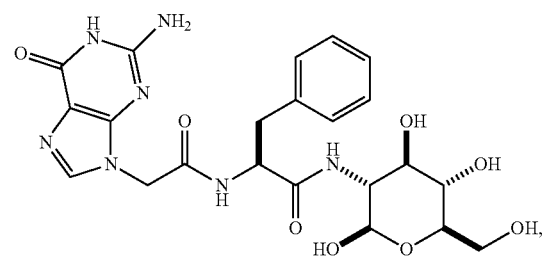

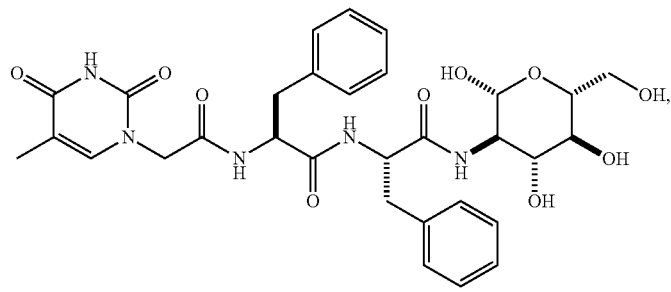

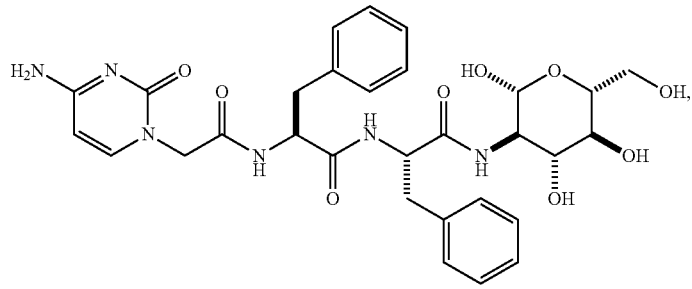

-continued
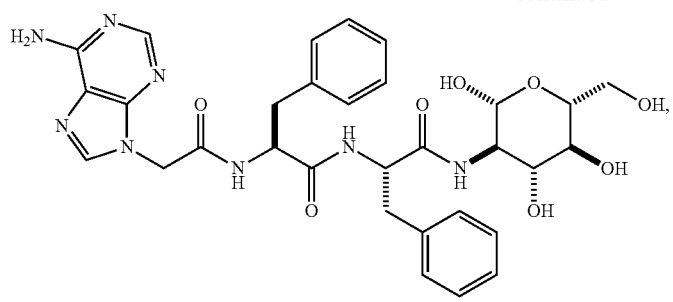
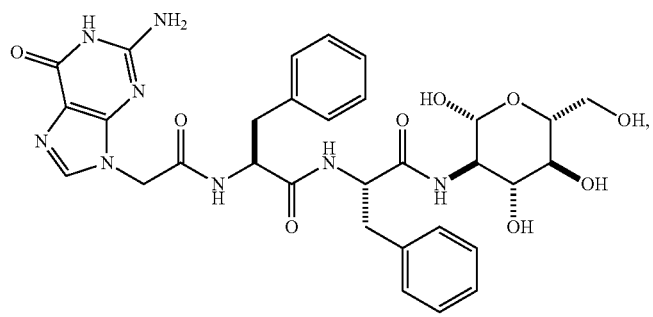
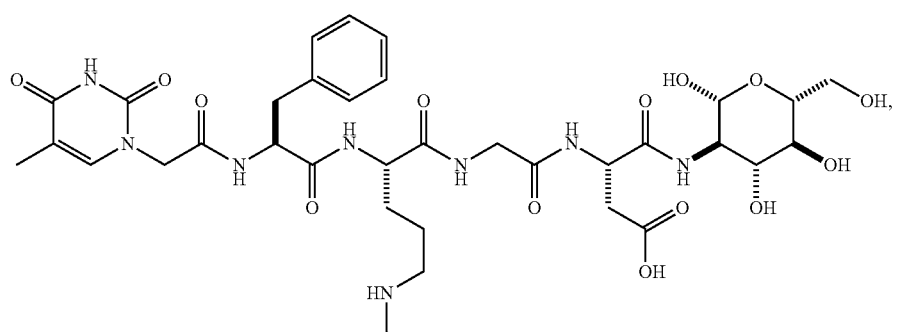
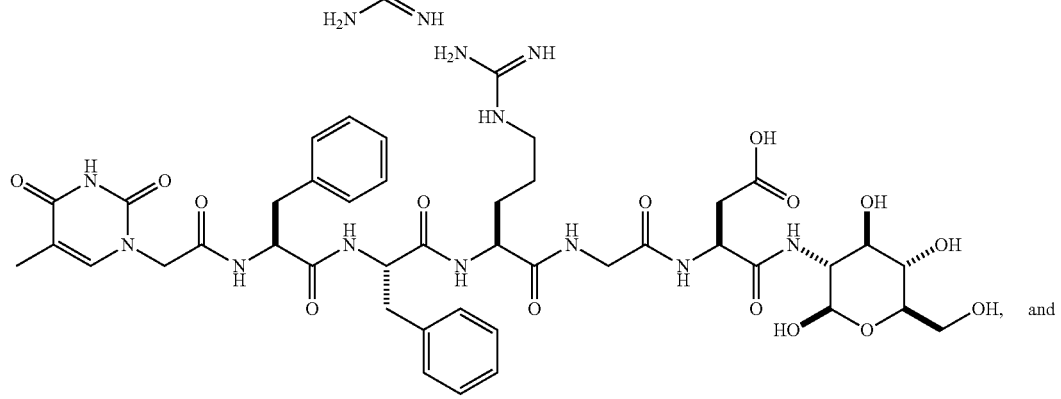
and
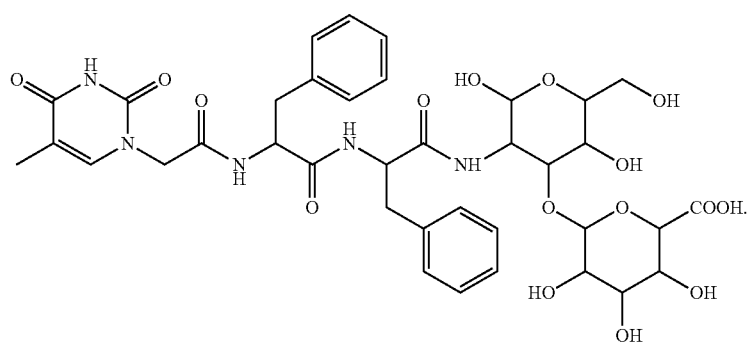

Exemplary Supramolecular Structures of the Invention

In certain embodiments, the invention relates to a supramolecular structure, comprising a plurality of any one of the aforementioned hydrogelators.

In certain embodiments, the invention relates to any one of the aforementioned supramolecular structures, wherein the supramolecular structure is in the form of nanofibers or nanobelts. In certain embodiments, the average diameter of the nanofibers or the average width of the nanobelts is about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, or about 25 nm. In certain embodiments, the nanofibers are crosslinked. In certain diameters, the nanofibers are substantially straight. In certain embodiments, the nanofibers are bent. In certain embodiments, the nanofibers form bundles of nanofibers. In certain embodiments, the nanofibers are about 100 nm, about 120 nm, about 140 nm, about 160 nm, about 180 nm, about 200 nm, about 220 nm, about 240 nm, about 260 nm, about 280 nm, or about 300 nm in length.

In certain embodiments, the invention relates to any one of the aforementioned supramolecular structures, wherein the supramolecular structure is in the form of aggregated nanoparticles. In certain embodiments, the average diameter of the aggregated nanoparticles is about 20 nm, about 21 nm, about 22 nm, about 23 nm, about 24 nm, about 25 nm, about 26 nm, about 27 nm, about 28 nm, about 29 nm, about 30 nm, about 31 nm, about 32 nm, about 33 nm, about 34 nm, or about 35 nm.

Exemplary Hydrogels of the Invention

In certain embodiments, the invention relates to a hydrogel, wherein the hydrogel comprises a plurality of any one of the aforementioned hydrogelators; and water.

In certain embodiments, the invention relates to a hydrogel, wherein the hydrogel comprises a plurality of any one of the aforementioned supramolecular structures; and water.

In certain embodiments, the invention relates to any one of the aforementioned hydrogels, wherein the hydrogel is formed from a solution of the hydrogelators in water. In certain embodiments, the hydrogelator is present in an amount from about 1.5% to about 6% by weight. In certain embodiment, the hydrogelator is present in an amount of about 2.0%, about 2.5%, about 3.0%, about 3.5%, or about 4.0% by weight.

In certain embodiments, the invention relates to any one of the aforementioned hydrogels, wherein the hydrogel is formed from a solution of the hydrogelators in water. In certain embodiments, the pH of the solution is about 10.0, about 9.5, about 9.0, or about 8.5.

In certain embodiments, the invention relates to any one of the aforementioned hydrogels, wherein the hydrogel is formed from a solution of the hydrogelators in water. In certain embodiments, the temperature of the solution is about 20° C., about 25° C., about 30° C., about 35° C., or about 40° C.

In certain embodiments, the invention relates to any one of the aforementioned hydrogels, wherein the hydrogel is formed by decreasing the pH of the solution of hydrogelators in water. In certain embodiments, the pH at which the supramolecular structure is formed is about 9.0, about 8.5, about 8.0, about 7.5, about 7.0, about 6.5, about 6.0, about 5.5, about 5.0, about 4.5, about 4.0, or about 3.5.

In certain embodiments, the invention relates to any one of the aforementioned hydrogels, wherein the hydrogel has a critical strain value of from about 0.15% to about 0.45%. In certain embodiments, the invention relates to any one of the aforementioned hydrogels, wherein the hydrogel has a critical strain value of about 0.15%, about 0.16%, about 0.17%, about 0.18%, about 0.19%, about 0.20%, about 0.21%, about 0.22%, about 0.23%, about 0.24%, about 0.25%, about 0.26%, about 0.27%, about 0.28%, about 0.29%, about 0.30%, about 0.31%, about 0.32%, about 0.33%, about 0.34%, about 0.35%, about 0.36%, about 0.37%, about 0.38%, about 0.39%, about 0.40%, about 0.41%, about 0.42%, about 0.43%, about 0.44%, or about 0.45%.

In certain embodiments, the invention relates to any one of the aforementioned hydrogels, wherein the hydrogel has a storage modulus of from about 0.2 KPa to about 150 KPa. In certain embodiments, the invention relates to any one of the aforementioned hydrogels, wherein the hydrogel has a storage modulus of about 0.2 KPa, about 0.3 KPa, about 0.4 KPa, about 0.5 KPa, about 0.6 KPa, about 0.8 KPa, about 1 KPa, about 2 KPa, about 3 KPa, about 4 KPa, about 5 KPa, about 6 KPa, about 7 KPa, about 8 KPa, about 9 KPa, about 10 KPa, about 15 KPa, about 20 KPa, about 25 KPa, about 30 KPa, about 35 KPa, about 40 KPa, about 50 KPa, about 60 KPa, about 70 KPa, about 80 KPa, about 90 KPa, about 100 KPa, about 110 KPa, about 120 KPa, about 130 KPa, about 140 KPa, or about 150 KPa.

In certain embodiments, the invention relates to any one of the aforementioned hydrogels, wherein the hydrogel is substantially biocompatible. In certain embodiments, the invention relates to any one of the aforementioned hydrogels, wherein the hydrogel is substantially biostable.

Exemplary Methods of the Invention

In certain embodiments, the invention relates to a method of growing cells, comprising contacting a plurality of cells with any one of the aforementioned supramolecular structures or any one of the aforementioned hydrogels. In certain embodiments, the cells are engineered tissue cells. In certain embodiments, the cells are stem cells. In certain embodiments, the cells are skin cells.

In certain embodiments, the invention relates to a method of delivering a substance to a cell, comprising contacting the substance with any one of the aforementioned supramolecular structures or any one of the aforementioned hydrogels, thereby forming a substance-hydrogel delivery vehicle; and contacting the substance-hydrogel delivery vehicle and a cell.

In certain embodiments, the invention relates to any one of the aforementioned methods, wherein the substance is a drug. In certain embodiments, the invention relates to any one of the aforementioned methods, wherein the substance is a protein. In certain embodiments, the invention relates to any one of the aforementioned methods, wherein the substance is a gene. In certain embodiments, the invention relates to any one of the aforementioned methods, wherein the substance is siRNA. In certain embodiments, the invention relates to any one of the aforementioned methods, wherein the substance is microRNA. In certain embodiments, the invention relates to any one of the aforementioned methods, wherein the substance is a second cell.

In certain embodiments, the invention relates to a method of binding a nucleic acid, comprising contacting a nucleic acid with any one of the aforementioned supramolecular structures or any one of the aforementioned hydrogels.

In certain embodiments, the invention relates to any one of the aforementioned methods, wherein the nucleic acid binding is selective nucleic acid binding.

In certain embodiments, the invention relates a method of separating a protein from a substance, comprising contacting a mixture with any one of the aforementioned supramolecular structures or any one of the aforementioned hydrogels, wherein the mixture comprises a protein.

In certain embodiments, the invention relates to any one of the aforementioned methods, wherein the mixture comprises at least two proteins.

In certain embodiments, the invention relates to a method of treating or preventing a viral infection, comprising administering to a mammal in need thereof a therapeutically effective amount of any one of the aforementioned hydrogelators.

In certain embodiments, the invention relates to a method of treating or preventing cancer, comprising administering to a mammal in need thereof a therapeutically effective amount of any one of the aforementioned hydrogelators.

In certain embodiments, the invention relates to a method of preventing adhesion of an organism or a cell to a surface, comprising contacting the surface with any one of the aforementioned supramolecular structures or any one of the aforementioned hydrogels.

EXEMPLIFICATION

The invention now being generally described, it will be more readily understood by reference to the following examples, which are included merely for purposes of illustration of certain aspects and embodiments of the present invention, and are not intended to limit the invention.

Example 1

Materials, Techniques, and General Procedures

Chemical reagents and solvents were used as received from commercial sources. $^1$H, $^{13}$C, and $^{31}$P NMR spectra were obtained on a Varian Unity Inova 400 NMR spectrometer, CD on a JASCO J-810 spectrometer, LC-MS on a Waters Acouity ultra Performance LC with a Waters MICROMASS detector, TEM on a Morgagni 268 transmission electron microscope.

Example 2

Synthetic Methods

Figure 3:
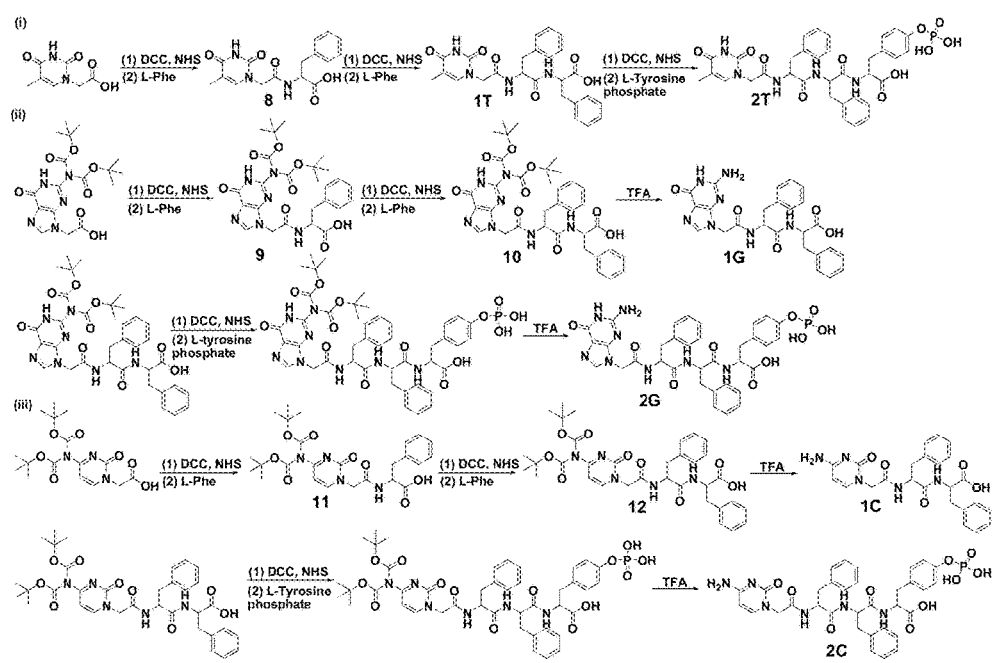
FIG. 3 depicts the molecular structures of, and exemplary synthetic routes to, nucleopeptides 1T, 2T, 1G, 2G, 1C and 2C.

FIG. 3 depicts five synthetic schemes for various compounds of the invention.

Synthesis of Bis-Boc-Adenine-Phe (5). Bis-Boc adenine acetic acid (393.4 mg, 1 mmol) and NHS (126.5 mg, 1.1 mmol) were dissolved in 30 mL of THF, and DCC (226.6 mg, 1.1 mmol) was added to the above solution with stirring. After the reaction, the mixture was stirred at room temperature overnight, and the resulting solid was filtered off. The filtrate was evaporated under reduced pressure to dryness to afford the crude product for the next reaction without purification.

L-Phenylalanine (166 mg, 1 mmol) and $Na_2CO_3$ (84.8 mg, 0.8 mmol) were dissolved in 20 mL of water with stirring, and the solution of crude product (dissolved in 30 mL THF) was added. The resulted reaction mixture was stirred at room temperature for 24 h. After evaporation of the organic solvent, the residue was redissovled in 30 mL of water and acidified with hydrochloric acid to pH 2-3. The white precipitate was filtered off and purified by column chromatography over silica gel using chloroform/methanol as the eluents to afford compound 5 (443 mg, 82%) for next step reaction. $^1$H NMR (400 MHz, DMSO-d$_6$): δ 8.80 (s, 1H), 8.66 (b, 1H), 8.50 (s, 1H), 7.27-7.17 (m, 5H), 5.03 (dd, J=20.0 Hz, 24.0 Hz, 2H), 4.37 (m, 1H), 3.08 (dd, J=4.0, 12.0 Hz, 1H), 2.92 (dd, J=8.0, 12.0 Hz, 1H), 1.37 (s, 18H) ppm.

Synthesis of Bis-Boc-Adenine-Phe-Phe (6). Compound 5 (540 mg, 1 mmol) and NHS (126.5 mg, 1.1 mmol) were dissolved in THF (30 mL), and DCC (226.6 mg, 1.1 mmol) was added to the above solution with stirring. After the reaction mixture was stirred at room temperature for 12 h, the resulting solid was filtered off. Then the filtrate was evaporated under reduced pressure to dryness. The crude product was used for the next step reaction without purification.

L-Phenylalanine (166 mg, 1 mmol) and $Na_2CO_3$ (84.8 mg, 0.8 mmol) were dissolved in water (20 mL) with stirring, and the solution of crude product (dissolved in 30 mL of THF) was added. The resulted reaction mixture was stirred at room temperature for 24 h. After evaporation of the organic solvent, the residue was redissovled in 30 mL of water and acidified with hydrochloric acid to pH 2-3. The white precipitate was filtered off and purified by column chromatography over silica gel using chloroform/methanol as the eluents to afford compound 6 (488 mg, 80%). $^1$H NMR (400 MHz, DMSO-d$_6$): δ 8.78 (s, 1H), 8.70 (d, J=8.0 Hz, 1H), 8.49 (d, J=8.0 Hz, 1H), 8.42 (s, 1H), 7.24-7.10 (m, 10H), 4.96 (dd, J=16.0, 28.0 Hz, 2H), 4.61-4.56 (m, 1H), 4.46-4.40 (m, 1H), 3.09-2.99 (m, 2H), 2.91 (dd, J=8.0, 12.0 Hz, 1H), 2.75 (dd, J=8.0, 12.0 Hz, 1H), 1.37 (s, 18H) ppm.

Synthesis of Adenine-Phe-Phe (1A). 0.5 mmol of compound 6 (344 mg) was dissolved in 10 mL of 90% Trifluoroacetic acid in water and stirred at room temperature for 2 h. The reaction mixture was concentrated by vacuum and the white solid was purified by using HPLC with water-acetonitrile as eluent (from 8:2 to 4:6) to afford the product (1A) in 73% yield. $^1$H NMR (400 MHz, DMSO-d$_6$): δ 8.63 (d, J=8.0 Hz, 1H), 8.51 (d, J=8.4 Hz, 1H), 8.29 (s, 1H), 8.12 (s, 1H), 7.24-7.18 (m, 10H), 4.85 (dd, J=29.6, 16.4 Hz, 2H), 4.60-4.55 (m, 1H), 4.46-4.41 (m, 1H), 3.06-2.96 (m, 2H), 2.90 (dd, J=16.4, 10.0 Hz, 1H), 2.74 (dd, J=13.6, 4.8 Hz, 1H). $^{13}$C NMR (400 MHz, DMSO-d$_6$): δ 37.2, 38.4, 45.9, 54.3, 54.5, 118.4, 127.1, 127.2 128.8, 128.9, 129.7, 129.9, 138.0, 144.8, 147.3, 149.5, 152.0, 166.1, 171.5, 173.4. MS: calcd M$^+$=487.51, obsd (M+1)$^+$=488.51.

Synthesis of Adenine-Phe-Phe-Tyr-phosphate (2A). Compound 6 (687.7 mg, 1 mmol) and NHS (126.5 mg, 1.1 mmol) were dissolved in THF (30 mL), and DCC (226.6 mg, 1.1 mmol) was added to the above solution with stirring. After the reaction, the mixture was stirred at room temperature for 12 h, and the resulted solid was filtered off. The filtrate was evaporated under reduced pressure to dryness. The crude product was used for the next reaction without purification.

L-Tyrosine-phosphate (261.17 mg, 1 mmol) and $Na_2CO_3$ (212 mg, 2 mmol) were dissolved in water (20 mL) with stirring, and the solution of crude product (dissolved in 30 mL of THF) was added. The resulted reaction mixture was stirred at room temperature for 24 h. After evaporation of the organic solvent, the residue was redissovled in 30 mL of water and acidified with hydrochloric acid to pH 2. The white precipitate was filtered off and treated with 90% trifluoroacetic acid in water for 2 h. Then the mixture was concentrated by vacuum and purified by using HPLC with water-acetonitrile as eluent (from 8:2 to 5:5) to afford product (2A) in 51% yield. $^1$H NMR (400 MHz, DMSO-d$_6$): δ 8.51 (d, J=8.0 Hz, 1H), 8.32-8.26 (m, 1H), 8.13 (s, 1H), 7.96 (s, 1H), 7.62 (s, 1H), 7.26-7.06 (m, 14H), 4.78 (dd, J=30.0, 16.8 Hz, 2H), 4.52-4.41 (m, 3H), 3.04-2.68 (m, 6H). $^{13}$C NMR (400 MHz, DMSO-d$_6$): δ 37.7, 38.6, 38.8, 45.8, 54.1, 54.5, 118.5, 120.4, 126.9, 127.2, 128.6, 128.8, 130.0, 130.8, 133.5, 137.8, 138.5, 144.4, 148.4, 150.0, 150.9, 153.0, 166.2, 171.0, 173.5. MS: calcd M$^+$=730.66, obsd (M+Na)$^+$=753.66.

Synthesis of Thymine-Phe (8). Thymine acetic acid (184 mg, 1 mmol) and NHS (126.5 mg, 1.1 mmol) were dissolved in 20 mL of DMF, and DCC (226.6 mg, 1.1 mmol) was added to the above solution with stirring. After the reaction, the mixture was stirred at room temperature overnight, and the resulted solid was filtered off. The filtrate was evaporated under reduced pressure to dryness, and the crude product was used in the next reaction without purification.

L-Phenylalanine (166 mg, 1 mmol) and Na$_2$CO$_3$ (84.8 mg, 0.8 mmol) were dissolved in 20 mL of water with stirring, and the solution of crude product (dissolved in 20 mL DMF) was added. The resulted reaction mixture was stirred at room temperature for 24 h. The reaction mixture was vacuum-dried, then 30 mL of water was added and acidified to pH=3. The resulted product was obtained by filtration, washed with water, and then dried in vacuum. The white solid was purified by using HPLC with water-acetonitrile as eluent (from 8:2 to 4:6) to afford the product (8) in 78% yield for next step reaction. $^1$H NMR (400 MHz, DMSO-d$_6$): δ 8.56-8.54 (m, 1H), 7.33-7.20 (m, 6H), 4.45-4.40 (m, 1H), 4.19 (dd, J=16.0, 28.0 Hz, 2H), 3.04 (dd, J=4.0, 12.0 Hz, 1H), 2.89 (dd, J=8.0, 16.0 Hz, 1H), 1.73 (s, 3H) ppm.

Synthesis of Thymine-Phe-Phe (1T). Compound 8 (331 mg, 1 mmol) and NHS (126.5 mg, 1.1 mmol) were dissolved in 20 mL of DMF, and DCC (226.6 mg, 1.1 mmol) was added to the above solution with stirring. After the reaction mixture was stirred at room temperature overnight, the resulted solid was filtered off, and the filtrate was evaporated under reduced pressure to dryness. The crude product was used in the next reaction without purification.

L-Phenylalanine (166 mg, 1 mmol) and Na$_2$CO$_3$ (84.8 mg, 0.8 mmol) were dissolved in 20 mL of water with stirring, and the solution of crude product (dissolved in 20 mL DMF) was added. The resulted reaction mixture was stirred at room temperature for 24 h. The reaction mixture was vacuum-dried, then 30 mL of water was added and the mixture was acidified to pH=3. The resulted product was obtained by filtration, washed with water, and then dried in vacuum. Compound 1T (white powder) was collected with 76% yield (364 mg). $^1$H NMR (400 MHz, DMSO-d$_6$): δ 8.41-8.37 (m, 1H), 7.29-7.18 (m, 10H), 4.57-4.52 (m, 1H), 4.43-4.38 (m, 1H), 4.23 (dd, J=16.8, 28.4 Hz, 2H), 3.06-2.89 (m, 3H), 2.72 (dd, J=9.6, 15.2 Hz, 1H), 1.71 (s, 3H). $^{13}$C NMR (400 MHz, DMSO-d$_6$): δ 12.6, 38.4, 49.5, 55.0, 55.6, 108.6, 126.6, 126.9, 128.5, 128.7, 130.0, 130.1, 138.5, 139.3, 142.8, 151.6, 165.0, 167.3. MS: calcd M$^+$=478.50, obsd (M+1)$^+$=479.50.

Synthesis of Thymine-Phe-Phe-Tyr-phosphate (2T). Compound 1T (478.5 mg, 1 mmol) and NHS (126.5 mg, 1.1 mmol) were dissolved in DMF (30 mL), and DCC (226.6 mg, 1.1 mmol) was added to the above solution with stirring. After the reaction mixture was stirred at room temperature for 12 h, the resulted solid was filtered off, and the filtrate was evaporated under reduced pressure to dryness. The crude product was used for the next reaction without purification.

L-Tyrosine-phosphate (261.17 mg, 1 mmol) and Na$_2$CO$_3$ (212 mg, 2 mmol) were dissolved in water (20 mL) with stirring, and the solution of crude product (dissolved in 30 mL of DMF) was added. The resulted reaction mixture was stirred at room temperature for 24 h. The reaction mixture was vacuum-dried, then 30 mL of water was added and the mixture was acidified to pH~2.0. The resulted product was isolated by filtration, washed with water, and then dried in vacuum. The white solid was purified by using HPLC with water-acetonitrile as eluent (from 8:2 to 5:5) to afford the product (2T) in 53% yield (382 mg). $^1$H NMR (400 MHz, DMSO-d$_6$): δ 8.29 (dd, J=9.2, 32.0 Hz, 1H), 7.26-7.06 (m, 14H), 4.56-4.42 (m, 3H), 4.23 (d, J=4.8 Hz, 2H), 3.03-2.88 (m, 4H), 2.81-2.67 (m, 2H), 1.71 (s, 3H). $^{13}$C NMR (400 MHz, DMSO-d$_6$): δ 12.6, 36.6, 38.1, 38.3, 49.6, 54.4, 55.6, 108.5, 120.4, 126.9, 128.7, 130.0, 130.5, 138.2, 138.4, 142.9, 151.6, 165.1, 167.2, 171.2, 171.9, 173.3. MS: calcd M$^+$=721.65, obsd (M+Na)$^+$=744.65.

Synthesis of Bis-Boc-Guanine-Phe (9). Compound 9 was synthesized by following the procedures described in synthesis of compound 5 except replacing the bis-Boc adenine acetic acid with bis-Boc guanine acetic acid. Compound 1Ga (white powder) was collected with 81% yield (462 mg). $^1$H NMR (400 MHz, DMSO-d$_6$): δ 8.71 (d, J=8.0 Hz, 1H), 8.51 (d, J=8.0 Hz, 1H), 7.31-7.19 (m, 5H), 4.91-4.79 (m, 2H), 4.44 (m, 1H), 3.06-3.01 (m, 2H), 2.94-2.88 (m, 2H), 1.34 (s, 18H) ppm.

Synthesis of Bis-Boc-Guanine-Phe-Phe (10). Compound 10 was synthesized by following the procedures described in synthesis of compound 6 except replacing the bis-Boc adenine acetic acid with bis-Boc guanine acetic acid. Compound 10 (white powder) was collected with 75% yield (528 mg). $^1$H NMR (400 MHz, DMSO-d$_6$): δ 8.52 (d, J=8.0 Hz, 1H), 8.45 (s, 1H), 7.93 (s, 1H), 7.23-7.17 (m, 10H), 4.83-4.70 (m, 2H), 4.56 (s, 1H), 4.40 (s, 1H), 3.08-2.99 (m, 2H), 2.92-2.71 (m, 2H), 1.33 (s, 18H) ppm.

Synthesis of Guanine-Phe-Phe (1G). Compound 1G was synthesized by following the procedures described in synthesis of compound 1A except replacing the bis-Boc adenine acetic acid with bis-Boc guanine acetic acid. Compound 1G (white powder) was collected with 58% yield (292 mg). $^1$H NMR (400 MHz, DMSO-d$_6$): δ 8.56-8.51 (m, 2H), 7.71 (s, 1H), 7.26-7.18 (m, 10H), 4.70 (s, 2H), 4.60-4.54 (m, 1H), 4.45-4.40 (m, 1H), 3.09-2.96 (m, 2H), 2.93-2.87 (m, 1H), 2.76-2.70 (m, 1H). $^{13}$C NMR (400 MHz, DMSO-d$_6$): δ 37.3, 38.7, 45.7, 54.3, 54.4, 54.4, 127.0, 127.2, 128.7, 128.9, 129.8, 130.0, 138.1, 138.2, 166.3, 171.5, 173.4. MS: calcd M$^+$=503.51, obsd (M+1)$^+$=504.51.

Synthesis of Guanine-Phe-Phe-Tyr-phosphate (2G). Compound 2G was synthesized by following the procedures described in synthesis of compound 2A except replacing the bis-Boc adenine acetic acid with bis-Boc guanine acetic acid. Compound 2G (white powder) was collected with 51% yield (381 mg). $^1$H NMR (400 MHz, DMSO-d$_6$): δ 8.53 (t, J=8.0 Hz, 1H), 8.42 (s, 1H), 8.27 (t, J=8.0 Hz, 1H), 7.61 (s, 1H), 7.26-7.06 (m, 14H), 4.66-4.36 (m, 5H), 3.07-2.67 (m, 6H). $^{13}$C NMR (400 MHz, DMSO-d$_6$): δ 22.9, 37.3, 38.2, 44.4, 45.7, 46.3, 54.4, 54.6, 55.6, 113.2, 120.1, 127.0, 128.8, 129.8, 130.9, 132.8, 138.1, 138.4, 139.0, 151.3, 154.8, 166.2, 171.0, 171.5, 171.9, 173.4. MS: calcd M$^+$=746.66, obsd (M+Na)$^+$=769.66.

Synthesis of Bis-Boc-Cytosine-Phe (12). Compound 12 was synthesized by following the procedures described in synthesis of compound 5 except replacing the bis-Boc adenine acetic acid with bis-Boc cytosine acetic acid. Compound 12 (white powder) was collected with 83% yield (429 mg). $^1$H NMR (400 MHz, DMSO-d$_6$): δ 8.29 (s, 1H), 8.01 (d, J=4.0 Hz, 1H), 7.22-7.16 (m, 5H), 6.79 (d, J=8.0 Hz, 1H), 4.58-4.41 (m, 2H), 4.27 (s. 1H), 1.49 (s, 18H) ppm.

Synthesis of Bis-Boc-Cytosine-Phe-Phe (13). Compound 13 was synthesized by following the procedures described in synthesis of compound 6 except replacing the bis-Boc adenine acetic acid with bis-Boc cytosine acetic acid. Compound 13 (white powder) was collected with 78% yield (518 mg). $^1$H NMR (400 MHz, DMSO-$d_6$): δ 8.51 (d, J=8.0 Hz, 1H), 8.41 (d, J=8.0 Hz, 1H), 7.94 (d, J=8.0 Hz, 1H), 7.29-7.16 (m, 10H), 6.77 (d, J=8.0 Hz, 1H), 4.58-4.38 (m, 4H), 3.07-2.71 (m, 4H), 1.48 (s, 18H) ppm Synthesis of Cytosine-Phe-Phe (1C). Compound 1C was synthesized by following the procedures described in synthesis of compound 1A except replacing the bis-Boc adenine acetic acid with bis-Boc cytosine acetic acid. Compound 1C (white powder) was collected with 61% yield (283 mg). $^1$H NMR (400 MHz, DMSO-$d_6$): δ 8.87 (s, 1H), 8.48 (d, J=7.6 Hz, 2H), 8.16 (s, 1H), 7.66 (d, J=7.6 Hz, 1H), 7.30-7.16 (m, 10H), 5.91 (d, J=8.4 Hz, 1H), 4.59-4.54 (m, 1H), 4.45-4.41 (m, 3H), 3.01-2.90 (m, 3H), 2.75-2.70 (m, 1H). $^{13}$C NMR (400 MHz, DMSO-$d_6$): δ 36.7, 37.8, 50.4, 53.7, 93.1, 126.4, 126.5, 128.1, 128.3, 129.2, 129.4, 137.6, 149.7, 161.6, 166.1, 170.9, 172.8. MS: calcd $M^+$=463.49, obsd $(M+1)^+$=464.49.

Synthesis of Cytosine-Phe-Phe-Tyr-phosphate (2C). Compound 2C was synthesized by following the procedures described in synthesis of compound 2A except replacing the bis-Boc adenine acetic acid with bis-Boc cytosine acetic acid. Compound 2C (white powder) was collected with 51% yield (360 mg). $^1$H NMR (400 MHz, DMSO-$d_6$): δ 8.54-8.42 (m, 2H), 8.24-8.19 (m, 1H), 7.62 (s, 1H), 7.26-7.06 (m, 14H), 5.85 (d, J=7.2 Hz, 1H), 4.54-4.45 (m, 5H), 3.04-2.66 (m, 6H). $^{13}$C NMR (400 MHz, DMSO-$d_6$): δ 36.5, 37.9, 51.4, 54.4, 54.8, 93.8, 120.6, 126.9, 128.7, 129.9, 130.6, 138.2, 149.0, 151.7, 158.5, 170.9, 173.2. MS: calcd $M^+$=706.64, obsd $(M+Na)^+$=729.64.

Example 3

Gelation Triggered by Alkaline Phosphatase

We dissolved 6.0 mg of precursor 2 in 300 μL of water at pH=7.4 to make a clear solution, then followed by adding 10 unit of alkaline phosphatase in 1 μL to afford a translucent hydrogel.

FIG. 6, FIG. 7, FIG. 8, and FIG. 9 depict the $^{31}$P NMR spectra of hydrogelators 2A, 2G, 2T, and 2C before and after the addition of alkaline phosphatase (ALP).

Example 4

Circular Dichroism (CD) Spectroscopy

CD spectra were recorded (185-350 nm) using a JASCO 810 spectrometer under a nitrogen atmosphere. The hydrogels (0.2 mL, 2.0 wt %) were placed evenly on the 1 mm thick quartz curvet and scanned with 0.5 nm interval.

Figure 10:
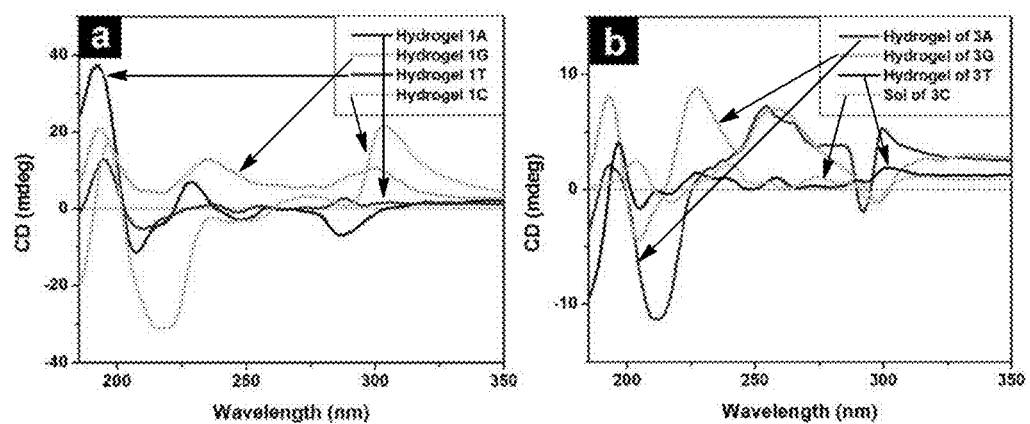
FIG. 10 depicts CD spectra of (a) the hydrogels formed by hydrogelators 1A, 1G, 1T and 1C, respectively; and (b) the hydrogels formed by 3A, 3G, and 3T, respectively, and the solution of 3C.
Figure 11:
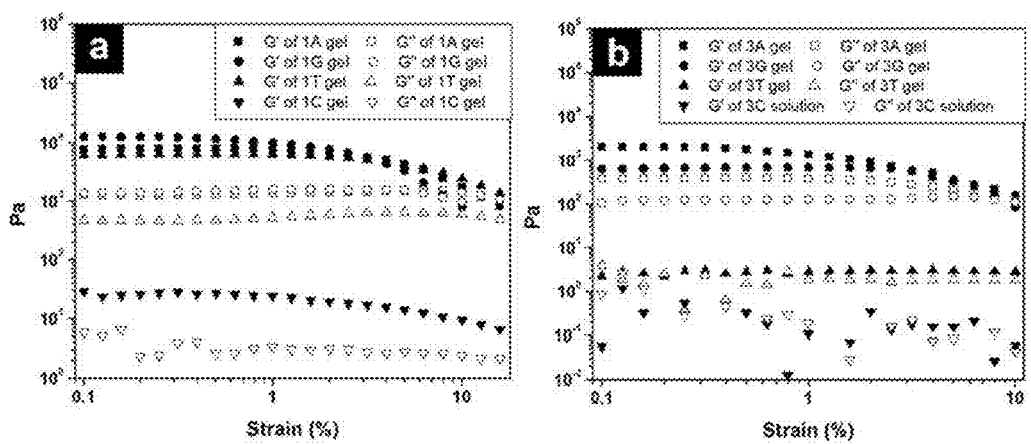
FIG. 11 depicts the strain dependence of the dynamic storage moduli (G') and loss moduli (G") of (a) the hydrogels formed by hydrogelators 1A, 1G, 1T, 1C, respectively; and (b) the hydrogels formed by hydrogelator 3A, 3G, 3T, respectively, and the solution of 3C.

FIG. 10 depicts CD spectra of various hydrogels of the invention.

Example 5

Rheological Measurements

Rheological tests were conducted on TA ARES G2 rheometer (with TA Orchestrator Software). 25 mm parallel plate was used during the experiment. 0.5 mL of hydrogel sample was placed on the parallel plate.

i) Dynamic Strain Sweep Test

Test range (0.1 to 10% strain, frequency=10 rads$^{-1}$), 10 points per decade. Sweep mode is "log" and temperature was carried out at 25° C.

ii) Critical Strain Determination

The critical strain ($γ_0$) value was determined from the storage-strain profiles of the hydrogel sample. The strain applied to the hydrogel sample increased from 0.1 to 100% (10 rad/s and 25° C.). Over a certain strain, a drop in the elastic modulus was observed, and the strain amplitude at which storage moduli just begins to decrease by 5% from its maximum value was determined and taken as a measure of the critical strain of the hydrogels, which correspond to the breakdown of the crosslinked network in the hydrogel sample.

Example 6

Figure 12:
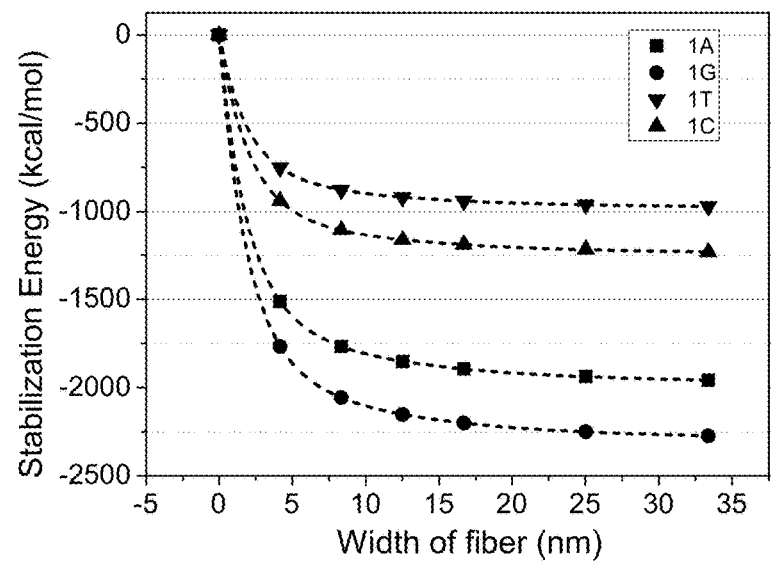
FIG. 12 depicts the calculated fiber width dependences of the stabilization energies of 1A, 1G, 1T and 1C, respectively.

Simulation of the Width of the Nanofibers by Molecular Mechanical (MM) Calculation Molecular mechanics (MM) calculations were carried out to simulate the nanofibers of nucleopeptides with different diameters using the Dreiding Force Field as implemented in the molecular modeling programs (Accelrys Inc., San Diego, Calif., USA). The initial crystal parameters of nucleopeptides were obtained from NapFF crystal structure. Then, the crystal structures of nucleopeptides were optimized by MM method. We determined the crystal growth habit of the nucleopeptide nanofibers by employing the Bravais-Friedel-Donnay-Harker (BFDH) method. We found all growth habits of the nanofibers are in the order of A>B>C axes. Accordingly, we fixed the long axis (A axis) to 33 unit cells and varied the widths (B axis) of the nanofibers to calculate the stabilization energy of the nanofibers. The width dependences of the stabilization energies are shown in FIG. 12.

Nonlinear curve fittings were carried out by three exponential functions $$y=y_0+A_1 e^{-x/b_1}+A_2 e^{-x/b_2}+A_3 e^{-x/b_3}$$

where $A_n$ and $b_n$ coefficients are calculated by the iterative method. Based on this method, we obtained four $y_0$ (i.e., the stabilization energy with infinity width). We fixed 1T to 9 nm as a reference and then we can calculate the energy difference as the scaling factor based on $y_0$ of 1T. According to this reference energy, we can estimate fiber diameters for other nucleopeptide nanofibers. Finally, we found that the simulated fiber diameters of nucleopeptides are in good agreement with the experimental data observed by TEM.

Example 7

Wound-Healing Assay

Figure 14:
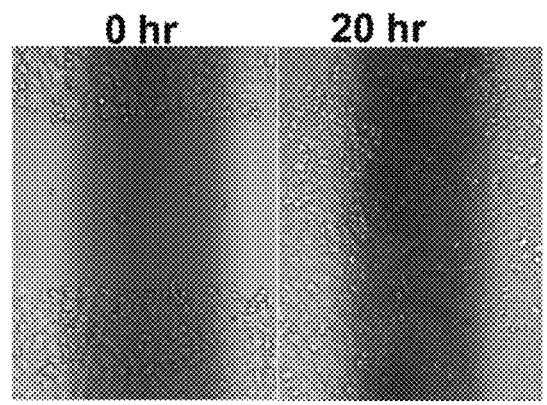
FIG. 14 depicts optical images of HeLa cells on the surface 0 h and 20 h after the creation of scratch-wound in the medium without the presence of the hydrogel of 3T.

HeLa cells were re-suspended in 10 cm tissue culture dish after washing cells once with PBS. 0.8 mL 0.25% trypsin containing 0.1% EDTA was then added, and the cells were re-suspended with 1.6 mL complete medium. 5000 cells (in 100 μL medium) were plated into each vial on a 96 well plate to create a confluent monolayer. After adherent for 24 hr, a wound was created by scraping the cell monolayer with a p200 pipet tip. The cells were washed once with 100 μL of complete medium to remove flowing cells and replace with 100 μL of complete medium. 0 hr image was acquired as a reference point. The medium was replaced with 100 μL of medium containing 27.7 mM of hydrogel 3T and the plate was incubate at 37° C., 5% $CO_2$ for 20 h. 0-h and 20-h images were acquired at the match photographed region. FIG. 13d depicts optical images of HeLa cells on the surface 0 h and 20 h after the creation of scratch-wound in the medium in the presence of hydrogel 3T. FIG. 14 depicts the control (no hydrogel).

Example 8

Figure 15:
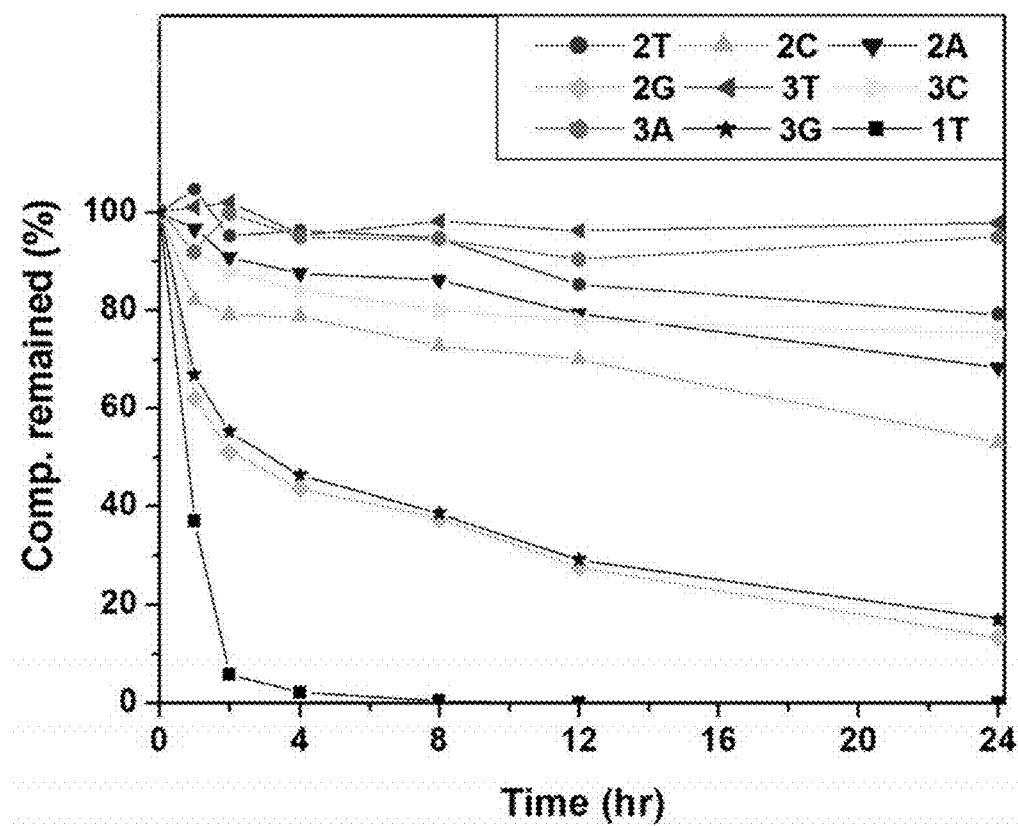
FIG. 15 depicts the time-dependent course of the digestions of hydrogelators of 1T, 2T, 2C, 2G, 2A, 3T, 3C, 3A, and 3G by proteinase K.

Biostability 1 mg of each compound was dissolved in 5 mL HEPES buffer at pH=7.5. Then proteinase K was added in concentration 3.2 units/mL and incubated at 37° C. for 24 h, then 100 μL of sample were taken out each time and analyzed by HPLC. FIG. 15.

Example 1'

Materials, Techniques, and General Procedures

The materials, techniques, and general procedures apply to the remainder of the Examples. Chemical reagents and solvents were used as received from commercial sources. $^1$H and $^{13}$C, spectra were obtained on Varian Unity Inova 400, CD on a JASCO J-810 spectrometer, LC-MS on Waters Acouity ultra Performance LC with Waters MICROMASS detector, TEM on Morgagni 268 transmission electron microscope.

Example 2'

Synthetic Methods

FIG. 18 depicts six synthetic schemes for various compounds of the invention.

Synthesis of Thymine-Phe (4'). Thymine acetic acid (184 mg, 1 mmol) and NHS (126.5 mg, 1.1 mmol) were dissolved in 20 mL of DMF, and DCC (226.6 mg, 1.1 mmol) was added to the above solution with stirring. After the reaction mixture was stirred at room temperature overnight, and the resulted solid was filtered off. The filtrate was evaporated under reduced pressure to dryness, and the crude product was used in the next reaction without purification.

L-Phenylalanine (166 mg, 1 mmol) and $Na_2CO_3$ (84.8 mg, 0.8 mmol) were dissolved in 20 mL of water with stirring, and the solution of crude product (dissolved in 20 mL DMF) was added. The resulted reaction mixture was stirred at room temperature for 24 h. The reaction mixture was vacuum-dried, then 30 mL of water was added and acidified to pH=3. The resulted product was obtained by filtration, washed with water, and then dried in vacuum. The white solid was purified by using HPLC with water-acetonitrile as eluent (from 8:2 to 4:6) to afford the product (4') in 78% yield for next step reaction. $^1$H NMR (400 MHz, DMSO-$d_6$): δ 8.56-8.54 (m, 1H), 7.33-7.20 (m, 6H), 4.45-4.40 (m, 1H), 4.19 (dd, J=16.0, 28.0 Hz, 2H), 3.04 (dd, J=4.0, 12.0 Hz, 1H), 2.89 (dd, J=8.0, 16.0 Hz, 1H), 1.73 (s, 3H) ppm.

Synthesis of Thymine-Phe-glucosamine (1T'). Compound 4' (331.3 mg, 1 mmol) and NHS (126.5 mg, 1.1 mmol) were dissolved in DMF (30 mL), and DCC (226.6 mg, 1.1 mmol) was added to the above solution with stirring. After the reaction mixture was stirred at room temperature for 12 h, the resulted solid was filtered off, and the filtrate was evaporated under reduced pressure to dryness. The crude product was used for the next reaction without purification.

D-glucosamine hydrochloride (215.64 mg, 1 mmol) and $Na_2CO_3$ (212 mg, 2 mmol) were dissolved in water (20 mL) with stirring, and the solution of crude product (dissolved in 30 mL of DMF) was added. The resulted reaction mixture was stirred at room temperature for 24 h. The reaction mixture was vacuum-dried, followed by the addition of 30 mL of water. The resulted product was isolated by filtration, washed with water, and then dried in vacuum. The white solid was purified by using HPLC with water-acetonitrile as eluent (from 8:2 to 5:5) to afford the product (2T') in 42% yield (206 mg). $^1$H NMR (400 MHz, DMSO-$d_6$): δ 8.34 (d, J=12.0 Hz, 1H), 8.05 (d, J=8.0 Hz, 1H), 7.32-7.14 (m, 5H), 6.54 (d, J=4.0 Hz, 1H), 4.96-4.91 (m, 2H), 4.7-4.61 (m, 1H), 4.48-4.43 (m, 1H), 4.33-4.15 (m, 2H), 3.65-3.43 (m, 4H), 3.18-3.00 (m, 3H), 2.79-2.69 (m, 2H), 1.74-1.69 (s, 3H) ppm.

Synthesis of Thymine-Phe-Phe (5'). Compound 4' (331 mg, 1 mmol) and NHS (126.5 mg, 1.1 mmol) were dissolved in 20 mL of DMF, and DCC (226.6 mg, 1.1 mmol) was added to the above solution with stirring. After the reaction mixture was stirred at room temperature overnight, the resulted solid was filtered off, and the filtrate was evaporated under reduced pressure to dryness. The crude product was used in the next reaction without purification.

L-Phenylalanine (166 mg, 1 mmol) and $Na_2CO_3$ (84.8 mg, 0.8 mmol) were dissolved in 20 mL of water with stirring, and the solution of crude product (dissolved in 20 mL DMF) was added. The resulted reaction mixture was stirred at room temperature for 24 h. The reaction mixture was vacuum-dried, then 30 mL of water was added and the mixture was acidified to pH=3. The resulted product was obtained by filtration, washed with water, and then dried in vacuum. Compound 5' (white powder) was collected with 76% yield (364 mg). $^1$H NMR (400 MHz, DMSO-$d_6$): δ 8.41-8.37 (m, 1H), 7.29-7.18 (m, 10H), 4.57-4.52 (m, 1H), 4.43-4.38 (m, 1H), 4.23 (dd, J=16.8, 28.4 Hz, 2H), 3.06-2.89 (m, 3H), 2.72 (dd, J=9.6, 15.2 Hz, 1H), 1.71 (s, 3H).

Synthesis of Thymine-Phe-Phe-glucosamine (2T'). Compound 5' (478.5 mg, 1 mmol) and NHS (126.5 mg, 1.1 mmol) were dissolved in DMF (30 mL), and DCC (226.6 mg, 1.1 mmol) was added to the above solution with stirring. After the reaction mixture was stirred at room temperature for 12 h, the resulted solid was filtered off, and the filtrate was evaporated under reduced pressure to dryness. The crude product was used for the next reaction without purification.

D-glucosamine hydrochloride (215.64 mg, 1 mmol) and $Na_2CO_3$ (212 mg, 2 mmol) were dissolved in water (20 mL) with stirring, and the solution of crude product (dissolved in 30 mL of DMF) was added. The resulted reaction mixture was stirred at room temperature for 24 h. The reaction mixture was vacuum-dried, then 30 mL of water was added. The resulted product was isolated by filtration, washed with water, and then dried in vacuum. The white solid was purified by using HPLC with water-acetonitrile as eluent (from 8:2 to 5:5) to afford the product (2T') in 48% yield (382 mg). $^1$H NMR (400 MHz, DMSO-$d_6$): δ 8.27 (d, J=12.0 Hz, 1H), 8.13 (d, J=8.0 Hz, 1H), 7.93 (d, J=8.0 Hz, 1H), 7.33-7.13 (m, 10H), 6.56 (d, J=4.0 Hz, 1H), 4.98-4.92 (m, 2H), 4.71-4.43 (m, 3H), 4.28-4.19 (m, 2H), 3.67-3.44 (m, 4H), 3.18-2.64 (m, 7H), 1.74-1.69 (s, 3H) ppm.

Synthesis of Bis-Boc-Adenine-Phe (7'). Bis-Boc adenine acetic acid (393.4 mg, 1 mmol) and NHS (126.5 mg, 1.1 mmol) were dissolved in 30 mL of THF, and DCC (226.6 mg, 1.1 mmol) was added to the above solution with stirring. After the reaction, the mixture was stirred at room temperature overnight, and the resulting solid was filtered off. The filtrate was evaporated under reduced pressure to dryness to afford the crude product for the next reaction without purification.

L-Phenylalanine (166 mg, 1 mmol) and Na$_2$CO$_3$ (84.8 mg, 0.8 mmol) were dissolved in 20 mL of water with stirring, and the solution of crude product (dissolved in 30 mL THF) was added. The resulted reaction mixture was stirred at room temperature for 24 h. After evaporation of the organic solvent, the residue was redissolved in 30 mL of water and acidified with hydrochloric acid to pH 2-3. The white precipitate was filtered off and purified by column chromatography over silica gel using chloroform/methanol as the eluents to afford compound 7' (443 mg, 82%) for next step reaction. $^1$H NMR (400 MHz, DMSO-d$_6$): δ 8.80 (s, 1H), 8.66 (b, 1H), 8.50 (s, 1H), 7.27-7.17 (m, 5H), 5.03 (dd, J=20.0 Hz, 24.0 Hz, 2H), 4.37 (m, 1H), 3.08 (dd, J=4.0, 12.0 Hz, 1H), 2.92 (dd, J=8.0, 12.0 Hz, 1H), 1.37 (s, 18H) ppm.

Synthesis of Adenine-Phe-glucosamine (1A'). Compound 7' (584.66 mg, 1 mmol) and NHS (126.5 mg, 1.1 mmol) were dissolved in THF (30 mL), and DCC (226.6 mg, 1.1 mmol) was added to the above solution with stirring. After the reaction mixture was stirred at room temperature for 12 h, the resulting solid was filtered off. Then the filtrate was evaporated under reduced pressure to dryness. The crude product was used for the next step reaction without purification.

D-glucosamine hydrochloride (215.64 mg, 1 mmol) and Na$_2$CO$_3$ (84.8 mg, 0.8 mmol) were dissolved in water (20 mL) with stirring, and the solution of crude product (dissolved in 30 mL of THF) was added. The resulted reaction mixture was stirred at room temperature for 24 h. After evaporation of the organic solvent, the residue treated with 90% trifluoroacetic acid in water for 2 h. Then the mixture was concentrated by vacuum and purified by using HPLC with water-acetonitrile as eluent (from 8:2 to 5:5) to afford the product (1A') in 42% yield. $^1$H NMR (400 MHz, DMSO-d$_6$): δ 8.57-8.49 (m, 1H), 8.13-8.09 (m, 2H), 7.91 (s, 1H), 7.30-7.15 (m, 5H), 6.55 (d, J=4.0 Hz, 1H), 4.95-4.47 (m, 5H), 3.71-3.48 (m, 4H), 3.16-2.71 (m, 5H) ppm.

Synthesis of Bis-Boc-Adenine-Phe-Phe (9'). Compound 7' (540 mg, 1 mmol) and NHS (126.5 mg, 1.1 mmol) were dissolved in THF (30 mL), and DCC (226.6 mg, 1.1 mmol) was added to the above solution with stirring. After the reaction mixture was stirred at room temperature for 12 h, the resulting solid was filtered off. Then the filtrate was evaporated under reduced pressure to dryness. The crude product was used for the next step reaction without purification.

L-Phenylalanine (166 mg, 1 mmol) and Na$_2$CO$_3$ (84.8 mg, 0.8 mmol) were dissolved in water (20 mL) with stirring, and the solution of crude product (dissolved in 30 mL of THF) was added. The resulted reaction mixture was stirred at room temperature for 24 h. After evaporation of the organic solvent, the residue was redissovled in 30 mL of water and acidified with hydrochloric acid to pH 2-3. The white precipitate was filtered off and purified by column chromatography over silica gel using chloroform/methanol as the eluents to afford compound 9' (488 mg, 80%). $^1$H NMR (400 MHz, DMSO-d$_6$): δ 8.78 (s, 1H), 8.70 (d, J=8.0 Hz, 1H), 8.49 (d, J=8.0 Hz, 1H), 8.42 (s, 1H), 7.24-7.10 (m, 10H), 4.96 (dd, J=16.0, 28.0 Hz, 2H), 4.61-4.56 (m, 1H), 4.46-4.40 (m, 1H), 3.09-2.99 (m, 2H), 2.91 (dd, J=8.0, 12.0 Hz, 1H), 2.75 (dd, J=8.0, 12.0 Hz, 1H), 1.37 (s, 18H) ppm.

Synthesis of Adenine-Phe-Phe-glucosamine (2A'). Compound 9' (687.7 mg, 1 mmol) and NHS (126.5 mg, 1.1 mmol) were dissolved in THF (30 mL), and DCC (226.6 mg, 1.1 mmol) was added to the above solution with stirring. After the reaction, the mixture was stirred at room temperature for 12 h, and the resulted solid was filtered off. The filtrate was evaporated under reduced pressure to dryness. The crude product was used for the next reaction without purification.

D-glucosamine hydrochloride (215.64 mg, 1 mmol) and Na$_2$CO$_3$ (212 mg, 2 mmol) were dissolved in water (20 mL) with stirring, and the solution of crude product (dissolved in 30 mL of THF) was added. The resulted reaction mixture was stirred at room temperature for 24 h. After evaporation of the organic solvent, the residue treated with 90% trifluoroacetic acid in water for 2 h. Then the mixture was concentrated by vacuum and purified by using HPLC with water-acetonitrile as eluent (from 8:2 to 5:5) to afford the product (2A') in 37% yield. $^1$H NMR (400 MHz, DMSO-d$_6$): δ 8.45 (d, J=8.0 Hz, 1H), 8.18 (d, J=8.0 Hz, 1H), 8.11 (s, 1H), 7.95-7.90 (m, 2H), 6.57 (d, J=4.0 Hz, 1H), 4.96 (b, 1H), 4.82-4.50 (m, 5H), 3.67-3.45 (m, 4H), 3.18-2.69 (m, 7H) ppm.

Synthesis of Bis-Boc-Cytosine-Phe (11'). Compound 11' was synthesized by following the procedures described in synthesis of compound 7 except replacing the bis-Boc adenine acetic acid with bis-Boc cytosine acetic acid. Compound 11' (white powder) was collected with 83% yield (429 mg). $^1$H NMR (400 MHz, DMSO-d$_6$): δ 8.29 (s, 1H), 8.01 (d, J=4.0 Hz, 1H), 7.22-7.16 (m, 5H), 6.79 (d, J=8.0 Hz, 1H), 4.58-4.41 (m, 2H), 4.27 (s. 1H), 1.49 (s, 18H) ppm.

Synthesis of Cytosine-Phe-Glucosamine (1C'). Compound 1C' was synthesized by following the procedures described in synthesis of compound 1A' except replacing the bis-Boc adenine acetic acid with bis-Boc cytosine acetic acid. Compound 1C' (white powder) was collected with 45% yield. $^1$H NMR (400 MHz, DMSO-d$_6$): δ 8.52-8.44 (m, 1H), 8.01-7.92 (m, 1H), 7.71-7.63 (m, 1H), 7.30-7.13 (m, 5H), 6.53 (d, J=8.0 Hz, 1H), 5.93-5.84 (m, 1H), 5.03-4.90 (m, 2H), 4.69-4.28 (m, 4H), 3.72-3.34 (m, 4H), 3.18-2.69 (m, 5H) ppm.

Synthesis of Bis-Boc-Cytosine-Phe-Phe (12'). Compound 12' was synthesized by following the procedures described in synthesis of compound 9' except replacing the bis-Boc adenine acetic acid with bis-Boc cytosine acetic acid. Compound 12' (white powder) was collected with 61% yield (283 mg). $^1$H NMR (400 MHz, DMSO-d$_6$): δ 8.51 (d, J=8.0 Hz, 1H), 8.41 (d, J=8.0 Hz, 1H), 7.94 (d, J=8.0 Hz, 1H), 7.29-7.16 (m, 10H), 6.77 (d, J=8.0 Hz, 1H), 4.58-4.38 (m, 4H), 3.07-2.71 (m, 4H), 1.48 (s, 18H) ppm.

Synthesis of Cytosine-Phe-Phe-Glucosamine (2C'). Compound 2C' was synthesized by following the procedures described in synthesis of compound 2A' except replacing the bis-Boc adenine acetic acid with bis-Boc cytosine acetic acid. Compound 2C' (white powder) was collected with 39% yield (360 mg). $^1$H NMR (400 MHz, DMSO-d$_6$): δ 8.32 (d, J=8.0 Hz, 1H), 8.17-8.10 (m, 1H), 7.95-7.87 (m, 1H), 7.53 (d, J=8.0 Hz, 1H), 7.32-7.13 (m, 10H), 6.56 (s, 1H), 5.80 (d, J=8.0 Hz, 1H), 4.96 (m, 2H), 4.71-4.29 (m, 5H), 3.71-3.45 (m, 4H), 3.18-2.66 (m, 7H) ppm.

Synthesis of Bis-Boc-Guanine-Phe (13'). Compound 13' was synthesized by following the procedures described in synthesis of compound 7 except replacing the bis-Boc adenine acetic acid with bis-Boc guanine acetic acid. Compound 13' (white powder) was collected with 81% yield (462 mg). $^1$H NMR (400 MHz, DMSO-d$_6$): δ 8.71 (d, J=8.0 Hz, 1H), 8.51 (d, J=8.0 Hz, 1H), 7.31-7.19 (m, 5H), 4.91-4.79 (m, 2H), 4.44 (m, 1H), 3.06-3.01 (m, 2H), 2.94-2.88 (m, 2H), 1.34 (s, 18H) ppm.

Synthesis of Guanine-Phe-glucosamine (1G'). Compound 1G' was synthesized by following the procedures described in synthesis of compound 1A' except replacing the bis-Boc adenine acetic acid with bis-Boc guanine acetic acid. Compound 1G' (white powder) was collected with 41% yield (462 mg). $^1$H NMR (400 MHz, DMSO-d$_6$): δ 8.43 (d, J=8.0 Hz, 1H), 8.11-8.04 (m, 1H), 7.30-7.14 (m, 5H), 6.57 (d, J=4.0 Hz, 1H), 4.92 (b, 2H), 4.71-4.46 (m, 4H), 3.70-3.44 (m, 4H), 3.16-2.67 (m, 5H) ppm.

Synthesis of Bis-Boc-Guanine-Phe-Phe (14'). Compound 9' was synthesized by following the procedures described in synthesis of compound 4' except replacing the bis-Boc adenine acetic acid with bis-Boc guanine acetic acid. Compound 14' (white powder) was collected with 75% yield (528 mg). $^1$H NMR (400 MHz, DMSO-d$_6$): δ 8.52 (d, J=8.0 Hz, 1H), 8.45 (s, 1H), 7.93 (s, 1H), 7.23-7.17 (m, 10H), 4.83-4.70 (m, 2H), 4.56 (s, 1H), 4.40 (s, 1H), 3.08-2.99 (m, 2H), 2.92-2.71 (m, 2H), 1.33 (s, 18H) ppm.

Synthesis of Guanine-Phe-Phe-glucosamine (2G'). Compound 2G' was synthesized by following the procedures described in synthesis of compound 2A' except replacing the bis-Boc adenine acetic acid with bis-Boc guanine acetic acid. Compound 2G' (white powder) was collected with 43% yield (292 mg). $^1$H NMR (400 MHz, DMSO-d$_6$): δ 8.41 (d, J=8.0 Hz, 1H), 8.24 (d, J=8.0 Hz, 1H), 7.99 (d, J=8.0 Hz, 1H), 7.72 (b, 1H), 7.33-7.10 (m, 10H), 6.57 (s, 1H), 4.96 (s, 2H), 4.70-4.61 (m, 3H), 4.51 (m, 2H), 3.72-3.47 (m, 4H), 3.17-2.67 (m, 7H) ppm.

Example 3'

Transmission Electron Microscopy (TEM)

Micrographs are depicted in FIG. 20, FIG. 21, FIG. 22, FIG. 23, and FIG. 24.

Example 4'

UV-Vis and Circular Dichroism (CD) Spectroscopy

CD spectra were recorded (185-350 nm) using a JASCO 810 spectrometer under a nitrogen atmosphere. The hydrogels (0.2 mL, 3.0 wt %) were placed evenly on the 1 mm thick quartz curvet and scanned with 0.5 nm interval.

FIG. 25, FIG. 26, FIG. 27, and FIG. 28 depict various UV-Vis and CD spectra.

Example 5'

Rheological Measurements

Figure 28:
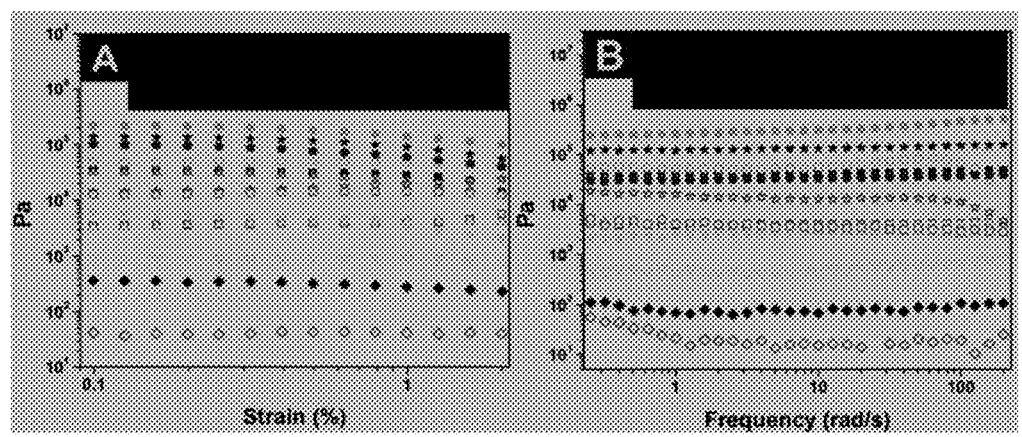
FIG. 28 depicts (A) strain dependence of dynamic storage moduli (G') and loss moduli (G") of hydrogels of 1T' (G'=closed square, G"=open square), 2T' (G'=closed triangle with apex at the top; G"=open triangle with apex at the top), 2C' (G'=closed circle; G"=open circle), 1A' (G'=closed triangle with apex at the bottom; G"=open triangle with apex at the bottom), 2A' (G'=closed diamond; G"=open diamond), 1G' (G'=closed star; G"=open star), and 2G' (G'=closed pentagon; G"=open pentagon); (B) frequency dependence of dynamic storage moduli (G') and loss moduli (G") of hydrogels of 1T' (G'=closed square, G"=open square), 2T' (G'=closed triangle with apex at the top; G"=open triangle with apex at the top), 2C' (G'=closed circle; G"=open circle), 1A' (G'=closed triangle with apex at the bottom; G"=open triangle with apex at the bottom), 2A' (G'=closed diamond; G"=open diamond), 1G' (G'=closed star; G"=open star), and 2G' (G'=closed pentagon; G"=open pentagon), as shown in FIG. 19.

Rheological tests were conducted on TA ARES G2 rheometer (with TA Orchestrator Software). 25 mm parallel plate was used during the experiment. 0.5 mL of hydrogel sample was placed on the parallel plate. FIG. 26 and FIG. 28 depict data from these experiments.

i) Dynamic Strain Sweep Test

Test range (0.1 to 10% strain, frequency=10 rads$^{-1}$), 10 points per decade. Sweep mode is "log" and temperature was carried out at 25° C.

ii) Critical Strain Determination

The critical strain ($\gamma_0$) value was determined from the storage-strain profiles of the hydrogel sample. The strain applied to the hydrogel sample increased from 0.1 to 100% (10 rad/s and 25° C.). Over a certain strain, a drop in the elastic modulus was observed, and the strain amplitude at which storage moduli just begins to decrease by 5% from its maximum value was determined and taken as a measure of the critical strain of the hydrogels, which correspond to the breakdown of the cross-linked network in the hydrogel sample.

Example 6'

Wound-Healing Assay

HeLa cells were re-suspended in 10 cm tissue culture dish after washing cells once with PBS. 0.8 mL 0.25% trypsin containing 0.1% EDTA was then added, and the cells were re-suspended with 1.6 mL complete medium. 5000 cells (in 100 μL medium) were plated into each vial on a 96 well plate to create a confluent monolayer. After adherent for 24 h, a wound was created by scraping the cell monolayer with a p200 pipet tip. The cells were washed once with 100 μL of complete medium to remove flowing cells and replace with 100 μL of complete medium. 0 h image was acquired as a reference point. The medium was replaced with 100 μL of medium containing 500 μM of hydrogelator 1T' and the plate was incubate at 37° C., 5% $CO_2$ for 20 h. 0 h and 20 h images were acquired at the match photographed region.

Example 7'

Biostability 1 mg of each compound was dissolved in 5 mL HEPES buffer at pH=7.5. Then proteinase K were added in concentration 3.2 units/mL and incubated at 37° C. for 24 h, then 100 μL of sample were taken out each time and analyzed by HPLC.

Figure 33:
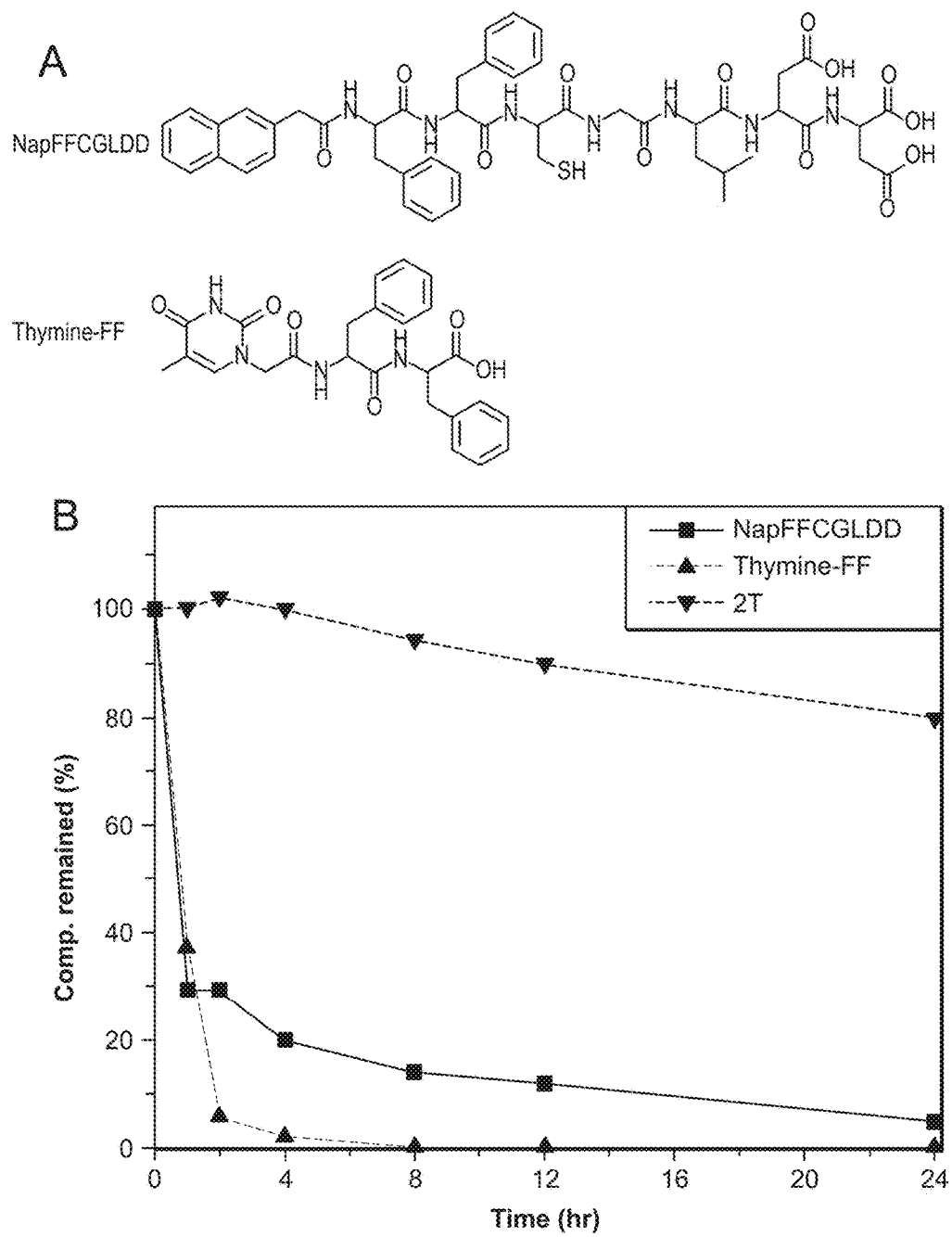
FIG. 33 depicts (A) the molecular structures of NapFFCGLDD and thymine-FF, and (B) their time-dependent course of the digestions by proteinase K as control experiment, in which NapFFCGLDD is the heptapeptide derivative and thymine-FF is the nucleopeptide without D-glucosamine in conjugation. Note in (B) that the triangle with the apex at the bottom relates to 2T'.

For the control experiment, 1 mg of NapFFCGLDD (heptapeptide derivative) and 1 mg of thymine-FF (nucleopeptides without glucosamine in conjugation) were dissolved in 5 mL HEPES buffer at pH=7.5 respectively. Then proteinase K were added in concentration 3.2 units/mL and incubated at 37° C. for 24 h, then 100 μL of sample were taken out each time and analyzed by HPLC. FIG. 33.

Example 8'

Preparation of 1T'+Deoxyadenosine (A10) Mixed Gel and Test of the Interaction Between 1T' and A10

Figure 31:
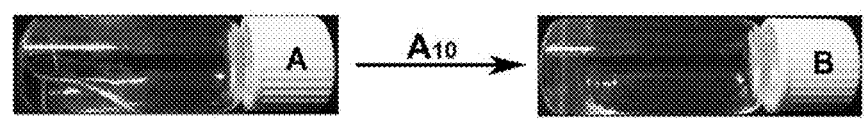
FIG. 31 depicts optical images of (A) the highly viscous solution of 1T' (2.1 wt %, pH=7.0); (B) 1T'+deoxyadenosine (A$_{10}$) mixed hydrogel after the addition of deoxyadenosine (A$_{10}$) in 1:1 molecular ratio.
Figure 32:
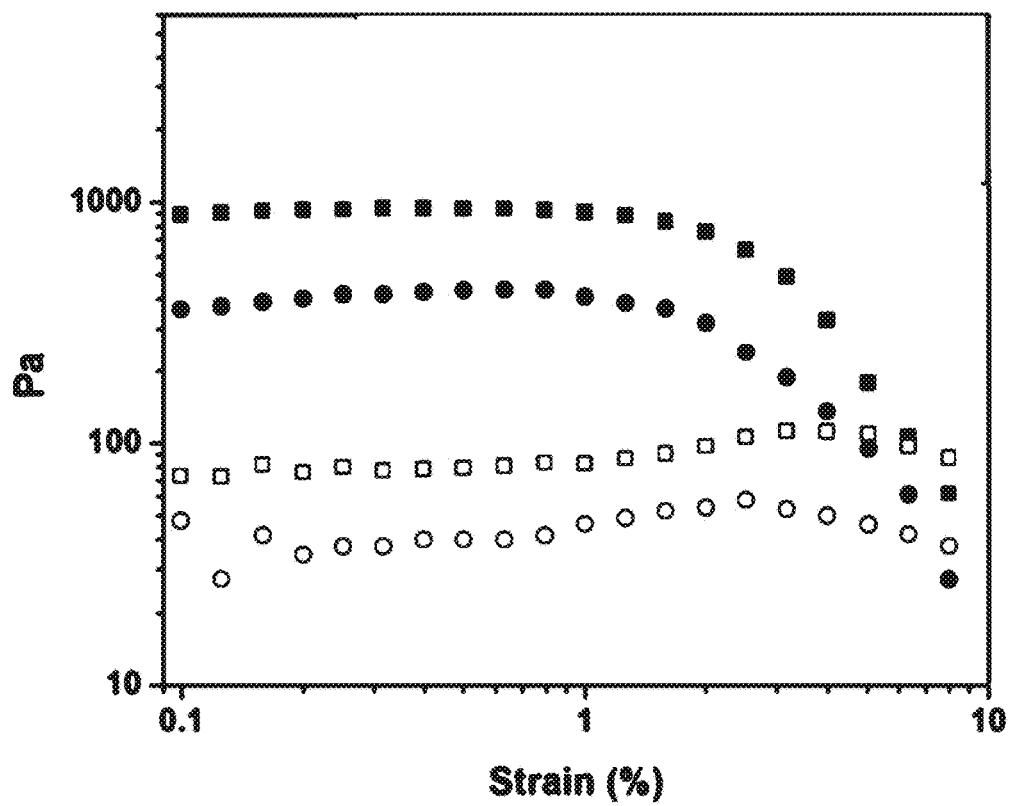
FIG. 32 depicts (left) strain dependence of dynamic storage moduli (G') and loss moduli (G") of the hydrogels of 1T' (G'=closed circle; G"=open circle) and 1T'+deoxyadenosine (A$_{10}$) mixed gel (G'=closed square; G"=open square); (right) frequency dependence of dynamic storage moduli (G') and loss moduli (G") of the hydrogels of 1T' (G'=closed diamond; G"=open diamond), and 1T'+deoxyadenosine (A$_{10}$) mixed gel (G'=closed triangle; G"=open triangle) shown in FIG. 31.
Figure 32:
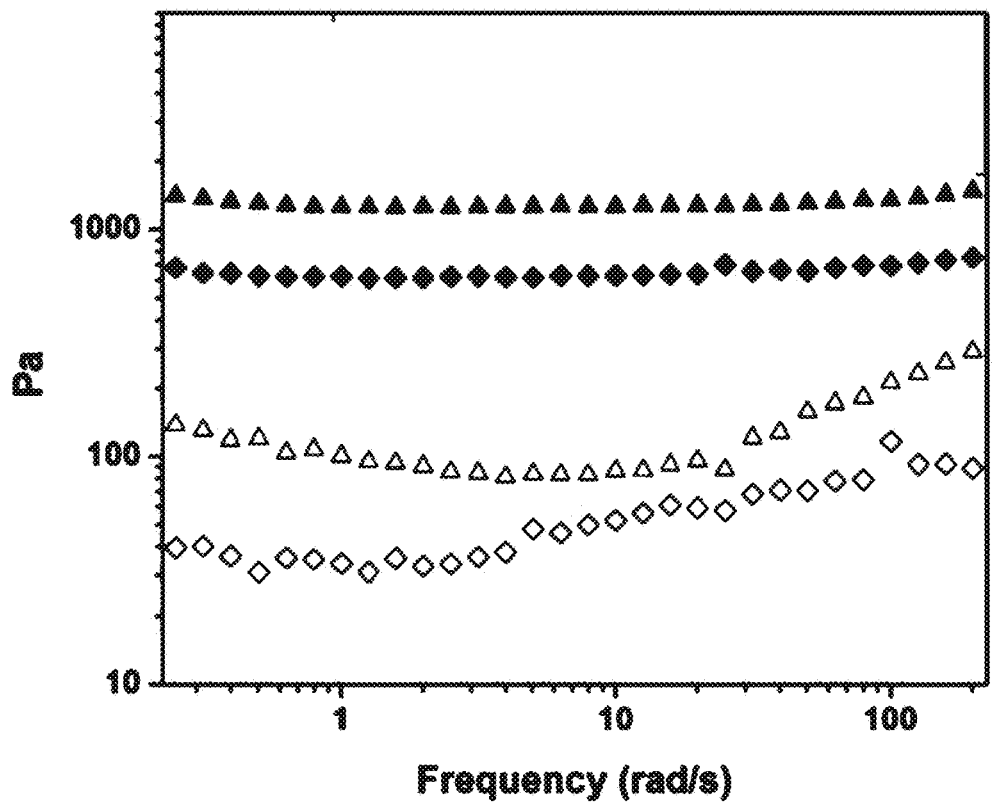

The typical procedure for hydrogelation: 5.9 mg of 1T' dissolves in 224 μL water in 2.1 wt % with gentle heating to make clear solution, and followed by the addition of 57 μL of deoxyadenosine ($A_{10}$) (20 mM) to afford stable mixed hydrogel. And this mixed hydrogel was subject to CD, TEM and rheological studies to test the interaction between 1T' and deoxyadenosine ($A_{10}$). FIG. 31 and FIG. 32.

Example 9'

Nucleic Acid Delivery to the Cell Nuclei with Aid of 1T'

Figure 34:
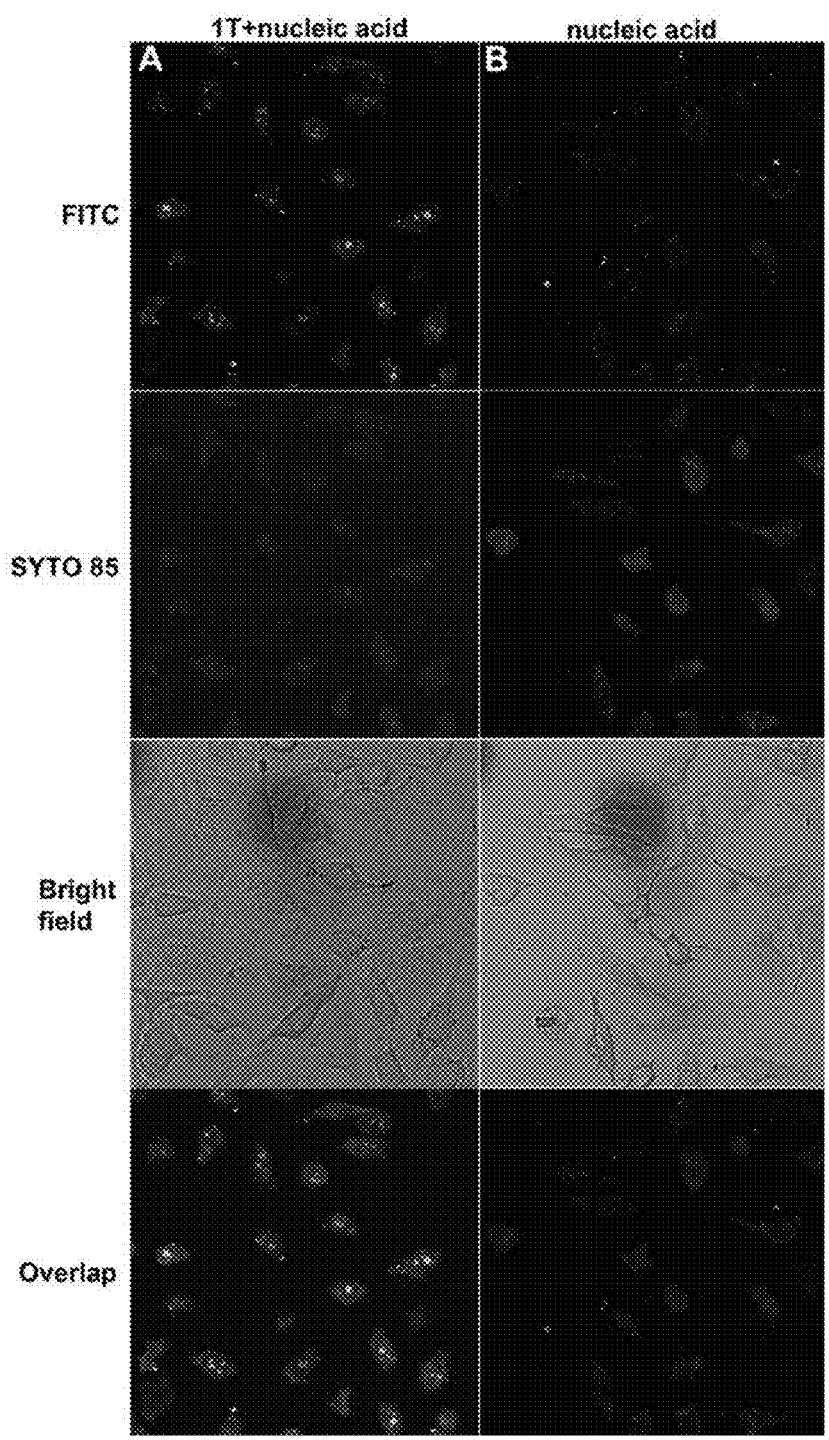
FIG. 34 depicts fluorescence and bright field microscopy images illustrating nuclear localization of DNA released from the 1T' and nucleic acid complex. Nucleic acid was labeled with fluorescein dye (FITC) (green). Cell nuclei were stained with SYTO 85. (A) 500 µM 1T' and 0.1 µM nucleic acid labeled with FITC complex incubated with HeLa cells for 24 h. (B) 0.1 µM nucleic acid labeled with FITC incubated with HeLa cells for 24 h.
Figure 35A:
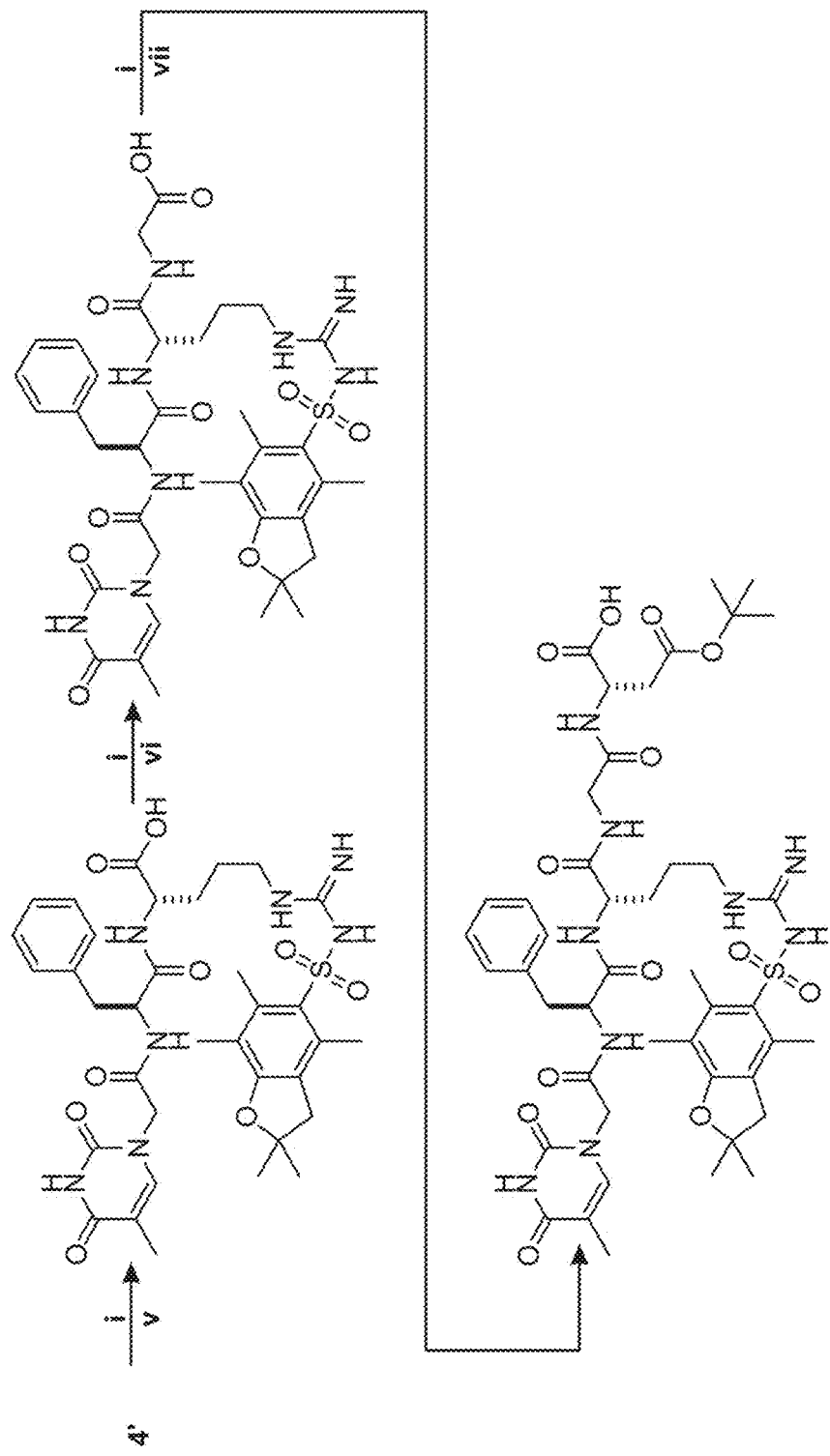
FIG. 35 depicts the molecular structures and exemplary synthetic routes for the preparation of hydrogelators of the invention.
Figure 35B:
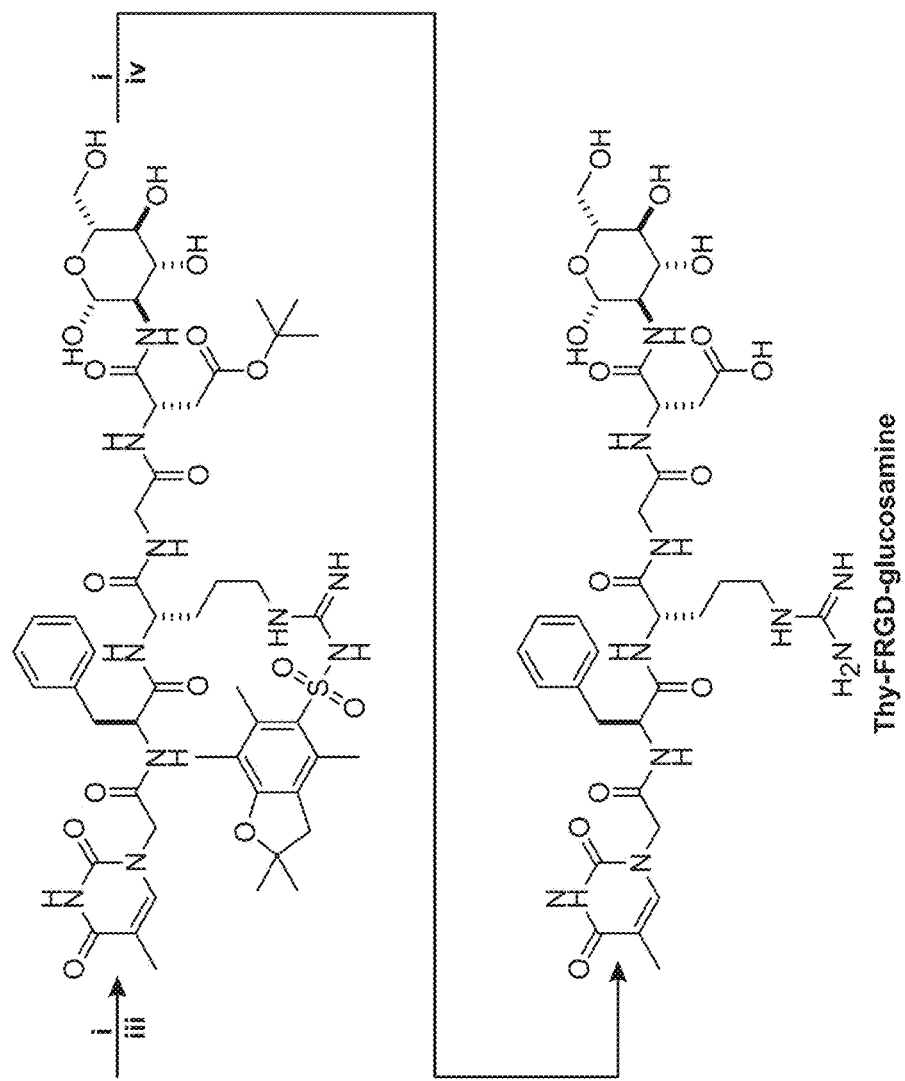
Figure 35C:
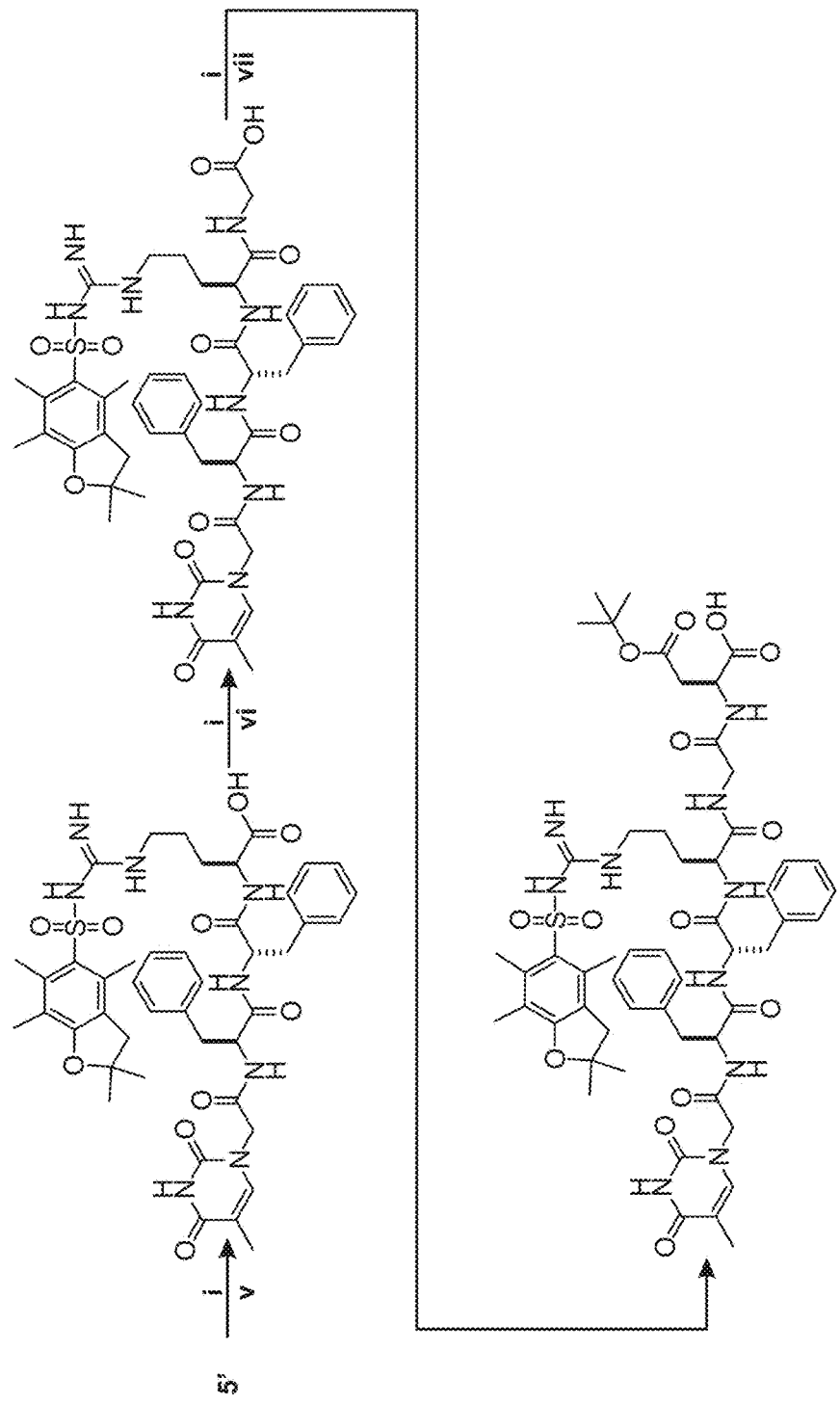
Figure 35D:
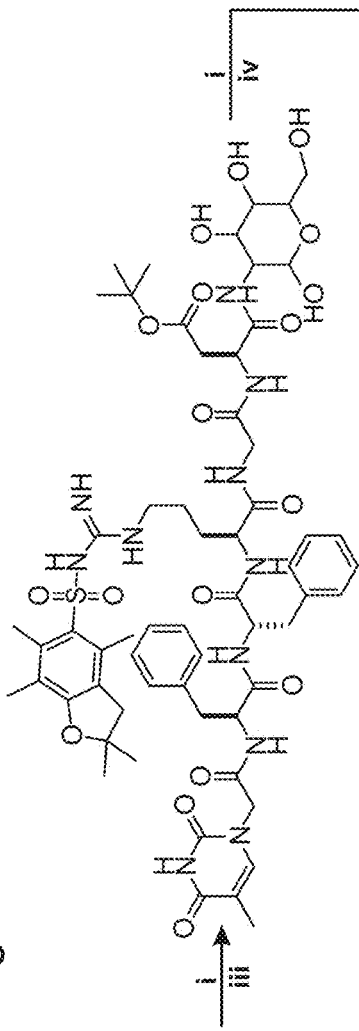
Figure 35D:
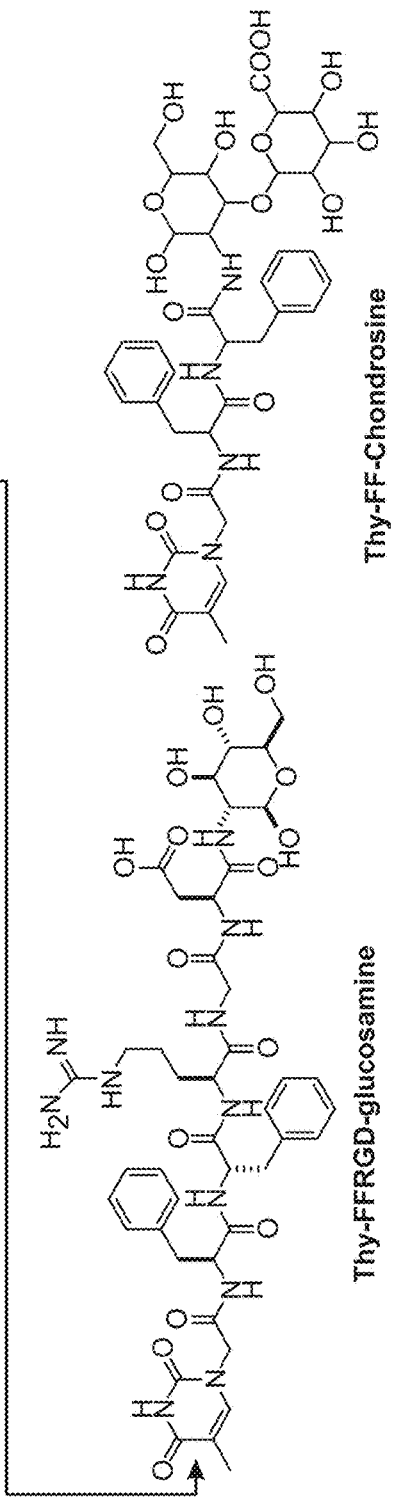
Figure 36:
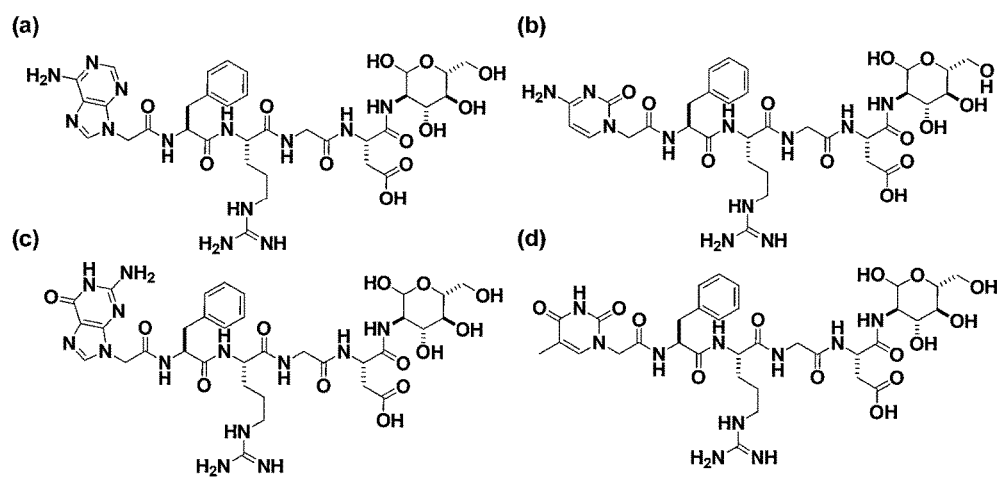
FIG. 36 depicts the molecular structures of hydrogelators consisting of nucleobase, RGD peptides, and glycoside. (a) 1A'+RGD; (b) 1C'+RGD; (c) 1G'+RGD; (d) 1T'+RGD.
Figure 37:
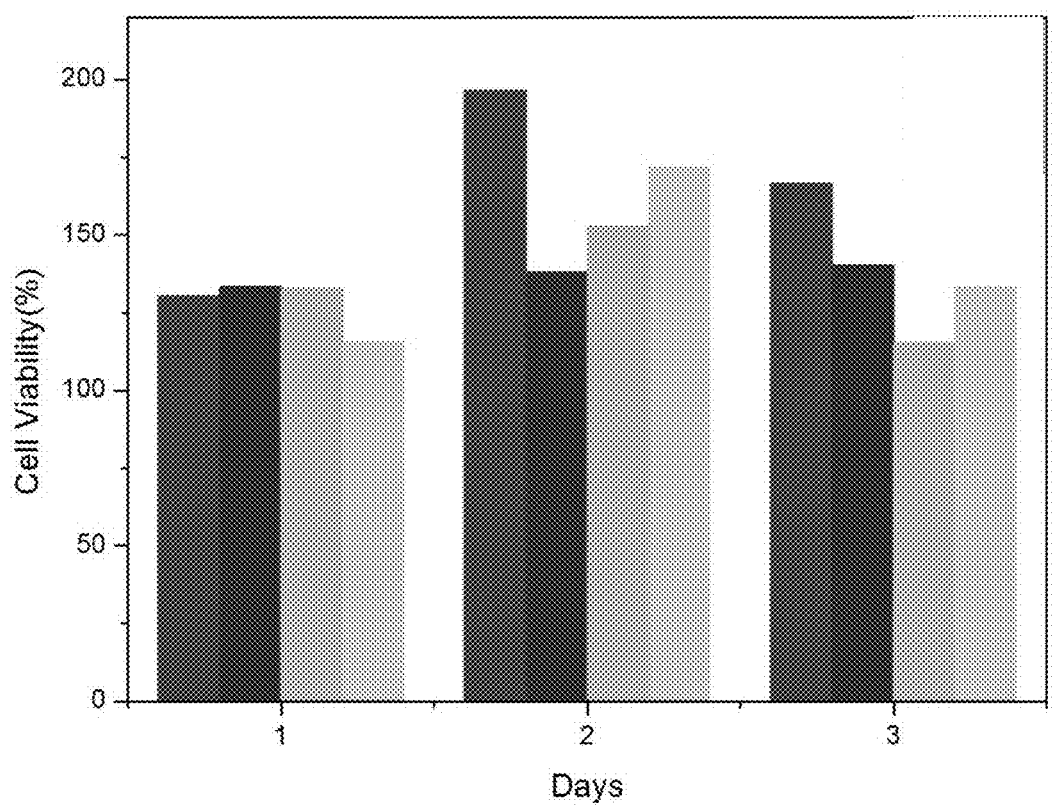
FIG. 37 depicts the cell viability (by cell number counting) of the 20,000 HeLa cells in Minimum Essential Medium treated with protease-tolerant supramolecular hydrogels of the compounds depicted in FIG. 36 (left bar=1A'+RGD; second left bar=1T'+RGD; second right bar=1C'+RGD; right bar=1G'+RGD).
Figure 38:
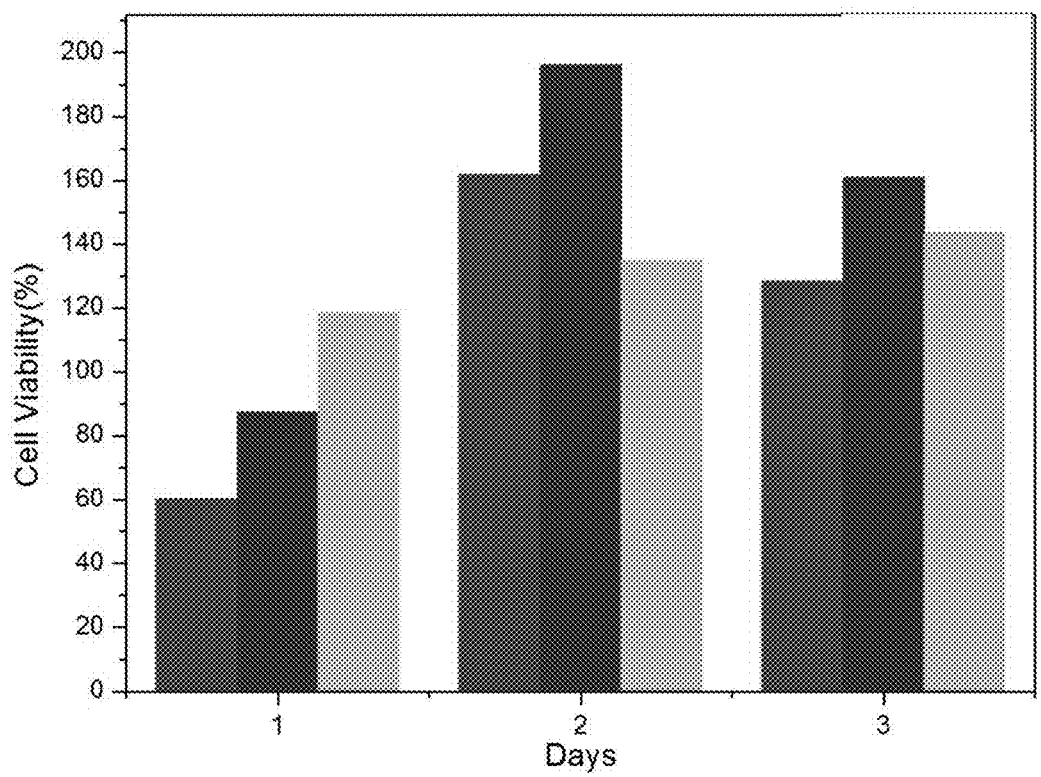
FIG. 38 depicts cell viability (by cell number counting) of 20,000 Embryonic Stem Cells inhibited by a protease-tolerant supramolecular hydrogel of the compound depicted in FIG. 36(a) (1A'+RGD) in Primary Mouse Embryo Fibroblasts (PMEF) (left bar=100 µM; middle bar=200 µM; right bar=500 µM).

HeLa cells were seeded in 2 well chamber slide at a density of 10,000 cell/well. After allowing the attachment at 37° C. for 4 h, we removed culture medium and applied 1 mL of culture medium containing 0.1 μM fluorescein (FITC) labeled poly(10A) with or without 500 μM hydrogelator 1T'. After incubation at 37° C. for 24 h, we removed the culture medium, washed the cells by 1 mL PBS for 3 times, then resin the cells in 1 mL PBS. Fluorescence images were taken by using confocal fluorescence microscope. FIG. 34.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. A hydrogelator of Formula I(b)

I(a)

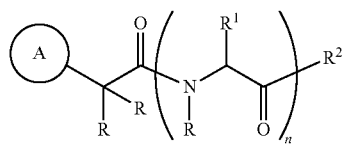

I(b)

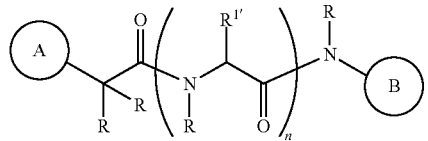

wherein

is cytosinyl, guaninyl, adeninyl, or thyminyl;
each R is independently H or alkyl;

n is 2 or 5, whereby the peptide defined by

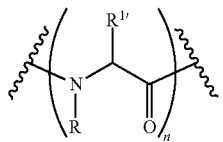

in Formula I(b) is $_L$Phe-$_L$Phe or $_L$Phe-$_L$Phe-$_L$Arg-$_L$Gly-$_L$Asp; and

is glucosyl, or chondrosinyl.

2. The hydrogelator of claim 1, wherein each R is H.
3. The hydrogelator of claim 1, wherein

is glucosyl.

4. The hydrogelator of claim 1, wherein

is chondrosinyl.

5. The hydrogelator of claim 1, wherein n is 2 and the peptide defined by

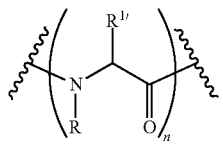

in Formula I(b) is $_L$Phe-$_L$Phe.

6. The hydrogelator of claim 1, wherein the hydrogelator is a compound selected from the group consisting of:

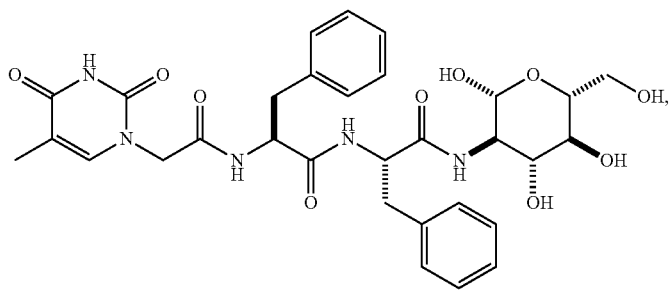

-continued
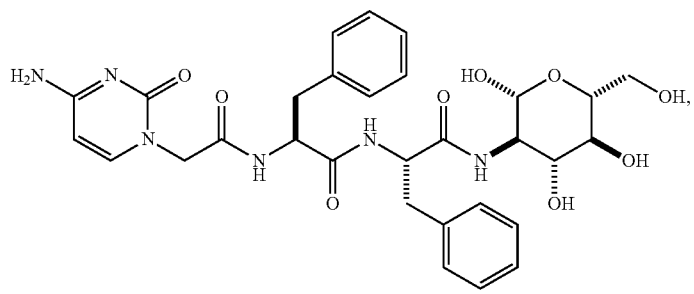
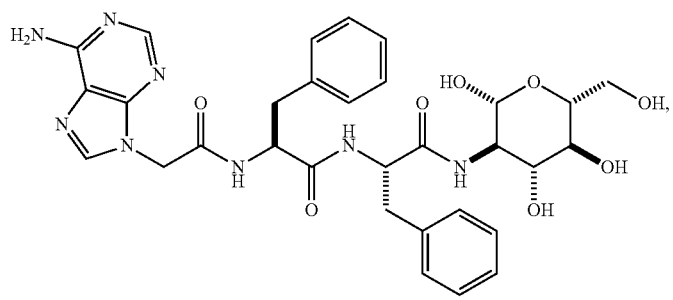
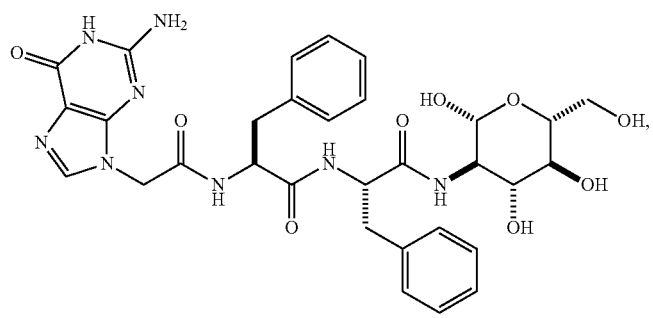
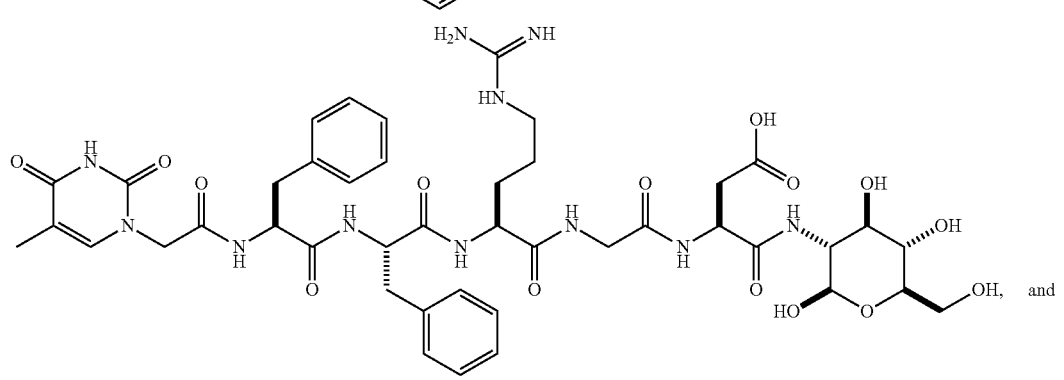
and
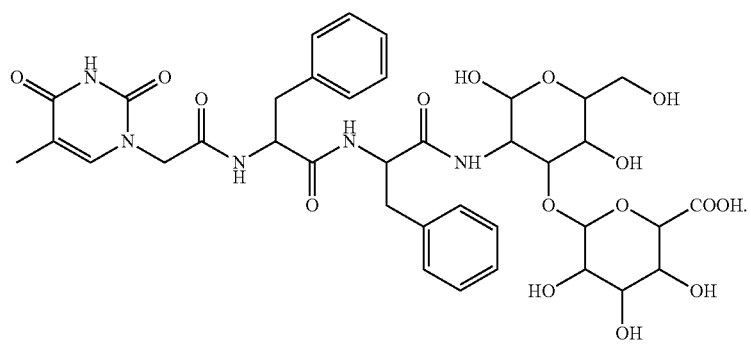

7. A hydrogel, comprising a plurality of hydrogelators of claim 1; and water.

8. A method of growing cells, comprising contacting a plurality of cells with a hydrogel of claim 7.

9. A method of delivering a substance to a cell, comprising:
   contacting the substance with a hydrogel of claim 7, thereby forming a substance-hydrogel delivery vehicle; and
   contacting a cell with the substance-hydrogel delivery vehicle to deliver the substance to the cell.

10. A method of binding a nucleic acid, comprising:
    contacting a nucleic acid with a hydrogel of claim 7 and thereby binding the nucleic acid to the hydrogel.

11. A method of preventing adhesion of an organism or a cell to a surface, comprising contacting the surface with a hydrogel of claim 7, wherein adhesion of an organism or a cell to the hydrogel-contacted surface is prevented.

12. The hydrogelator of claim 1, wherein n is 5 and the peptide defined by

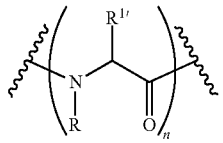

in Formula I(b) is $_L$Phe-$_L$Phe-$_L$Arg-$_L$Gly-$_L$Asp.

* * * * *

UNITED STATES PATENT AND TRADEMARK OFFICE
CERTIFICATE OF CORRECTION

PATENT NO. : 10,093,674 B2
APPLICATION NO. : 14/093974
DATED : October 9, 2018
INVENTOR(S) : Bing Xu Page 1 of 1

It is certified that error appears in the above-identified patent and that said Letters Patent is hereby corrected as shown below:

On the Title Page

Item (63), second and third lines, delete "which is a" and insert --and--.

In the Specification

Column 1, Line 21, delete "DMR 0820492" and insert --R01 CA142746--.

Column 1, Line 22, after "and" insert --DMR0820492 awarded by--.

In the Claims

Claim 1, Column 41, Lines 21-32, delete the following structure:

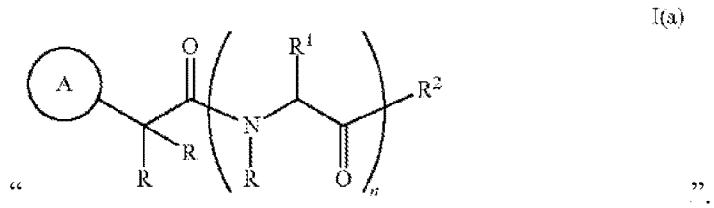

".

Signed and Sealed this
Twenty-ninth Day of January, 2019

Andrei Iancu
*Director of the United States Patent and Trademark Office*